(12) United States Patent
Regeimbal et al.

(10) Patent No.: US 10,357,522 B2
(45) Date of Patent: Jul. 23, 2019

(54) BACTERIOPHAGE COMPOSITIONS AND METHODS OF SELECTION OF COMPONENTS AGAINST SPECIFIC BACTERIA

(71) Applicant: The United States of America as Represented by the Secretary of the Navy, Washington, DC (US)

(72) Inventors: James M Regeimbal, Washington's Crossing, PA (US); Biswajit Biswas, Germantown, MD (US); Matthew S. Henry, Thurmont, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/628,368

(22) Filed: Jun. 20, 2017

(65) Prior Publication Data
US 2017/0368116 A1    Dec. 28, 2017

Related U.S. Application Data

(60) Provisional application No. 62/353,517, filed on Jun. 22, 2016, provisional application No. 62/489,860, filed on Apr. 25, 2017, provisional application No. 62/510,649, filed on May 24, 2017.

(51) Int. Cl.
| | |
|---|---|
| *C40B 30/04* | (2006.01) |
| *A61K 35/76* | (2015.01) |
| *C12N 7/00* | (2006.01) |
| *C12Q 1/18* | (2006.01) |

(52) U.S. Cl.
CPC ............ *A61K 35/76* (2013.01); *C12N 7/00* (2013.01); *C12Q 1/18* (2013.01); *C12N 2795/00021* (2013.01); *C12N 2795/00032* (2013.01); *C12N 2795/00051* (2013.01);
(Continued)

(58) Field of Classification Search
None
See application file for complete search history.

(56) References Cited

U.S. PATENT DOCUMENTS

| | | |
|---|---|---|
| 2010/0297086 A1 | 11/2010 | Mathers et al. |
| 2010/0322903 A1 | 12/2010 | Collins et al. |

(Continued)

FOREIGN PATENT DOCUMENTS

| | | |
|---|---|---|
| WO | 2008110840 A1 | 9/2008 |
| WO | 2015188230 A1 | 12/2015 |
| WO | 2017087909 A1 | 5/2017 |

OTHER PUBLICATIONS

Borysowski, J, et al., "Bacteriophage Endolysins as a Novel Class of Antibacterial Agents", Experimental Biology and Medicine, vol. 231, pp. 366-377, (2006).

(Continued)

*Primary Examiner* — Christian C Boesen
(74) *Attorney, Agent, or Firm* — Michele M. Wales; Diane P. Tso; Albert M. Churilla

(57) ABSTRACT

The subject matter of the instant invention relates to methods of compounding compositions comprising bacteriophage effective for treating bacterial infections, including but not limited to, multidrug resistant bacterial infections. The invention also relates to compositions, bacterial diversity sets, and phage libraries prepared according to the methods of the instant invention.

23 Claims, 32 Drawing Sheets

(52) U.S. Cl.
CPC .............. *C12N 2795/10121* (2013.01); *C12N 2795/10132* (2013.01); *C40B 30/04* (2013.01); *G01N 2500/10* (2013.01)

(56) References Cited

U.S. PATENT DOCUMENTS

2013/0315869 A1  11/2013  Qimron et al.
2016/0010138 A1   1/2016  Shamsheyeva et al.

OTHER PUBLICATIONS

Chanishvili N. "Bacteriophages as Therapeutic and Prophylactic Means: Summary of the Soviet and Post Soviet Experiences", Current Drug Delivery, vol. 13, No. 3, pp. 309-323, (2016).
Davis, J. et al., "Combination of Vancomycin and ?-Lactam Therapy for Methicillin-Resistant *Staphylococcus aureus* Bacteremia: A Pilot Multicenter Randomized Controlled Trial", MRSA Bacteremia Combination Treatment—CID, vol. 32, pp. 173-180, (2016).
Debarbieux, L. et al., "A Bacteriophage Journey at the European Medicines Agency", FEMS Microbiology Letters, vol. 363, doi: 10.1093/femsle/fnv225, (2016).
Gelband, H. et al., "The State of the World's Antibiotics 2015", Center for Disease Dynamics, Economics & Policies, Executive Summary, CDDEP: Washington, D.C., pp. 1-16, (2015).
Gu, et. al., "A Method for Generation Phage Cocktail With Great Therapeutic Potential", PLoS ONE, vol. 7, Issue 3, Mar. 2012, pp. 1-8.
Hauser, A., et al., "Beyond Antibiotics: New Therapeutic Approaches for Bacterial Infections", Healthcare Epidemiology—CID, vol. 63, pp. 89-95, (2016).
Hraiech, S. et al., "Bacteriophage-Based Therapy in Cystic Fibrosis-Associated Pseudomonas Aeruginosa Infections: Rationale and Current Status", Drug Design, Development and Therapy, vol. 9, 3653-3663, (2015).
Magana, M. et al., "Therapeutic Options and Emerging Alternatives for Multidrug Resistant Staphylo-coccal Infections", Current Pharmaceutical Design, vol. 21, No. 16, pp. 2058-2072, (2015).
Ochs, H. et al., "Antibody Responses to Bacteriophage Phi X174 in Patients with Adenosine Deaminase Deficiency", Blood, vol. 80, No. 5, pp. 1163-1171, (1992).
Parasion, S. et al., "Bacteriophages as an Alternative Strategy for Fighting Biofilm Development", Polish Journal of Microbiology, vol. 63, No. 2, pp. 137-145, (2014).
Speck, P. and Smithyman, A., "Safety and Efficacy of Phage Therapy via the Intravenous Route", FEMS Microbiology Letters, Minireview—Virology, vol. 363, doi: 10.1093/femsle/fnv242, (2016).
Sulakvelidze, A. et al., "Bacteriophage Therapy", Antimicrobial Agents and Chemotherapy, vol. 45, No. 3, pp. 649-659, DOI: 10.1128/AAC.45.3.649-659.2001, (2001).
Verbeken, G. et al., "Call for a Dedicated European Legal Framework for Bacteriophage Therapy", Archivum Immunologiae et Therapiae Experimentalis, vol. 62, pp. 117-129, DOI I0.1007/s00005-014-0269-y, (2014).
Wittebole, X. et al., "A Historical Overview of Bacteriophage Therapy as an Alternative to Antibiotics for the Treatment of Bacterial Pathogens", Virulence, vol. 5, No. 1, pp. 226-235, (2014).
Eihupathiraju et al., Journal of Microbiological Methods, 37, p. 231-243, Sep. 2003.
Biswas et al., Infection and Immunity, vol. 70, No. 1, pp. 204-210, (2002).
Cooper, C. et al., "Adapting Drug Approval Pathways for Bacteriophage-Based Therapeutics", Frontiers in Microbiology, vol. 7, No. 1209, (2016).
Estrella, L. et al., "Characterization of Novel *Staphylococcus aureus* Lytic Phage and Defining their Combinatorial Virulence Using the OmniLog System", Bacteriophage, vol. 6, No. 3, e1219440, DOI: 10.1080/21597081.2016.1219440 Published online, (2016).
Hatzinger, R et al., "Applicability of Tetrazolium Salts for the Measurement of Respiratory Activity and Viability of Groundwater Bacteria", Journal of Microbiological Methods, vol. 52, pp. 47-58, (2003).
Henry et al., "Development of a High Throughput Assay for Indirectly Measuring Phage Growth Using the OmniLogTM system", Bacteriophage, vol. 2, No. 3, pp. 159-167, (2012).
International Search Report and Written Opinion dated Sep. 7, 2017 received in PCT/US2017/038359.
Keen, E., Frontiers in Microbiology, vol. 3, No. 238 (2012).
Loc-Carrillo, C. and Abedon, S., "Pros and cons of phage therapy", Bacteriophage, vol. 1, No. 2, p. 111-114, (2011).
Mendes, J. et al. "In Vitro Design of a Novel Lytic bacteriophage Cocktail With Therapeutic Potential Against Organisms Causing Diabetic Foot Infections," Journal of Medical Microbiology, vol. 63, Pt. 8, pp. 1055-1065, (2014).
Merril, C. et al., "The Prospect for Bacteriophage Therapy in Western Medicine", Nature Reviews Drug Discovery, vol. 2, pp. 489-497, (2003).
Mshana, R. et al., "Use of 3-(4,5-Dimethylthiazol-2-yl)-2,5-Diphenyl Tetrazolium Bromide for Rapid Detection of Rifampin-Resistant *Mycobacterium tuberculosis*", Journal of Clinical Microbiology, vol. 36, No. 5, pp. 1214-1219, (1998).
Regeimbal, J. et al., "Personalized Therapeutic Cocktail of Wild Environmental Phages Rescues Mice from Acinetobacter baumannii Wound Infections", Antimicrobial Agents and Chemotherapy, vol. 60, No. 10, pp. 5806-5816, (2016).
Schooley, R. et al., "Development and Use of Personalized Bacteriophage-Based Therapeutic Cocktails to Treat a 2 Patient with a Disseminated Resistant Acinetobacter Baumannii Infection", Antimicrobial Agents and Chemotherapy., Doi: 10.1128/AAC.00954-17, Poste donline (2017).
Serwer, P. et al. "Enhancing and Initiating Phage-Based Therapies", Bacteriophage, vol. 4, No. 4, pp. 1-14, (2014).
Thiel, K., "Old Dogma, New Tricks-21st Century Phage Therapy", Nature Biotechnology, vol. 22, No. 1, pp. 31-36, (2004).
Volety, A. et al., "A Rapid Tetrazolium Dye Reduction Assay to Assess the Bactericidal Activity of Oyster (*Crassostrea virginica*) Hemocytes Against Vibrio Parahaemolyticus", Aquaculture, vol. 172, pp. 205-222, (1999).
International Preliminary Report on Patentability dated Sep. 7, 2017 and received in PCT/US2017/038359.
Mattila et al., "On-Demand Isolation of Bacteriophages Against Drug Resistant Bacteria for Personalized Phage Therapy", Frontiers in Microbiology, vol. 6, Article 1271, pp. 1-7 (2015).

FIG. 1

| Phage strains | Phage dilutions (pfu/ml) → | | | | | | | Phage control | Media control | Bacteria control | Bacteria inoculum (10⁵ pfu/ml) | Bacteria stock (10⁶ pfu/ml) |
|---|---|---|---|---|---|---|---|---|---|---|---|---|
| | 1 | 2 | 3 | 4 | 5 | 6 | 7 | 8 | 9 | 10 | 11 | 12 |
| | $10^7$ | $10^6$ | $10^5$ | $10^4$ | $10^3$ | $10^2$ | 10 | | | | | |
| A | | | | | | | | | | | | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

FIG. 13

| UCSD # | Navy Nomenclature | Date of Origin | Source |
|---|---|---|---|
| RY36079 | TP1 (before phage) | March 10, 2016 | Pancreatic drain 1 |
| 64210283 | TP2 | March 21, 2016 | Pancreatic drain 1 |
| 64230272 | TP3 | March 23, 2016 | Pancreatic drain 1 |
| 66091485 | TP4.1 | May 9, 2016 | Pancreatic drain 3 |
| 66093804 | TP4.2 | May 9, 2016 | Pancreatic drain 1 |
| 66093819 | TP4.3 | May 9, 2016 | Pancreatic drain 3 (Second Sample of the Day) |
| 6609384 | TP4.4 | May 9, 2016 | Pancreatic drain 5 |
| 66160214 | TP4.5 | May 16, 2016 | Pancreatic drain 5 |
| 66160779 | TP4.6 | May 16, 2016 | Pancreatic drain 1 |
| 66160780 | TP4.7 | May 16, 2016 | Pancreatic drain 3 |

FIG. 14

| | Navy Cocktail Phage<br>Intravenous administration<br># of doses/day<br>5x10⁹pfu/dose | Navy Cocktail Phage<br>Cavity- wash<br># of dose/day<br>5x10⁹pfu/dose | | Intravenous administration<br># of doses/day<br>5x10⁹pfu/dose | Navy Cocktail Phage<br>Cavity- wash<br># of dose/day<br>5x10⁹pfu/dose |
|---|---|---|---|---|---|
| March 17 | 2 | Not Given | April 5 | 4 | Not Given |
| March 18 | 2 | Not Given | April 6 | 4 | 1 |
| March 19 | 7 | Not Given | April 7 | 4 | 2 |
| March 20 | 4 | Not Given | April 8 | 4 | 3 |
| March 21 | Not Given | Not Given | April 10 | 4 | 5 |
| March 22 | Not Given | Not Given | April 11 | 4 | 4 |
| March 23 | 2 | Not Given | April 12 | 4 | 3 |
| March 24 | 3 | Not Given | April 13 | 4 | 5 |
| March 25 | 4 | Not Given | April 14 | 4 | 4 |
| March 26 | 4 | Not Given | April 15 | 4 | 4 |
| March 27 | 4 | Not Given | April 16 | 4 | 3 |
| March 28 | 4 | Not Given | April 17 | 4 | 5 |
| March 29 | 4 | Not Given | April 18 | 4 | 4 |
| March 30 | 4 | Not Given | April 19 | 4 | 4 |
| March 31 | 3 | Not Given | April 20 | 2 | 4 |
| April 1 | 4 | Not Given | April 21 | 4 | 3 |
| April 2 | 4 | Not Given | April 22 | 4 | 1 |
| April 3 | 4 | Not Given | April 23 | 4 | 3 |
| April 4 | 4 | Not Given | April 24 | 4 | 5 |

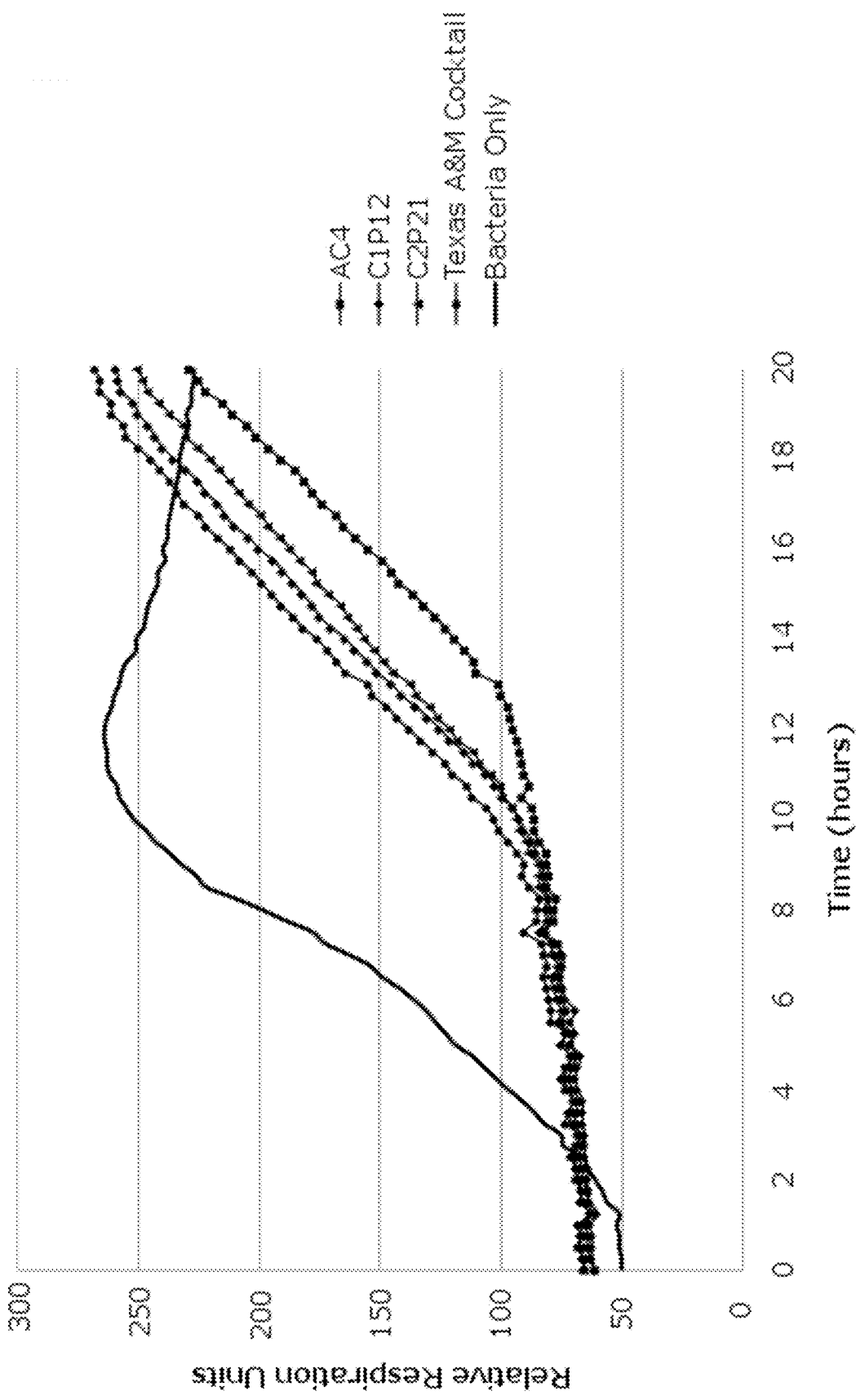

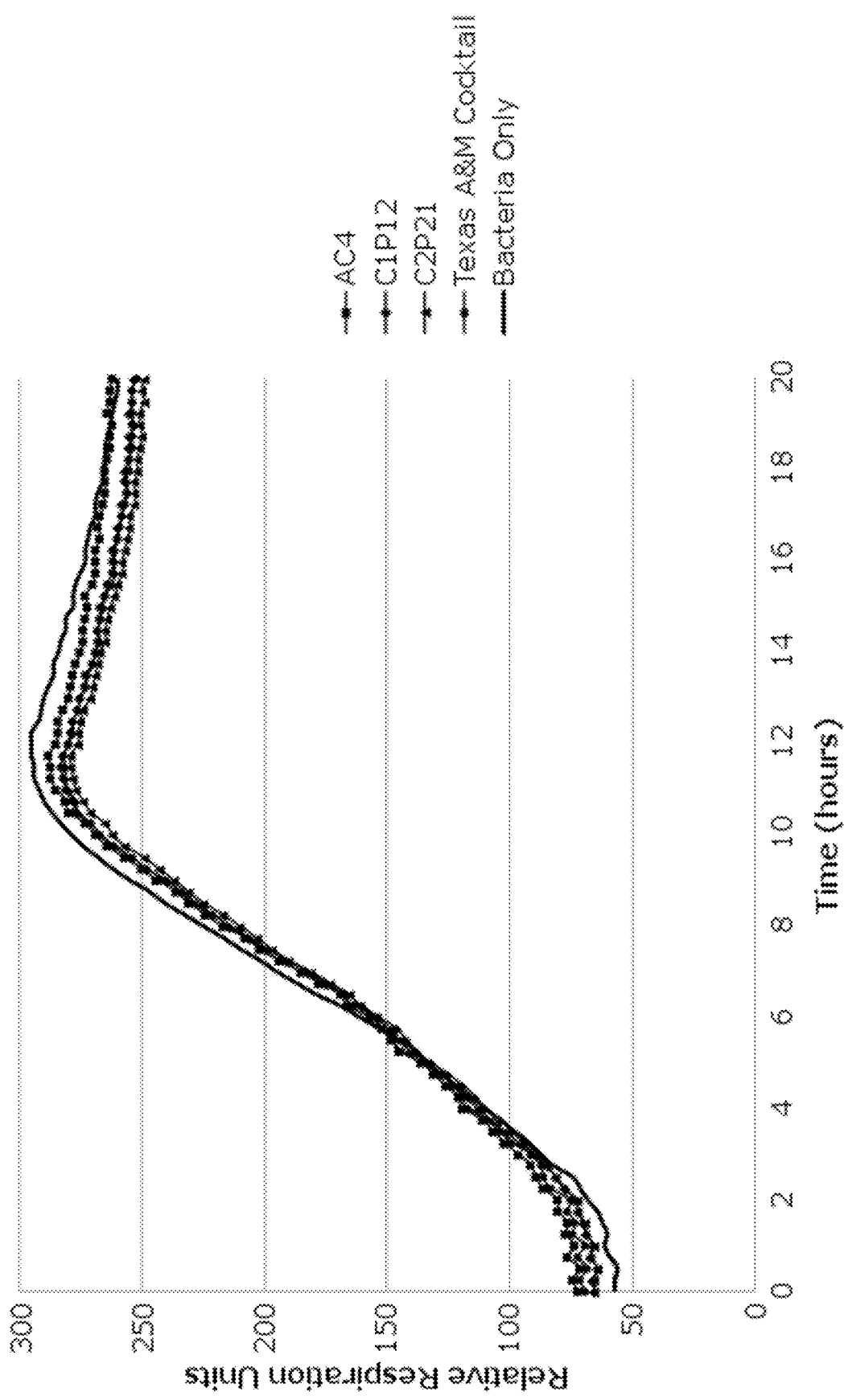

FIG. 24

Phage + Antibody

| | 1 | 2 | 3 | 4 | 5 | 6 | 7 | 8 Antibody control | 9 Media control |
|---|---|---|---|---|---|---|---|---|---|
| A | 1:10 serum $10^9$ pfu | 1:10 serum $10^8$ pfu | 1:10 serum $10^7$ pfu | 1:10 serum $10^6$ pfu | 1:10 serum $10^5$ pfu | 1:10 serum $10^4$ pfu | 1:10 serum $10^3$ pfu | 1:10 serum | |
| B | 1:$10^2$ serum $10^9$ pfu | 1:$10^2$ serum $10^8$ pfu | 1:$10^2$ serum $10^7$ pfu | 1:$10^2$ serum $10^6$ pfu | 1:$10^2$ serum $10^5$ pfu | 1:$10^2$ serum $10^4$ pfu | 1:$10^2$ serum $10^3$ pfu | 1:$10^2$ serum | |
| C | 1:$10^3$ serum $10^9$ pfu | 1:$10^3$ serum $10^8$ pfu | 1:$10^3$ serum $10^7$ pfu | 1:$10^3$ serum $10^6$ pfu | 1:$10^3$ serum $10^5$ pfu | 1:$10^3$ serum $10^4$ pfu | 1:$10^3$ serum $10^3$ pfu | 1:$10^3$ serum | |
| D | 1:$10^4$ serum $10^9$ pfu | 1:$10^4$ serum $10^8$ pfu | 1:$10^4$ serum $10^7$ pfu | 1:$10^4$ serum $10^6$ pfu | 1:$10^4$ serum $10^5$ pfu | 1:$10^4$ serum $10^4$ pfu | 1:$10^4$ serum $10^3$ pfu | 1:$10^4$ serum | |
| E | 1:$10^5$ serum $10^9$ pfu | 1:$10^5$ serum $10^8$ pfu | 1:$10^5$ serum $10^7$ pfu | 1:$10^5$ serum $10^6$ pfu | 1:$10^5$ serum $10^5$ pfu | 1:$10^5$ serum $10^4$ pfu | 1:$10^5$ serum $10^3$ pfu | 1:$10^5$ serum | |
| F | 1:$10^6$ serum $10^9$ pfu | 1:$10^6$ serum $10^8$ pfu | 1:$10^6$ serum $10^7$ pfu | 1:$10^6$ serum $10^6$ pfu | 1:$10^6$ serum $10^5$ pfu | 1:$10^6$ serum $10^4$ pfu | 1:$10^6$ serum $10^3$ pfu | 1:$10^6$ serum | |
| G | 1:$10^7$ serum $10^9$ pfu | 1:$10^7$ serum $10^8$ pfu | 1:$10^7$ serum $10^7$ pfu | 1:$10^7$ serum $10^6$ pfu | 1:$10^7$ serum $10^5$ pfu | 1:$10^7$ serum $10^4$ pfu | 1:$10^7$ serum $10^3$ pfu | 1:$10^7$ serum | |
| H Phage Control | $10^9$ pfu | $10^8$ pfu | $10^7$ pfu | $10^6$ pfu | $10^5$ pfu | $10^4$ pfu | $10^3$ pfu | Bacteria control | |

BACTERIOPHAGE COMPOSITIONS AND METHODS OF SELECTION OF COMPONENTS AGAINST SPECIFIC BACTERIA

CROSS REFERENCE TO RELATED APPLICATIONS

The present application claims the benefit of U.S. Provisional Patent Application No. 62/353,517 filed Jun. 22, 2016; U.S. Provisional Patent Application No. 62/489,860 filed Apr. 25, 2017 and U.S. Provisional Patent Application No. 62/510,649 filed May 24, 2017 the entire contents of which are incorporated by reference herein.

FIELD OF THE INVENTION

The subject matter of the instant invention relates to methods of compounding compositions comprising bacteriophage effective for treating bacterial infections, including but not limited to, multidrug resistant bacterial infections. The invention also relates to compositions, bacterial diversity sets, and phage libraries prepared according to the methods of the instant invention.

BACKGROUND OF INVENTION

Current global surveillance indicates that multidrug resistant (MDR) bacteria are emerging at an alarming rate. There is also a significant concern regarding the possibility that genetic engineering and synthetic biology may result in the creation of highly virulent microorganisms. In view of the potential threat of rapidly occurring and spreading virulent microorganisms and antimicrobial resistance, alternative clinical treatments against bacterial infection must be sought and developed.

Bacteriophages ("phages") are diverse viruses that replicate within and can kill specific bacterial hosts. The possibility of harnessing lytic phages as an antibacterial was investigated following their initial isolation early in the 20$^{th}$ century, and they have been used clinically as antibacterial agents in some countries with some success. Notwithstanding, phage therapy was largely abandoned in the U.S. subsequent to the discovery of penicillin, and only recently has interest in phage therapeutics been renewed. For example, engineered phages have been used as therapeutic delivery systems e.g., natural phages covalently attached to antibiotics, pathogen-targeted peptide displays on the surface of a phage, and bacteria specific CRISPR (clustered regularly interspaced short palindromic repeats)-Cas systems for silencing antibiotic resistance genes. Components of phage have also been used as antibacterial agents (e.g., cloning phage genes) such as lysozymes, endolysin, and phage tail-associated muralytic lytic enzymes (TAME).

Phages are typically highly specific for a particular bacterial host and thus can be used clinically to target a bacterial pathogen. Unfortunately, however, due to phage-bacterial host specificity, so called broad spectrum phage products against numerous bacterial strains, even of the same pathogenic bacterial species, are difficult to develop; a previously effective phage therapy can quickly become ineffective during clinical treatment as the target bacterial host is eliminated and is naturally replaced by one or more emergent phage-resistant bacterial strains. In fact, pre-existing phage-resistance and/or emergent phage-resistance in a bacterial population is to be expected whenever a phage and a bacterial population interact, and unless steps are taken to also target these resistant mutants in the bacterial population, these mutants will simply be selected-for and will outgrow once the phage eliminate the susceptible fraction of the population. Thus, currently, the clinical usefulness of phage therapy remains limited at best, and there remains a need for improved methods and formulations for using phage as antibacterial agents. Specifically, there remains a need for methods which permit the rapid and reliable compounding of therapeutic compositions comprising one or more phages, wherein said composition is not only custom designed ("personalized") to treat an infection caused by a particular bacterial strain in a subject in need thereof, but is also able to overcome the expected phage-resistant bacterial mutant strains that will outgrow during treatment, so as to allow therapeutic efficacy.

SUMMARY OF THE INVENTION

In a first aspect, the invention relates to a method of compounding a phage cocktail directed against a bacterial pathogen comprising a). constructing a bacterial diversity set comprising diverse strains of the same species as said bacterial pathogen, said constructing comprising collecting a plurality of bacterial isolates of the same species as said bacterial pathogen, analyzing said plurality of bacterial isolates to identify bacterial isolates which are clinically, genotypically and/or metabolically diverse strains of said species of bacterial pathogen, and down selecting said plurality of bacterial isolates to include said clinically, genotypically and/or metabolically diverse strains of said species of bacterial pathogen to create said bacterial diversity set;

b). collecting mixed phages from diverse environmental sources;

c). constructing a Tier 1 archival phage library, said constructing comprising hosting the mixed phages collected in step (b) on one or more of the diverse strains of said species of bacterial pathogen comprising the bacterial diversity set created in step (a) in order to identify and purify lytic phages against strains of said bacterial species, and selecting said lytic phages for the Tier 1 archival phage library;

d). constructing a Tier 2 working phage library, said constructing comprising characterizing the Tier 1 archival phage library constructed in step (c) to identify and exclude phages which demonstrate undesirable and/or toxic characteristics, further screening remaining phages in the Tier 1 working phage library against one or more of the diverse strains of said species of bacterial pathogen comprising the bacterial diversity set created in step (a) to characterize host range of each said remaining phages, and selecting phages free of undesirable and/or toxic characteristics and having desirable host ranges for the Tier 2 working phage library;

e). screening the Tier 2 working phage library constructed in step (d) for individual phages and/or various phage combinations that may be therapeutically effective against the bacterial pathogen, said screening comprising performing phage efficacy assays, wherein said phage efficacy assays comprise growing cultures of said bacterial pathogen with individual phages, and/or various phage combinations from the Tier 2 working phage library, and analyzing bactericidal activity against said bacterial pathogen by said individual phages and/or said various phage combinations in said cultures, wherein a suitable delay in bacterial growth and/or a lack of appearance of phage-resistant bacterial growth in said cultures indicates said individual phages and/or said various phage combinations may be therapeutically effective against the bacterial pathogen; and f). compounding one or more of said individual phages, and/or said various phage combinations, that may be therapeutically effective identified in step (e) to form said phage cocktail.

In a particular embodiment, the bacterial pathogen is multidrug resistant. In another embodiment, the bacterial pathogen is a clinical bacterial isolate causing infection in a subject. In a particular embodiment, the clinical bacterial isolate causing infection in a subject is multidrug resistant. In another embodiment, the plurality of bacterial isolates is clinical bacterial isolates. In a particular embodiment, the clinical bacterial isolates are obtained from bona-fide human infections.

In another embodiment, the plurality of bacterial isolates is analyzed in step (a) to identify said genotypically diverse bacterial strains. In a particular embodiment, the analysis comprises one or more experimental techniques selected from the group consisting of whole genome analysis, targeted sequence analysis, amplicon sequencing analysis, and analysis of restriction fragment length polymorphisms and PCR genotyping by pulse field gel electrophoresis.

In another embodiment, the plurality of bacterial isolates is analyzed in step (a) to identify metabolically diverse bacterial strains. In a particular embodiment, the analysis comprises determining one or more bacterial metabolic criteria selected from the group consisting of antibiotic resistance, ability to utilize various sugars, ability to utilize various carbon sources, ability to grow on various salts, ability to grow in presence or absence of oxygen, and bacterial motility.

In another embodiment, the diverse environmental sources of mixed phages are selected from the group consisting of soil, water treatment plants, raw sewage, sea water, lakes, rivers, streams, standing cesspools, animal and human intestines, and fecal matter.

In another embodiment, the identification and purification of lytic phages in step (c) comprises identifying and purifying phages that produce clear point plaques in classical plaquing assays against one or more of the bacterial strains in the bacterial diversity set created in step (a). In a particular embodiment, all of the bacterial strains in the bacterial diversity set are assayed. In another embodiment, the lytic phages creating clear point plaques are purified using multiple rounds of classical plaque purification techniques.

In another embodiment, the phages which demonstrate undesirable and/or toxic characteristics and are excluded from the Tier 2 library are selected from the group consisting of phages which carry toxin genes or other bacterial virulence factors, phages which possess lysogenic properties and/or carry lysogeny genes, phages which transduce bacterial virulence factor genes or antibiotic resistance genes, phages which carry any antibiotic-resistance genes or can confer antibiotic resistance to bacterial strains, and phages which elicit an inappropriate immune response and/or provoke a strong allergenic response in a mammalian system.

In another embodiment, the phages identified and selected for inclusion in the Tier 2 working phage library have different host range. In a particular embodiment, the phages identified and selected for inclusion in the Tier 2 working phage library are selected from the group consisting of phages having a broad host range and phages having a narrow host range. In a particular embodiment, the Tier 2 working phage library comprises phages with a broad host range and phages with a narrow host range.

In another embodiment, one or more steps of the methods of the present invention are performed using robotics or other high throughput assay. In a particular embodiment, the phage efficacy assay in step (e) is performed using a high throughput assay. In a particular embodiment, the high throughput assay is a liquid assay system.

In another embodiment, the phage efficacy assay in step (e) comprises growing liquid cultures of said bacterial pathogen with said individual phages from the Tier 2 working phage library to detect phages which can cause a desirable delay in bacterial growth.

In another embodiment, the delay in bacterial growth and/or the lack of appearance of phage-resistant bacterial growth in the phage efficacy assay in step (e) is monitored comprising the use of a photometric assay. In particular embodiments, the photometric assay is selected from the group consisting of fluorescence, absorption, and transmission assays. In another particular embodiment, the photometric assay comprises a step wherein an additive is used to cause and/or enhance the photometric signal detection. In a particular embodiment, said additive is tetrazolium dye.

In a particular embodiment, the phage cocktail compounded in step (f) is a synergistic phage cocktail.

In yet another embodiment, the method further comprises rescreening the phage cocktails compounded in step (f) against the Tier 2 working phage library according to step (e) to identify possible additional therapeutically effective phage combinations. In a particular embodiment, the method comprises iteratively rescreening the phage cocktails to identify possible additional therapeutically effective phage combinations. In a particular embodiment, the phages of said additional therapeutically effective phage combinations act synergistically to cause a suitable delay in bacterial growth.

In yet another embodiment, the method further comprises rescreening a phage combination and/or a phage cocktail which does not cause a desirable delay and/or a synergistic delay in bacterial growth, and/or does not cause a lack of appearance of phage-resistant bacterial growth, to identify possible additional phages which may produce a desirable delay and/or a synergistic delay in bacterial growth and/or a lack of appearance of phage-resistant bacterial growth when added to the phage combination and/or the phage cocktail, wherein said rescreening comprises rescreening with one or more individual phages selected from the group consisting of phages in the Tier 2 working phage library, phages in the Tier 1 archival phage library, and new phages isolated from environmental sources.

In a particular embodiment, the method comprises iteratively rescreening the phage combination and/or the phage cocktail which does not cause a desirable delay and/or a synergistic delay in bacterial growth, and/or does not cause a lack of appearance of phage-resistant bacterial growth, with one or more phages from the Tier 1 library, the Tier 2 library, and/or phages from new environmental samples In another embodiment, the method further comprises updating the bacterial diversity set as additional strains of the same species as said bacterial pathogen are identified, and/or updating the Tier 1 archival phage library and/or the Tier 2 working phage library to include additional phages.

In yet another embodiment, the method further comprises purifying each of the phages in the Tier 2 working phage library in large amounts, and/or at high titer and high purity, to facilitate compounding of said phage cocktails.

In additional embodiments, the method further comprises manufacturing phages identified in step (e), and/or the phage cocktails compounded in step (f), on said bacterial pathogen, and/or on laboratory strains, manufacturing strains, and/or domesticated strains of the same species as said bacterial pathogen, to high titer, and purifying to high purity.

In another embodiment, the phage combination identified in step (e) and/or the phage cocktail compounded in step (f) comprises one or more phages that cannot infect said bacterial pathogen, but can infect emergent bacterial strains which arise following infection of said bacterial pathogen by other phages in the phage combination and/or the phage cocktail. In a particular embodiment, said one or more phages that cannot infect said bacterial pathogen act synergistically with one or more phages that can infect said bacterial pathogen to produce said suitable delay in bacterial growth and/or said lack of appearance of phage-resistant bacterial growth. In another particular embodiment, the emergent bacterial strains are less virulent than said bacterial pathogen, regain sensitivity to one or more drugs, and/or display reduced fitness for growth in the subject. In a particular embodiment, the drug is an antibiotic.

In another aspect, the invention relates to a method of compounding a phage cocktail directed against a bacterial pathogen causing infection in a subject comprising screening the bacterial pathogen against an established Tier 2 working phage library. In a particular embodiment, the method further comprises screening a Tier 1 archival phage library and/or new environmental samples against said bacterial pathogen to identify new phages for inclusion in the phage cocktail. In a further embodiment, the new phages are characterized and included in the established Tier 2 working phage library.

In another aspect, the invention relates to a phage cocktail compounded according to the methods of the instant invention. In a particular embodiment, the phage cocktail is a synergistic phage cocktail.

In another aspect, the invention relates to a bacterial diversity set created according to the methods of the instant invention.

In another aspect, the invention relates to a phage library created according to the methods of the instant invention. In a particular embodiment, the phage library is a Tier 1 archival phage library. In another embodiment, the phage library is a Tier 2 working phage library.

In yet another aspect, the invention relates to a method of treating a bacterial infection in a subject in need thereof comprising administering to the subject an effective amount of a pharmaceutical composition comprising a phage cocktail compounded according to the methods of the instant invention. In a particular embodiment, the bacterial infection to be treated is selected from the group consisting of wound infections, post-surgical infections, and systemic bacteremias.

In various additional aspects, the invention relates to a phage cocktail comprising a therapeutically effective phage combination for use in treating a bacterial infection in a subject in need thereof; use of a phage cocktail comprising a therapeutically effective phage combination for treating a bacterial infection in a subject in need thereof; and use of a phage cocktail comprising a therapeutically effective phage combination in the manufacture of a medicament for treating a bacterial infection in a subject in need thereof.

BRIEF DESCRIPTION OF THE DRAWINGS

FIG. 1 depicts the general possible plate design for assessing the infectivity of phage strains versus a given bacterial host strain described in Example 1. Media with a tetrazolium dye mixture is added to all wells. Separate phage strains are then added in at column 1 to a total of $10^7$ pfu per well, which will produce an approximate 1000 Multiplicity of Infection (MoI). The phage from column 1 will then be serially diluted 10-fold to column 7 to a final MoI of 0.001. Control wells are located in columns 8 through 10 to assess sterility of the media and phage. Additionally column 10 provides for an unadulterated bacterial growth curve for the host strain. Columns 11 and 12 serve as wells to be used for diluting the bacterial host strain to achieve the proper inoculating concentration of $10^4$ cfu per well.

FIG. 13 depicts the clinical isolates harvested before and after phage therapy in the case report described in Example 5.

FIG. 14 depicts the phage therapy (doses/day) of the Navy cocktail phages utilized in the personalized phage therapy described in Example 5. Phage therapy (IV.) started on Mar. 17, 2016.

FIG. 15A-15H depict the activity of phage cocktails ϕPC and Navy phage cocktail 1 ("Abϕ MIX") against serial isolates of *A. baumannii* isolated from intra-abdominal drains before bacteriophage therapy (strain TP1) (FIG. 15A and FIG. 15E), and four days (Strain TP2; FIG. 15B and FIG. 15C) and eight days (Strain TP3; FIG. 15F and FIG. 15G) after initiation of bacteriophage therapy. FIG. 15D shows the activity of a second-generation phage cocktail directed at the TP3 *A. baumannii* strain. FIG. 15H shows the additive activity of the Navy phage cocktail 1 ($10^5$ pfu) and a sub-lethal concentration of minocycline (0.25 µg/mL) against *A. baumannii* strain TP3. The $IC_{50}$ of *A. baumannii* strain TP3 to minocycline by ETEST was 4 µg/mL.

In FIG. 20A, the mixed phages demonstrate additive effect; the isobologram on the right is a straight line. Synergism is demonstrated in FIG. 20B, where isobologram is concave. Antagonistic interactions in FIG. 20C result in a convex isobologram.

FIG. 24 depicts the experimental design of a "checkerboard assay" to evaluate the type of interaction that might occur between a phage cocktail and a bacterial pathogen in the presence of neutralizing antibodies present in a subject's serum as discussed in Example 6.

Figure 25:
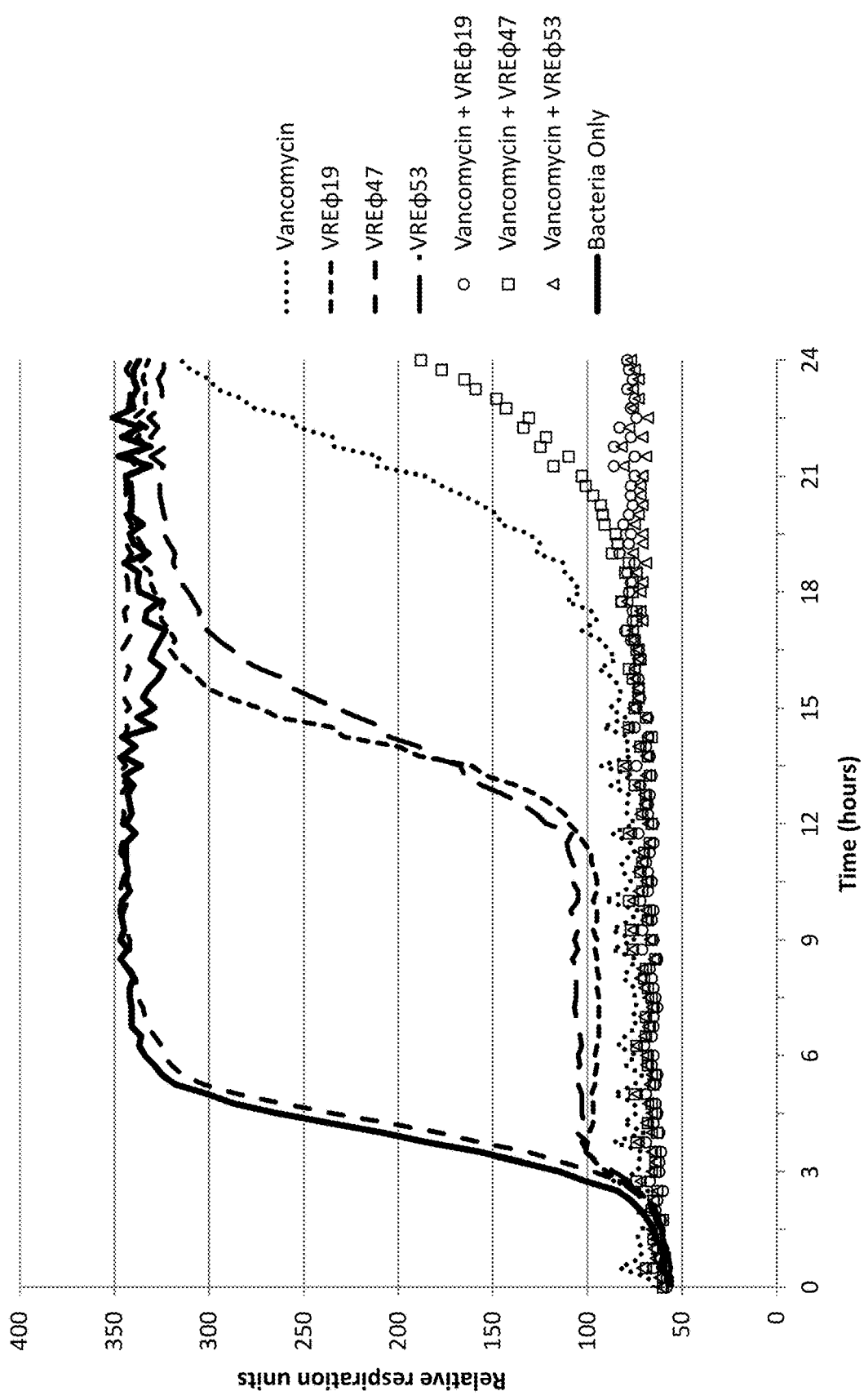

FIG. 25 depicts vancomycin and phage synergy against vancomycin-resistant *Enterobacter faecalis* discussed in Example 4.

DETAILED DESCRIPTION

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made at are at 25° C. and normal pressure unless otherwise designated. The present invention can "comprise" (open ended) or "consist essentially of" the components of the present invention as well as other ingredients or elements described herein. As used herein,"comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a phage cocktail" can mean at least one phage cocktail, as well as a plurality of phage cocktails, i.e., more than one phage cocktail. As understood by one of skill in the art, the term "phage" can be use to refer to a singe phage or more than one phage.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

It is contemplated herein that in order to get better clinical results using phage therapy, more creative ways to compound therapeutic phage cocktails are needed. As discussed briefly above, the tendency for phage resistant bacterial strains to emerge during phage therapy has posed a severe limitation in the potential use of phage to treat bacterial infections, including MDR bacterial infections. Typically, an infecting bacterial strain can change significantly in response to host and phage selection pressures during an infection, and thus an essentially clonal bacterial infection can fragment into a cohort or cloud of strains that are closely related but phenotypically and/or genotypically distinct from each other and the parent strain of the infection. Thus, although it may be possible using prior art methods to compound a phage cocktail that can kill a target bacterial pathogen, typically, the resulting phage cocktail will not be clinically effective indefinitely because of changes which develop in the population of the bacterial pathogen which block phage infectivity. In fact, low frequency phage resistance mutants are likely present in the infectious bacterial population at the outset. The failure of prior art phage therapy is thus revealed when these emergent and/or preexisting mutants outgrow following phage therapy. In addition, prior art methods of compounding phage cocktails are extremely limited by the standard practice of relying only on phages with detectable activity against (and thus known to infect) the particular targeted clinical bacterial pathogen infecting the subject.

It is contemplated herein that in order to compound effective anti-bacterial phage cocktails that can be used to eradicate a bacterial infection, one has to anticipate the emerging changes in the bacterial pathogen. To this end, the methods of the invention comprise creating and employing well characterized phage libraries which can be used to rapidly and reliably compound personalized phage cocktails that provide the greatest chance of getting complete coverage and efficacy against the entire population of an infectious bacterial pathogen. Significantly, in contrast to preexisting methods, creating and screening pre-characterized diverse phage libraries according to the methods of the instant invention permits the rapid and reliable identification not only of phages that can have a therapeutic effect on a bacterial pathogen, but also phages that work synergistically in combination to drive the targeted bacterial population to near extinction. Surprisingly, the methods of the instant invention also permit the creation of therapeutic phage cocktails which include phages that when tested individually have undetectable activity against the targeted bacterial pathogen, but are important to the overall therapeutic efficacy of the cocktail; the activity of these critical phages is only revealed and detectable in the context of the cocktails compounded through the use of the methods of the instant invention. Perhaps such phages target low frequency preexisting mutants in the population of the bacterial pathogen, and/or mutants that emerge due to the activity of other phages in the cocktail; notably, the particular mechanism of action of such phage cocktails need not be understood in order to compound them or achieve therapeutic efficacy with them.

By identifying the therapeutic utility of phages which on their own have no detectable activity against a targeted bacterial pathogen, and permitting using these phages to build synergistic cocktails that greatly reduce, delay, or even prevent phage resistance to the synergistic cocktail, the methods of the instant invention are a significant improvement over prior art methods. To date, the applicant is unaware of any other known methods beside the instant invention to reliably find synergistic cocktails, and synergistic cocktails that include phages which on their own have no detectable activity against the targeted bacterial pathogen. Indeed, the invention allows the identification of extremely rare and unique combinations of phages that can work synergistically against numerous clinical strains of the same species of bacterial pathogen starting with no a priori knowledge of phage susceptibility. By not needing to know the mechanism of the synergy, the disclosed methods are broadly applicable to numerous bacterial species.

In view of the foregoing, the method of compounding therapeutically effective phage cocktails disclosed herein can be deemed counterintuitive since the cocktails may comprise phages that can exclusively infect low frequency emergent and/or pre-existing resistant mutants in a bacterial population, and not the dominant parent bacterial strain, i.e., one cannot detect the ability of these phages to infect the targeted bacterial pathogen using current and/or classical techniques, and their contribution to the therapeutic efficacy of a synergistic cocktail can only be detected in the context of the synergistic cocktail via the instant invention used to compound said synergistic cocktail. If these low frequency mutants are not also targeted, there is a possibility that these mutants can outgrow following phage therapy developed with current and/or classical methods, resulting in a therapeutic failure. Thus, in this respect, the therapeutic phage cocktail prepared according to the methods of the instant invention can provide a synergistic bactericidal effect; i.e., the unique combination of phages in the cocktail target and kill even undetectable segments of the infectious bacterial population, producing an overall therapeutic effect that is greater than the therapeutic effect that would have been produced had each phage been used individually to treat the subject's infection, or if a cocktail had been developed via current and/classical methods that omit the phages that are both required for overall therapeutic efficacy of a synergistic cocktail and themselves have no detectable activity. Importantly, the method allows monitoring the effect of a single phage or multiple phages on bacterial growth in real time. Thus, it is contemplated herein that the methods of the invention are a significant improvement over prior art methods that inevitably fail to identify potential therapeutic phages which only have a detectable activity in the context of a synergistic cocktail made according to the methods of the instant invention.

Thus, in contrast to prior art methods of compounding phage cocktails, it is contemplated herein that the methods of the instant invention provide a new way to intelligently, efficiently, and reliably create phage cocktails compounded to comprise phages which can infect not only the bacterial isolate used to design it, but also the emergent and/or pre-existing resistant bacterial strains that would otherwise outgrow during phage therapy. This manner of cocktail is identified by screening a well characterized diverse phage library and detecting synergistic bactericidal activity, according to the methods detailed below. Accordingly, the methods of the instant invention permit the compounding of a wide variety of unique, therapeutically effective phage cocktails on a case-by-case basis; specifically compounded for individual target bacterial pathogens. Specifically, in a particular embodiment, the methods disclosed herein can be used to generate personalized bacteriophage cocktails against clinically relevant MDR bacterial pathogens.

In a particular embodiment of the invention, the infectious bacterial strain(s) ("bacterial pathogen") is isolated from the patient and screened against a pre-existing characterized library of phages. The screening methodology then serves as a reliable pipeline that allows for the rapid formulation of personalized combinations of phages (ideally, including synergistic cocktails) that can effectively target bacterial pathogens, including MDR pathogens. Thus, as contemplated herein, these personalized cocktails are tailored to specifically treat a discrete infection, and the host range of the cocktail is specifically suited to cover the infection. The combination of phages used in these personalized cocktails may provide synergistic effects, and not only target the parent strain of an infection but also resistant sub-populations that pre-exist or emerge as a result of the phage therapy. Additionally, as discussed in detail below, it is further contemplated herein that the formulation of a particular personalized cocktail according to the methods of the instant invention may have therapeutic utility beyond the original patient for whom the cocktail was generated.

The methods of compounding phage cocktails disclosed herein also provide the advantage that, unlike current use of antibiotic therapies, pathogenic bacteria in circulation will not have repeated exposure to a single treatment and thus will not have the opportunity to evolve broad resistance to the treatment.

Thus, in a first aspect, the invention relates to a method of compounding a phage cocktail directed against a bacterial pathogen comprising a). constructing a bacterial diversity set comprising diverse strains of the same species as said bacterial pathogen, said constructing comprising collecting a plurality of bacterial isolates of the same species as said bacterial pathogen, analyzing said plurality of bacterial isolates to identify bacterial isolates which are clinically, genotypically and/or metabolically diverse strains of said species of bacterial pathogen, and down selecting said plurality of bacterial isolates to include said clinically, genotypically and/or metabolically diverse strains of said species of bacterial pathogen to create said bacterial diversity set;

b). collecting mixed phages from diverse environmental sources;

c). constructing a Tier 1 archival phage library, said constructing comprising hosting the mixed phages collected in step (b) on one or more of the diverse strains of said species of bacterial pathogen comprising the bacterial diversity set created in step (a) in order to identify and purify lytic phages against strains of said bacterial species, and selecting said lytic phages for the Tier 1 archival phage library;

d). constructing a Tier 2 working phage library, said constructing comprising characterizing the Tier 1 archival phage library constructed in step (c) to identify and exclude phages which demonstrate undesirable and/or toxic characteristics, further screening remaining phages in the Tier 1 archival phage library against one or more of the diverse strains of said species of bacterial pathogen comprising the bacterial diversity set created in step (a) to characterize host range of each said remaining phages, and selecting phages free of undesirable and/or toxic characteristics and having desirable host ranges for the Tier 2 working phage library;

e). screening the Tier 2 working phage library constructed in step (d) for individual phages and/or various phage combinations that may be therapeutically effective against the bacterial pathogen, said screening comprising performing phage efficacy assays, wherein said phage efficacy assays comprise growing cultures of said bacterial pathogen with individual phages, and/or various phage combinations from the Tier 2 working phage library, and analyzing bactericidal activity against said bacterial pathogen by said individual phages and/or said various phage combinations in said cultures, wherein a suitable delay in bacterial growth and/or a lack of appearance of phage-resistant bacterial growth in said cultures indicates said individual phages and/or said various phage combinations may be therapeutically effective against the bacterial pathogen; and f). compounding one or more of said individual phages, and/or said various phage combinations, that may be therapeutically effective identified in step (e) to form said phage cocktail.

As contemplated herein, the methods of the instant invention permit rapidly compounding a therapeutic composition against any particular bacterial pathogen that may be present in a clinical isolate obtained from a subject. Thus, the methods of the instant invention provide the ability to custom design a therapeutic composition that is "personalized" for an individual patient. As one of skill in the art will appreciate, the term "compounding" as used herein comprises the creation of a particular composition comprising one or more and, particularly, a plurality of phages which is designed to address the unique clinical needs of a subject. While not necessary, in a particular embodiment, it is contemplated herein that once a phage cocktail is compounded, the cocktail may be grown on the patient's clinical isolate as a test for efficacy prior to administration to the subject.

As used herein a "mixed phage" refers to an environmental sample containing more than one phage.

A "phage cocktail", "therapeutic phage cocktail", "therapeutically effective phage cocktail" and like terms as used herein are understood to refer to a composition comprising one or more, and particularly, a plurality of phages compounded according to the methods of the instant invention which can provide a clinically beneficial treatment for a bacterial infection when administered to a subject in need thereof. Specifically, therapeutically effective phage cocktails of the instant invention are capable of infecting the infective parent bacterial strain as well as the emerging and/or pre-existing resistant bacterial strains that would otherwise outgrow during phage therapy. Notably, individually, the phages used for the cocktail may not infect the parent bacterial strain in any detectable way, and only provide clinical utility and therapeutic efficacy in the context of a synergistic cocktail identified using the methods of the instant invention. As described in more detail below, a therapeutic phage cocktail of the instant invention causes a desirable delay in bacterial growth and/or a lack of appearance of phage-resistant bacterial growth. In other various embodiments, a phage cocktail compounded according to the methods of the invention that displays therapeutic efficacy may or may not show a synergistic delay in bacterial growth, may show varying degrees of synergistic delay in bacterial growth, and/or may show a lack of appearance of phage-resistant bacterial growth. One of skill in the art will appreciate that the term, "varying degrees of synergistic delay in bacterial growth" includes but is not limited to, only a modest or minimal synergistic delay in bacterial growth.

As understood herein, the term "synergy" is familiar to one of skill in the art, i.e., a combined effect that is greater than the sum of individual effects. Thus, with regard to the methods of the instant invention, the terms, "synergy", "synergistic delay", and like terms refer to a bacterial growth hold time (i.e., demonstrated delay in bacterial growth) that is greater than the simple addition of each individual phage's observed hold-time/growth delay. Thus, one of skill in the art will appreciate that, with regard to a "synergistic phage cocktail", the synergistic therapeutic effect observed is a therapeutic effect greater than the demonstrated sum of the individual effects of the phages in the cocktail; i.e. the delay in bacterial growth produced by the phage combination identified in step (e) and/or the phage cocktail compounded in step (f) is greater than the delay in bacterial growth produced by each individual phage in said phage combination/cocktail, and greater than the addition of the delays in bacterial growth produced by each of the individual phages of said combination/cocktail.

Similarly, with regard to a synergistic combination of phage(s) and an antibiotic, it is understood that the synergistic therapeutic effect is a therapeutic effect greater than the demonstrated sum of the effect of the phage(s) and the antibiotic on bacterial growth hold times.

It is contemplated herein that synergistic cocktails of the instant invention can extend growth hold time long enough to have therapeutic efficacy. In addition, synergistic cocktails may prevent any detectable bacterial growth for the entire time course of the assay, e.g., 18 hours or more. Thus, in some cases, a synergistic response can result in a near extinction event, i.e., no bacterial growth occurs at all after exposure to the synergistic cocktail. It is understood herein that such cocktails may display a desirable synergistic delay.

As understood herein, a "subject", "subject in need thereof" and like terms encompass any organism, e.g., any animal or human, that may be suffering from a bacterial infection, particularly an infection caused by a MDR bacteria.

As understood herein, "diverse strains of the same species as said bacterial pathogen" refers to unique strains of the same bacterial pathogen infecting the individual in need of treatment. This includes, e.g., a group of bacteria which belong to the same species but may vary considerably in their ability to produce productive infections, disease manifestations and pathogenesis in any living organism. The genotypic and phenotypic nature of this group of bacteria can vary considerably from each other. Indeed, it is contemplated herein that each of these unique strains will be selected for the bacterial diversity set so as to maximize genetic diversity within the collection, which in turn will maximize the available bacterial surface phenotypes and potential phage receptors present in aggregate within the bacterial diversity set, which in turn will maximize the diversity of the phages isolated from the environment when using this diversity set for phage isolation according to the methods of the instant invention.

As used herein, a "clinical isolate" is a pathogenic bacteria harvested from human or animals during course of pathogenesis or gradual progression of a specific disease, e.g., an infectious bacterial pathogen that was isolated from a bona-fide human infection.

As understood herein, a "bona-fide human infection" refers to a bacterial infection, which produces pathogenesis in humans, including, e.g., a symptomatic infection that requires medical intervention, including culturing the infectious bacterial strain.

Any type of bacterial contamination may be treated using the methods and compositions of the instant invention. Particularly, bacterial infections to be treated using the compositions and methods of the instant invention may include any infection by a bacterial pathogen that poses a health threat to a subject. In a particular embodiment, bacteria for treatment according to the methods of the present invention include, but are not limited to, multidrug resistant bacterial strains. As understood herein, the terms, "multidrug resistant", "multi drug resistant", "multi drug resistance", "MDR" and like terms may be used interchangeably herein, and are familiar to one of skill in the art, i.e., a multidrug resistant bacteria is an organism that demonstrates resistance to multiple different antibacterial drugs, e.g., antibiotics; and more specifically, resistance to multiple different classes of antibiotics. It is understood herein that bacterial infections to be treated comprise bacteria in biofilm and/or planktonic growth modes.

Bacteria that may be treated include, but are not limited to the "ESKAPE" pathogens (*Enterococcus faecium, Staphylococcus aureus, Klebsiella pneumonia, Acinetobacter baumannii, Pseudomonas aeruginosa*, and *Enterobacter* sp), which are often nosocomial in nature and can cause severe local and systemic infections. Specifically, these include, e.g., methicillin-resistant *Staphylococcus aureus* (MRSA); vancomycin-resistant *Enterococcus faecium* (VRE); carbapenem-resistant *Klebsiella pneumonia* (NDM-1); MDR-*Pseudomonas aeruginosa*; and MDR-*Acinetobacter baumannii*.

Among the ESKAPE pathogens, *A. baumannii* is a Gram-negative, encapsulated, opportunistic pathogen that is easily spread in hospital intensive care units. For example, *A. baumannii* infections are typically found in the respiratory tract, urinary tract, and wounds. Many *A. baumannii* clinical isolates are also MDR, which severely restricts the available treatment options, with untreatable infections in traumatic wounds often resulting in prolonged healing times, the need for extensive surgical debridement, and in some cases the further or complete amputation of limbs. Notably, blast-related injuries in military populations are associated with significant tissue destruction with concomitant extensive blood loss and therefore these injuries are at high risk for infectious complications. One of skill in the art will appreciate that given the ability for *A. baumannii* and other MDR ESKAPE pathogens to colonize and survive in a host of environmental settings, there is an urgent need for new therapeutics against these pathogens.

One of skill in the art will appreciate that bacterial infections to be treated using the compositions and methods of the instant invention include any type of bacterial infection in a subject. These include, for example, not only infections that may be associated with wounds, but also non-wounds, e.g., infections that might arise without underlying trauma or any other type of bodily injury, traumatic or otherwise. These infections may include local infections, e.g. a respiratory infection or an internal or external abscess that progresses to a systemic infection. Infections that may be treated according to the methods of the instant invention also include infected surgical wounds, e.g., "post-surgical" infections that may arise in a subject after and/or resulting from a surgical procedure or any other kind of medical or surgical treatment or intervention, e.g., a catheterization procedure, or surgical implantation of a medical device, prosthetic, or other foreign object into a subject, etc. One of skill in the art will appreciate the myriad other therapeutic uses for the personalized phage cocktails of the instant invention given that the personalized cocktails can be administered both topically and systemically, e.g. via IV or IM injections, or injected into the peritoneal cavity. Thus the types of infections that can be treated also include, for example, infections associated with and/or treatment for burns, ulcers, systemic bacteremia, septicemia, inflammatory urologic disease, infections associated with cystic fibrosis, abscesses, empyema, suppurative lung diseases, as well as infections in other internal organs, including but not limited to infections in the liver, spleen, kidney, bladder, lungs etc.

Further embodiments include a method of generating a Tier 2 working phage library, wherein said method comprises (a) obtaining a Tier 1 archival phage library comprising a plurality of individually isolated phage having bactericidal activity against a bacterial pathogen; (b) screening the Tier 1 archival phage library to identify phage containing undesirable, deleterious and/or toxic characteristics; (c) generating a Tier 2 working phage library from the Tier 1 archival phage library by excluding those phage identified in (b) from the Tier 2 working phage library. The Tier 2 working phage library can either comprises phage with a narrow, broad, or a narrow and broad host range.

Further preferred embodiments include a method of generating a bactericidal composition comprising phage to treat a bacterial infection in a patient, wherein the method comprises: (a) contacting a bacterial pathogen isolated from a patient against a plurality of individually isolated phage; (b) identifying one or more phage having bactericidal activity against the bacterial pathogen; (c) growing up the phage identified in (b), wherein the phage is grown in media comprising the bacterial pathogen isolated from the patient; (d) purifying the phage produced (c); and (e) generating a bactericidal composition comprising the purified phage obtained in (d).

Other preferred embodiments include a method of generating a bactericidal composition comprising phage to treat a bacterial infection in a patient, wherein the method comprises: (a) contacting a bacterial pathogen isolated from a patient against a plurality of individually isolated phage; (b) identifying one or more phage having bactericidal activity against the bacterial pathogen; (c) generating the bactericidal composition by retrieving the phage identified in (b) from previously amplified stocks of purified phage.

Other preferred embodiments include a method of generating a bactericidal composition comprising phage to treat a bacterial contamination in an environment, wherein the method comprises: (a) contacting a bacterial pathogen isolated from an environmental sample against a plurality of individually isolated phage; (b) identifying one or more phage having bactericidal activity against the bacterial pathogen; (c) growing up the phage identified in (b), wherein the phage is grown in media comprising the bacterial pathogen isolated from the environmental sample; (d) purifying the phage produced (c); and (e) generating a bactericidal composition comprising the purified phage obtained in (d).

Other preferred embodiments include a method of generating a bactericidal composition comprising phage to treat a bacterial contamination in an environment, wherein the method comprises: (a) contacting a bacterial pathogen isolated from an environmental sample against a plurality of individually isolated phage; (b) identifying one or more phage having bactericidal activity against the bacterial pathogen; (c) generating the bactericidal composition by retrieving the phage identified in (b) from previously amplified stocks of purified phage.

In any of these embodiments, the contacting step can be performed in a 96 well plate. Additionally, in any of these embodiments, one or more steps of said method can be performed using robotics or other high throughput assays. For example, the high throughput assay can be a liquid assay system.

In any of these embodiments, the bactericidal activity can be monitored by a photometric assay. Examples of such photometric assays include, but are not limited to fluorescence, absorption, or transmission assays. Moreover, the photometric assay may comprise a step wherein an additive is used to cause and/or enhance the photometric signal detection. One preferred example of such additive is tetrazolium dye.

In further preferred embodiments, the method further comprises screening the plurality of individually isolated phage for phage combinations which produce a synergistic increase in bactericidal activity. Examples of bactericidal activity include but are not limited to bacterial lysis, delay in bacterial growth, or a lack of appearance of phage-resistant bacterial growth. In further embodiments, bactericidal activity can be measured by: (a) phage that can generate clear point plaques on the bacterial sample; (b) phage that demonstrate lytic characteristics using a rapid streak method on a plate; (c) bacterial lysis of at least 0.1, at least 0.2, at least 0.3, at least 0.4, at least 0.5, or between 0.1-0.5 $OD_{600}$ absorbance difference in turbidity with Small or Large Batch assays; (d) delay in bacterial growth of at least 0.1, at least 0.125, at least 0.15, at least 0.175, at least 0.2, or at between 0.1-0.2 $OD_{600}$ absorbance difference in turbidity in bacteriostatic phage infections; (e) a lack of appearance of phage-resistant bacterial growth for at least 4 hours, at least 5 hours, at least 6 hours, at least 7 hours, or in between 4-6 hours post-infection; (f) reduced growth curves of surviving bacteria after phage infection for at least 4 hours, at least 5 hours, at least 6 hours, at least 7 hours, or in between 4-6 hours in the Host Range Quick Test; or (f) a prevention or delay of at least 50, at least 75, at least 100, at least 125, at least 150, at least 175, at least 200, or between 50-200 relative respiration units in tetrazolium dye-based color change from active bacterial metabolism using the Omnilog bioassay of phage-infected bacteria from the Host Range Quick Test.

Moreover, in any of the preferred embodiments, the plurality of individually isolated phage can be prescreened for undesirable, deleterious and/or toxic characteristics. Additionally, those phage having such undesirable, deleterious and/or toxic characteristics can be excluded from the plurality of individually isolated phage. Examples of such undesirable, deleterious and/or toxic characteristics include, but are not limited to phage which carry toxin genes, phage which possess lysogenic properties and/or carry lysogeny genes, phage which can transduce bacterial virulence factor genes or antibiotic resistance genes different from factors already present in the patient, phage which carry any antibiotic-resistance genes or can confer antibiotic resistance to bacterial strains, and phage which elicit an antagonistic immune response and/or provoke a strong allergenic response in a mammalian system.

In any of the embodiments, the plurality of individually isolated phage can be obtained from diverse environmental sources, including soil, water treatment plants, raw sewage, sea water, lakes, rivers, streams, standing cesspools, animal and human intestines or fecal matter, organic substrates, biofilms, or medical/hospital sources. Moreover, the bacterial pathogen can comprise (a) a plurality of strains of the same species of said bacterial pathogen; (b) clinically, genotypically and/or metabolically diverse strains of said species of bacterial pathogen; and/or (c) be a multi-drug resistant pathogen. Moreover, the plurality of strains can be down selected to generate a bacterial diversity set of strains comprising clinically, genotypically and/or metabolically diverse strains of said species of bacterial pathogen. Examples of such metabolically diverse strains include, but are not limited to antibiotic resistance, ability to utilize various sugars, ability to utilize various carbon sources, ability to grow on various salts, ability to grow in presence or absence of oxygen, or bacterial motility. In preferred embodiments, the plurality of individually isolated phage can comprise lytic phage.

In the preferred embodiments, the purified phage can be purified by a purification technique, such as, for example, (a) cesium chloride gradient ultracentrifugation; (b) octanol washes; (c) differentiation filtration; (d) column chromatography; or (e) phase partition chromatography.

In preferred embodiments, the cesium chloride level in the bactericidal composition is less than 50 ug/L, less than 40 ug/L, less than 30 ug/L, less than 25 ug/L, less than 20 ug/L, less than 19 ug/L, less than 18 ug/L, less than 17 ug/L, less than 16 ug/L, less than 15 ug/L, less than 14 ug/L, less than 13 ug/L, less than 12 ug/L, less than 11 ug/L, less than 10 ug/L. Moreover, in further preferred embodiments, the endotoxin in the bactericidal composition is less than 500 Units per mL, 450 Units per mL, 400 Units per mL, 375 Units per mL, 350 Units per mL, 325 Units per mL, 300 Units per mL, 275 Units per mL, 250 Units per mL, 225 Units per mL, or 200 Units per mL.

In other preferred embodiments, the minimal burst size in the bactericidal composition is less than 200, less than 175, less than 150, less than 140, less than 130, less than 120, less than 110, less than 100, less than 90, less than 80, less than 70, less than 60, or less than 50.

Other embodiments include using the Tier 2 working phage library produced by any of the methods described herein to obtain a plurality of individually isolated phage. These individually isolated phage can then be used to generate bactericidal compositions. These bacterial compositions can comprise a mixture of different phage identified by any one the methods described above. In preferred embodiments, the mixture of phage produces a synergistic increase in bactericidal activity.

Any of these compositions described herein can be used to treat either a bacterial infection in a patient; or bacterial contamination in an environment. In preferred embodiments, the patient is a mammal, and even more preferably, the mammal is a human. In other preferred embodiments, the mammal is a murine, a simian, a farm animal, a sport animal, and a pet, including, but not limited to a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), or an ape (e.g. gorilla, chimpanzee, orangutan, gibbon).

The methods described herein can be used to decontaminate the environment. Examples of such environments, include but is not limited to oil rigs, medical stents, soil, water treatment plants, raw sewage, sea water, lakes, rivers, streams, standing cesspools, animal or human intestines or fecal matter, organic substrates, biofilms, or medical/hospital sources.

Bacterial "Diversity Set" Construction:

The methods of the present invention comprise assembling a "diversity set" of isolated strains ("isolates") of a single bacterial pathogen, and particularly, isolates that are clinically relevant. In a particular embodiment, the diversity set comprises clinically relevant MDR strains of a single bacterial pathogen. These isolates may be obtained from a variety of sources, e.g., pre-existing repositories of clinical bacterial isolates, as well as from contemporary and/or recent human or animal bacterial infections, including: topical, local, or systemic infections recently cultured. In a particular embodiment, clinical isolates of MDR strains of a single bacterial pathogen are collected from these sources. These isolates may be taken from bona-fide human infections and thus the diversity set represents a collection of bona-fide human pathogens that have caused actual infections.

This large collection of clinically relevant MDR strains of the same species as the targeted bacterial pathogen is then down-selected to comprise a collection of strains that are as diverse from each other as possible. One of skill in the art will appreciate that the down-selection of bacterial strains can be performed using a variety of conventional methods appropriate for characterizing the biological nature of bacteria. For example, the clinical isolates may be analyzed to identify genotypically diverse bacterial strains using a variety of manual as well as automated conventional methods. Such experimental techniques are familiar to one of skill in the art and include, but are not limited to, employing whole genome and/or targeted partial sequence analysis to identify diverse strains. Characterizing restriction fragment length polymorphisms (RFLP) by pulse field gel electrophoresis (PFGE) may also be used to characterize bacterial strains. In addition, PCR-based genotyping may be used. Bacterial serotyping may also be performed using a variety of conventional methods. Characterizing the strains by phage typing may also be used. In a particular embodiment, the analysis may comprise one or more experimental techniques including but not limited to whole genome analysis, targeted sequence analysis, amplicon sequencing analysis, and analysis of restriction fragment length polymorphisms and/or PCR genotyping by pulse field gel electrophoresis.

In addition, the plurality of clinical isolates may also be analyzed using conventional methods to identify metabolically diverse bacterial strains. A variety of conventional or classical microbiological techniques, media, and other reagents may be employed to perform the indicated analyses, including but not limited to manual techniques as well as automated systems familiar to one of skill in the art, e.g., the BD PHOENIX Automated Microbiology System (Becton, Dickinson and Co., Franklin Lakes, N.J.) In a particular embodiment, the methods of analyzing bacterial metabolic criteria for diversity set down-selection used in the methods of the instant invention are familiar to one of skill in the art, and include but are not limited to, one or more methods selected from the group consisting of antibiotic resistance, ability to utilize various sugars, ability to utilize various carbon sources, ability to grow on various salts, ability to grow in presence or absence of oxygen, ability to grow at various temperatures, and bacterial motility. The types of antibiotics, various sugars, carbon sources, salts, as well as other types of biological features useful for assessing metabolic criteria of bacteria, are familiar to one of skill in the art. Such metabolic analyses may be performed alone or in conjunction with genetic analyses discussed above.

It is understood herein that bacterial diversity set construction is an iterative process that may be continuously updated, e.g., as MDR strains drift in and out of clinical relevance. Accordingly, in a particular embodiment, it is contemplated herein that the temporal requirements for diversity set updates may comprise more than one reformulation per year, e.g. an outbreak or the sudden appearance of a new clinically relevant MDR bacterial strain may require its isolation and addition to the diversity set. Alternatively, if the diversity set contains one or more bacterial strains that are no longer observed as clinically problematic, they can be removed from the diversity set.

The goal of bacterial diversity set construction is to assemble a manageable number of clinically relevant bacterial strains that are as dissimilar from each other as possible while accurately representing the current clinical burden of bacterial pathogens, including but not limited to MDR bacterial strains. Thus, a down-selected diversity set may comprise any number of bacterial isolates. For example, it is contemplated that the diversity set may comprise from about 75-125 unique bacterial strains. It is contemplated herein that, in a particular embodiment, a manageable number of strains may be approximately 100 strains, but may be more or less without limitation.

It is contemplated that the bacterial diversity set is as close to a diverse and current representation of the clinical bacterial burden as possible. Thus, a current bacterial pathogen of interest is represented by the bacterial diversity set. The diversity set is also used to isolate phages and to build a tiered characterized phage library, harvested and isolated from a variety of diverse environmental sources. Thus, this tiered phage library can be prepared in advance using the bacterial diversity set, and will contain phages that may infect the bacterial pathogen of interest. As described in detail below, the tiered phage library is a reagent that is screened against said particular bacterial pathogen of interest in order to develop a therapeutic phage cocktail against said bacterial pathogen.

Tier 1 Archival Phage Library Construction:

For the preparation of a "Tier 1 Archival Phage Library", mixed phages are harvested from a variety of diverse environmental sources and then hosted on one or more strains of bacteria from the bacterial diversity set in order to identify and purify lytic phages capable of infecting members of the bacterial diversity set. As understood herein, "lytic" phages can generate clear plaques when plated on the diverse bacterial strains. Lytic phages may be identified and purified using a variety of methods familiar to one of skill in the art, e.g., using classical phage isolation and plaque purification methods. For example, in one embodiment, identifying and purifying lytic phage in step (c) of the method described herein comprises identifying and purifying phages that produce clear point plaques in classical plaquing assays against one or more, or up to all, of the bacterial strains in the bacterial diversity set created in step (a) of the method. In another embodiment, the lytic phages creating clear point plaques may be purified using multiple rounds of classical plaque purification techniques. As used herein, the terms "classical plaquing assays" and "classical plaque purification techniques" are conventional methods familiar to one of skill in the art. See, e.g., Sambrook, J., E. F. Fritsch and T. Maniatis (1989). "Molecular Cloning: A Laboratory Manual. 2nd ed." Cold Spring Harbor Press, Cold Spring Harbor, N.Y.

As understood herein, harvesting mixed phages from a variety of "diverse environmental sources" refers to obtaining phage-rich samples from a wide variety of different places where phage may be found in the environment, including, but not limited to, any place where bacteria are likely to thrive. In fact, phages are universally abundant in the environment. The primary factors affecting the successful isolation of such phages are the availability of a robust collection of clinically relevant bacterial pathogens to serve as hosts, e.g. the bacterial diversity set, and access to diverse environmental sampling sites rich in phages. With these conditions met, simple screening methods can be employed to rapidly isolate and amplify lytic phages specific to bacterial pathogen(s) of interest, and their therapeutic potential can be investigated.

As used herein, "new phages", "new phages isolated from environmental sources" and like terms refer to additional phages which have yet to be included and assayed as part of a Tier 1 or Tier 2 library. Such phages can be acquired by obtaining new environmental samples comprising phages from diverse environmental sources, including new environmental samples which comprise uncharacterized "wild phages", as well as new samples of additional characterized phages that may be obtained from other laboratories or commercial vendors for use in the methods of the instant invention.

One of skill in the art will appreciate the myriad sources of phage that may be used in the methods of the instant invention. Possible sources include, e.g., natural sources in the environment such as soil and sea water, as well as man-made sources such as untreated sewage water and water from waste-water treatment plants. Clinical samples from infected subjects (e.g., human patients, animals or any other species) may also serve as a source of phage. In a particular embodiment, diverse environmental sources of phage may be selected from the group consisting of soil, water treatment plants, raw sewage, sea-water, lakes, rivers, streams, standing cesspools, and animal and human intestines and fecal matter and any manure. Phage may be sourced anywhere from a variety of diverse locations around the globe, e.g., within the US and internationally.

Phage may be collected and isolated for use in the methods of the present invention using conventional methods. For example, a composition of tryptic soy (TS) broth powder in 300 ml of collected sample (e.g. sewage water) may be combined with 200 microliters of an actively growing target bacterial culture in an Erlenmeyer flask and incubated at 37° C. Culture samples may be harvested at different times (e.g., 6 hours, 18 hours), supernatant from aliquots of the cultures collected (10,000×, 2 minutes), filter sterilized, and the supernatant can then be used to inoculate each bacterial diversity set strain, and each bacterial diversity set strain/supernatant mix plated or spotted, and resulting plaques then resuspended and filtered sterilized and/or treated with chloroform according to conventional methods for isolating phage plaques. In a particular embodiment, plaque isolation may be repeated numerous times, e.g. three times, in order to purify phages capable of infecting the desired host from other mixed phages present in the environmental sample.

It is contemplated herein that, at this point in the phage isolation and phage library construction process, the only selection criterion for inclusion in the Tier 1 archival phage library is that the phages are lytic, i.e., they generate clear plaques when plated on their bacterial host(s). It is further understood herein that the collection of phage for the Tier 1 archival phage library is an iterative and ongoing process. Thus, as the bacterial diversity set is continuously updated, the Tier 1 archival phage library may also be continuously updated. It is contemplated herein that in a particular embodiment, the Tier 1 archival phage library may be any size, and possibly very large; for example, the amount of phage in the Tier 1 archival library may number in the thousands. For example, a Tier 1 library may comprise from about 750 to about 1500 phages. In a particular embodiment, a manageable number of phages may be approximately from about 1000 phages, but may be more or less without limitation. In one embodiment, the Tier 1 archival library may comprise greater than 1000 phages.

While the methods of the instant invention comprise isolating "wild" phage, it is also contemplated herein that the methods of the invention may comprise creating a Tier 1 working phage library also comprising phages that are readily available, e.g., previously isolated and characterized phages for use in the methods of the instant invention may be obtained from research laboratories and/or commercial sources. It is contemplated herein that phages from any variety of such sources may be used alone or in combination with phages harvested from the wild in a phage library of the instant invention.

Tier 2 Working Phage Library Construction:

According to the methods of the instant invention, phage assembled in the Tier 1 archival phage library is down-selected for inclusion in a working phage library, i.e., a "Tier 2 working phage library" to avoid including phages in a therapeutic cocktail that possess undesirable and/or toxic characteristics. As understood by one of skill in the art, the term "undesirable and/or toxic characteristics" refers to the presence of any gene(s) inside of a phage genome which would potentially activate the production of toxic proteins upon introduction of the phage in a subject's system. Additionally, phages carrying any antibiotic resistance gene(s), and/or lysogenic gene(s) are considered as possessing undesirable and/or toxic characteristics.

Accordingly, phage may be assessed based on various exclusion criteria in order to identify phages that are best suited for inclusion in a therapeutic phage cocktail; i.e., phages that demonstrate "nontoxic characteristics." For example, in a particular embodiment, phage in the Tier 1 archival phage library can be subjected to genome sequence analysis and/or PCR analysis to determine if any of the phages encode known toxin genes. For the creation of a therapeutic phage cocktail, phage with known toxin genes should be excluded from the working library. In addition, the phage can be subjected to genome sequence analysis and/or PCR analysis to determine if any of the phage encodes known lysogeny genes, or genes encoding known antibiotic resistance genes. Phage with known lysogeny genes and/or known antibiotic resistance genes should be excluded from the working library. With respect to antibiotic resistance, eliminating phages with known antibiotic genes prevents the addition of exogenous antibiotic resistance genes into the phage therapeutic treatment of an already MDR bacterial infection.

Phage administered therapeutically to a subject will typically elicit an immune response in the subject, including both innate and adaptive antibody and cell-mediated responses. The subject's immune response in some cases may antagonize efficacy of the phage therapeutic. Thus, it is contemplated herein that phage that elicit a strong antagonistic, i.e., inappropriate, immune response in the subject, e.g., an immune response that blocks and/or neutralizes the bacterial infectivity of the phage, may be excluded from the working library.

In a particular embodiment, phages that can transduce bacterial virulence factor genes may be excluded from the working library.

Thus, in a particular embodiment, phages which demonstrate undesirable and/or toxic characteristics and are excluded are selected from the group consisting of phages which carry toxin genes, phages which possess lysogenic properties and/or carry lysogeny genes, phages which can transduce bacterial virulence factor genes or antibiotic resistance genes, phages which carry any antibiotic-resistance genes or can confer antibiotic resistance to bacterial strains, and phages which elicit an inappropriate immune response and/or provoke a strong allergenic response in a mammalian system.

As understood herein, an "inappropriate immune response" may vary and can be assessed on a case by case basis. For example, it is contemplated herein that in some cases, the lack of an immune response to phages in the subject is desired so that the phages can freely kill the bacterial pathogen. On the other hand, it is also possible that the mechanism of action of other phages involves a strong host immune response that is recruited to the infection site by the phages and stimulates the immune response against the bacterial target. One of skill in the art will appreciate the conditional nature of, and potential benefit of, tailoring cocktail formulations that elicit different kinds of immune responses, and the need to select the appropriate phages for a cocktail accordingly.

The phages passing the exclusion criteria listed above are then screened against the bacterial diversity set in order to determine the bacterial host range of each phage, in order to identify and include those phages having desirable host ranges. As understood herein, determining the "bacterial host range" refers to the process of identifying the set of bacterial strains that are susceptible to infection by the given phage. Thus, as used herein the term ""host range" refers to the empirically determined set of bacterial strains, e.g. particularly strains of the bacterial diversity set, and/or phage resistant mutants thereof, that a phage (or a phage cocktail) is able to infect and kill. Screening to determine a phage's bacterial host range may be performed using conventional methods familiar to one of skill in the art, including but not limited to assays using robotics and other high-throughput methodologies.

As understood herein, a "desirable" host range is contextual, as one of skill in the art will appreciate. In some cases, phages with a desirable host range may include phages that target many bacterial isolates of interest, e.g., many of the bacteria in the diversity set. In other cases, phages with narrow and/or specific host ranges are required. For example, in the diversity set, as representative of the current clinical bacterial burden, there may be phenotypes and/or representative bacterial strains that are particularly difficult for phages to infect, thus phages capable of infecting these strains may be rare and/or difficult to isolate, and identifying phages that can kill these and only these problematic strains is critical. In a particular embodiment, the goal is to build a Tier 2 working phage library comprising phages with distinct but complementary host ranges. Indeed, a host range of one phage may overlap with the host range of a different phage. The concept is similar to that of a Venn diagram; each circle can represent an individual phage's bacterial host range, which may intersect with one or more other phage's bacterial host range. On the other hand, the host range of the phage (or phage cocktail) may be specific, or "unique" to a particular bacterial pathogen of interest, e.g., a "unique host range."

Phage bacterial host ranges may be broader or narrower than other host ranges. Phages with a broad host range indicate, in general, that the receptor for said phage is common among the strains, while a narrow host range may indicate that a unique receptor is used. For example, as used herein, a "broad host range" can refer to the ability of a phage to infect from about 15 or more bacterial strains, while a narrow host range can vary from about 1 to about 5 bacterial strains.

Phage cocktails of the instant invention may be compounded with phage bacterial host range specificity in mind. Indeed, it is contemplated herein that the phage cocktails of the instant invention may be compounded to comprise phages with broad host ranges, narrow host ranges, specific host ranges, or combinations thereof. In some cases, a phage cocktail comprising phages with the broadest host range possible may be desired; in other cases, a phage cocktail comprising phages with narrow host range phages may be desired, e.g., to make a phage cocktail(s) that comprises phages that work synergistically to eradicate the bacterial pathogen.

In a particular embodiment, similarly, the Tier 2 library may comprise phages having distinct, but overlapping, bacterial host ranges. Thus, in a particular embodiment, the Tier 2 working library may be designed to comprise phages with broad bacterial host range, phages with a narrow bacterial host range, or a combination thereof.

A Tier 2 working phage library of the instant invention may comprise any number of phages. In a particular embodiment, it is contemplated herein that a Tier 2 working phage library may comprise from about 100-750 phages. It is contemplated herein that in a particular embodiment, a manageable number of phages may be approximately about 500 phages, but may be more or less without limitation. In a particular embodiment, a Tier 2 working phage library of the instant invention may include hundreds of phages. In another embodiment, the Tier 2 working library may comprise less than 1000 phages.

The methods of the instant invention comprise purification of phage preparations, e.g., to minimize endotoxin and foreign antigens present in crude phage lysates. Such purification may be performed using conventional methods, e.g., comprising the use of cesium chloride density gradients and ultracentrifugation, and optionally, comprising methodologies consistent with good manufacturing practice guidelines (GMPs) in view of the ultimate goal of producing a therapeutic phage cocktail for administration to a subject. Such guidelines are familiar to one of skill in the art.

The term "purified" refers to a preparation that is substantially free of unwanted substances in the composition, including, but not limited to extraneous biological materials e.g., nucleic acids, proteins, carbohydrates, lipids, or toxins, and/or other impurities, e.g., metals or other trace elements, that might interfere with the effectiveness of the cocktail.

In the method of the instant invention, following downselection, phages in the Tier 2 working phage library may be purified at high titer and high purity, and held in reserve for facilitating rapid cocktail formulation. Alternatively, in another embodiment, it is contemplated herein that phage in the Tier 1 archival phage library may be similarly purified at high titer and high purity prior to down-selection and creation of the Tier 2 working phage library. The phage libraries may also be purified to very high titer and very high purity.

As used herein, terms like "high titer", "very high titer, "high purity", and and very high purity" refer to degrees of titer and purity that are familiar to one of skill in the art. For example, with regard to the methods of the instant invention, "high titer" and like terms means a phage preparation which contains approximately $10^9$ to $10^{10}$ plaque forming units (pfu)/ml of phage particles. The term "very high titer" and like terms means titers in excess of $10^{11}$ pfu/ml. One of skill in the art will appreciate that the titer of the phage combinations and phage cocktails compounded according to the methods of the instant invention may vary. In a particular embodiment, formulations for administration to subjects for therapeutic use ideally will be of therapeutically effective titer, e.g., high or very high titer, prepared according to GMPs.

Similarly, "high purity", "highly pure" and like terms means phage preparations purified through differential centrifugation techniques or similar methods. Similarly, "very high purity" means phage preparations purified through isopicnic density gradient technique specifically on cesium or other heavy salt gradients, or similar methodology. One of skill in the art will appreciate that the degree of purity of the phage combinations and phage cocktails compounded according to the methods of the instant invention may vary. In a particular embodiment, formulations for administration to subjects for therapeutic use ideally will be of pharmaceutically acceptable purity, e.g., high or very high purity prepared according to GMPs.

In another embodiment, it is contemplated herein that the methods of the instant invention may comprise producing large amounts of phage in the Tier 1 archival phage library and/or phage in the Tier 2 working library. One of skill in the art will appreciate the meaning of such concept in the context of the field of phage biology and methodologies. As used herein, the term "large amounts" includes, but is not limited to at least $10^9$ pfu/ml of phage particles and at least a liter of such a preparation. In a particular embodiment, large amounts of phage are prepared at high titer or very high titer and/or at high purity or very high purity according to GMP guidelines, to facilitate compounding of therapeutic phage cocktails. As understood herein, "facilitating compounding" includes decreasing the length of time required to produce a phage cocktail for clinical administration.

Similar to the process associated with maintaining a Tier 1 archival phage library and a bacterial diversity set, it is contemplated herein that the down-selection of phages for the Tier 2 working phage library may also be an iterative and ongoing process. Thus, as the bacterial diversity set is updated, the Tier 1 archival phage library, and also the Tier 2 working phage library may be correspondingly updated according to the methods of the invention.

In a particular embodiment, the method of the instant invention uses phages with different but desirable host ranges to populate the Tier 2 phage library, so as to build a characterized working library comprising phages with diverse and desirable host ranges. In the method of the instant invention, cocktails are built from this library empirically.

Custom/Personalized Phage Cocktail Formulation:

It is contemplated herein that the dynamic nature of the bacterial diversity set, and the Tier 1 and the Tier 2 phage libraries described above are key reagents of the methods of the instant invention as they enable the rapid identification and compounding of phage cocktails, from relevant and characterized phages, for use as effective therapeutics in a subject in need thereof. In this regard, it is contemplated herein that one or more steps of the methods of the instant invention may be performed using robotics or other high throughput assays familiar to one of skill in the art, to further enable rapid reagent construction and/or cocktail formulation.

Specifically, in order to rapidly arrive at a therapeutic phage cocktail for a given subject, the phage information compiled in the Tier 1 and Tier 2 libraries may be applied in combination with phage efficacy assays to rapidly identify and generate a therapeutic phage cocktail for the subject.

As used herein, a "phage efficacy assay" refers to an assay to detect the effectiveness of one or more phages, or a phage cocktail, to prevent bacterial growth in culture media which otherwise supports robust bacterial growth. Such an assay may comprise growing cultures of a targeted bacterial pathogen with individual phages, and/or various phage combinations from the Tier 2 working phage library, and analyzing bactericidal activity against said bacterial pathogen, wherein a suitable delay in bacterial growth and/or the lack of appearance of phage-resistant bacterial growth in a culture indicates that an individual phage and/or a various phage combination may be therapeutically effective against said bacterial pathogen. For example, a clinical isolate of a bacterial pathogen may be cultured overnight (e.g., to log phase), and then isolate inoculum aliquoted to phage dilutions in wells of a 96 well-plate. The interaction between the bacteria and phage is then monitored for evidence of bacterial growth delay using conventional methods, and specifically, in a particular embodiment, according to assay methods as described herein.

In addition to the foregoing, it is contemplated herein that one may be able to perform a prescreening method to reduce the number of phages needed to be screened in a phage efficacy assay. Specifically, this prescreening methods links bacterial spectral features with phage infectivity or susceptibility. Correlating spectral features of a targeted bacterial pathogen with susceptibility to infection by specific phages may be possible as bacterial spectral features can correlate with the presence or absence of specific surface structures which serve as phage receptors, and these receptors, by extension, can correlate with phage infectivity. Thus, prescreening the infectious bacterial target with spectral assays before running a phage efficacy assay can inform which phages in the Tier 2 library (or Tier 1 library as needed) should be screened first in order to decrease the time necessary to compound a synergistic cocktail. Spectral assays that may be employed in this regard include but are not limited to Raman spectroscopy, mass spectroscopy, and/or fluorescent immunolabeling. Thus, in a particular embodiment, it is contemplated herein that spectral assays may be used to reduce the number phages to be screened in the first round of iterative screening of the Tier 2 library, by analyzing spectral features which correlate with phage infectivity or susceptibility. It is contemplated herein that such assays may comprise the use of automated systems.

Additionally, as the correlative power between the bacterial spectral features and verified phage infectivity increases, e.g., through verification using a phage efficacy assay described herein, it may be possible to eliminate the need for a phage efficacy assay in all cocktail compounding events. Such elimination can be based on the analysis of correlative data between spectral features and phage infectivity and/or susceptibility. Thus, in a particular embodiment, where correlative spectral data exists between bacterial spectral features and phage infectivity, the phage efficacy assay and/or rounds of iterative library screening may not be needed in all synergistic cocktail compounding events.

One of skill in the art may employ a variety of existing conventional methods for "growing cultures of a bacterial pathogen with individual phages, and/or various phage combinations" to assay the ability of phage to kill bacteria, delay bacterial growth, and/or to detect the lack of appearance of phage-resistant bacterial growth. These include, for example conventional phage plaque assays or spot assays where the effectiveness of phage or various phage combinations to prevent bacterial growth can be evaluated on solid agar or semi-solid medium media.

In a particular embodiment, high-throughput methodologies comprising the use of microtiter plates and liquid media for running multiple simultaneous assays and cultures are also contemplated herein. For example, the delay in bacterial growth and/or the lack of appearance of phage-resistant bacterial growth may be monitored comprising the use of a high-throughput photometric assay and liquid media. In particular embodiments, the photometric assay may be, e.g., fluorescence, absorption, or transmission assays. In a particular embodiment, the photometric assay comprises a step wherein an additive such as tetrazolium dye is used to cause and/or enhance the photometric signal detection. For example, in a particular embodiment, such assays include phage efficacy assays monitoring the delay in bacterial growth, called a growth "hold-time," which can be used to determine the lytic activity of individual phages or compounded phage cocktails using an automated, high throughput, indirect liquid lysis assay to evaluate phage bactericidal activity using an OMNILOG system (Henry M, et al. 2012. Bacteriophage 2:159-167). Such assay is described in Example 1.

The phage efficacy assay described in Example 1 is a liquid-based assay that can be performed in high-throughput, e.g., with robotic assistance in 96-well plate format, and it monitors bacterial metabolic activity rather than growth (culture turbidity). The assay monitors a colorimetric change in a dye in response to bacterial respiration. This color change is a surrogate for viability of the bacterial strain. Essentially, the assay can be used to determine, per well of a 96-well plate (each well being a unique culture) whether the phage prevent or delay the color change/bacterial respiration/bacterial viability/bacterial growth. In other words, the assay is performed to determine whether a phage kills, i.e., can hold and/or prevent bacterial growth. For example, results for wells (cultures) containing individual phages from the Tier 2 library are analyzed and individual phages with desired hold-times are selected and differentially compounded into cocktails. The bactericidal activity of the cocktails is reassessed following the same procedure. Once the cocktail hold-time is determined, it is also possible to perform the 96-well assay again, only now every well contains the identified cocktail and one or more different phages from the Tier 2 working phage library (and/or the Tier 1 library and/or newly identified uncharacterized phages, as needed), in an effort to identify an additional phage(s) that further enrich the activity of the cocktail and augment the hold-time of said identified cocktail, and/or find possible additional therapeutically effective phage combinations. In a particular embodiment, the goal of cocktail formulation as described here is to identify phage cocktails that work synergistically, e.g. cocktails whose hold-times are greater than the simple addition of the hold-time of each of the constituent phages in said cocktail.

When a lytic phage is mixed with its bacterial host, under the right conditions, the phage will infect and kill the vast majority of the bacterial host. Either due to pre-existing mutations in the bacterial population, or active mutagenesis processes in the bacterial cell, a small fraction of the bacterial host will be or will become resistant to the phage. An example of this is seen in Example 2 provided below where *A. baumannii*, once exposed to the appropriate phage, ceases capsule production. Thus the phage selects for a population of either pre-existing or emergent bacterial mutants that no longer produce a capsule. The capsule is likely the receptor for this phage, and the loss of the capsule results in a bacterial population that is now resistant to the phage. This new unencapsulated bacterial strain then has to be targeted with a completely different set of phage, and these phages only infect unencapsulated *A. baumannii*. Adding these phages kills the unencapsulated population, allowing the therapeutic cocktail to function effectively, even though these phages targeting the unencapsulated bacteria do not infect the original encapsulated strain. When added to the original encapsulated *A. baumannii* these phages that target the uncapsulated bacteria have an undetectable effect on the original encapsulated *A. baumannii* population. Thus, the effective cocktail against *A. baumannii* described in Example 2 is compounded using one phage that only partially holds the growth of the parent bacterial strain and four more phage that have little to no detectable impact on the parent encapsulated strain. It is only in the context of the cocktail that the activity and necessity of the phages targeting unencapsulated *A. baumannii* becomes apparent. The said cocktail also functions synergistically, as the hold-time of the cocktail is far greater than the simple addition of the hold-time of the phage that infects encapsulated *A. baumannii* and the 4 phages that exclusively infect the unencapsulated emergent *A. baumannii* mutants.

It is contemplated herein that the methods and compositions of the instant invention provide a vast improvement in the field of phage therapy. For example, since the methods of the present invention identify phage cocktails which comprise phage that do not have a detectable effect on the parent strain of the bacterial pathogen, (e.g. the encapsulated *A. baumannii*), the compounding of therapeutic phage cocktail formulations described herein are counterintuitive; such cocktails likely would not be identified, let alone readily or reliably identified, according to conventional methods which rely on the use of pre-isolated phages already suspected as having a detectable bactericidal activity, and therefore a potential therapeutic effect on a particular clinical bacterial strain. Phages like those that can be identified here, which only infect small sub-populations of an infectious bacterial strain, have no detectable activity when assayed using conventional methods. Thus, using classical methods, there is no activity or basis for including them in a potential therapeutic phage cocktail. Using classical methods, phages such as these may actually be eliminated from the pool of phages with therapeutic potential against said bacterial pathogen. Moreover, the methods of the instant invention allow the detection of previously unidentified therapeutically effective phages, including previously unknown synergistic combinations of phages, quickly and easily, against numerous bacterial species, permitting new and different phages to be identified for potential therapeutic use.

Phage therapeutics seeks to exploit the predator-prey relationship between a phage and its host bacteria. Like all predator-prey relationships, unless the predator drives the prey to extinction, and assuming other environmental factors are held constant, equilibrium between the predator and prey will be established. In the case of phage-bacterial interactions, phage-resistance is a manifestation of such equilibrium. Thus the goal of phage therapeutics is to identify phages and phage cocktail formulations that are capable of eradicating a bacterial population, e.g., driving the infectious bacterial population to near extinction within the subject in need of therapy. Indeed, the cocktail formulations compounded using the methods of the instant invention which are designed to eradicate or nearly eradicate an infectious bacterial population, and which are often synergistic and counterintuitively include phages that actually have no detectable activity against the targeted bacterial pathogen on their own, are very rare. Thus the combination of phages that make up the therapeutic phage cocktails compounded using the method of the instant invention are unlikely to be found in nature. Additionally, prior to the method of the instant invention, there was no way of systematically and reliably identifying phages for inclusion into a therapeutic cocktail that had no detectable activity against the targeted bacterial pathogen on their own.

As used herein, the terms "desirable delay in bacterial growth", "suitable delay in bacterial growth", "growth hold time", "lack of appearance of phage-resistant bacterial growth" and like terms is understood to relate to the effectiveness of a phage, phage combination, or phage cocktail to prevent bacterial growth for a given amount of time in culture. In a particular embodiment, this includes bacterial growth in the liquid culture environment described in Example 1. Typically, in this assay, growth hold-time indicative of a promising phage is from about 4 to about 8 hours.

In a particular embodiment, the growth hold time of a promising phage cocktail, assembled from individual phages deemed as promising, may be a minimum hold-time of about 12 hours to about 18 hours or longer without limit. In other particular embodiments, the growth hold time of a phage or phage cocktail may be from about 15, 16, 17, 18, 19, or 20 hours. In another embodiment, cocktail hold-times of less than 12 hours may have therapeutic efficacy.

In yet another embodiment, the growth hold-time of a promising individual phage may be zero or undetectable and only when this type of phage is included with another phage deemed to be promising, or as a new constituent of a cocktail deemed to be promising, will the activity and necessity of such a phage become detectable. In such situations, phages of this type, which have undetectable or nearly undetectable activities on their own, can surprisingly add to a synergistic hold-time when included in promising phage cocktails.

It is contemplated herein that the methods of the instant invention can be used to identify a phage combination that can produce a complete or nearly complete growth arrest of the bacterial pathogen. This may be evident from a growth hold time from about 16-48 hours or more.

One of skill in the art will appreciate that promising growth hold times, including minimum hold times, and growth hold times indicative of complete or nearly complete growth arrest, may vary depending on the species of bacteria, e.g., some bacterial species typically grow more slowly than other bacteria. Promising growth hold times of bacteria under investigation may be easily discerned according to the methods of the instant invention without undue experimentation.

Specifically, in a particular embodiment, a phage cocktail may be identified according to the methods of the instant invention as follows. Upon presentation, a clinical sample is taken from a subject suffering from a bacterial infection. Typically, but not necessarily, the subject is infected with a MDR bacteria. The infective bacterial strain in the isolate is identified using conventional methods and then matched against the bacterial species of existing bacterial diversity sets and Tier 1/Tier 2 phage libraries. At this point, previously compounded phage cocktails against the same bacterial species may be rescreened for the ability to infect and kill (or delay the growth of) the subject's infective bacterial strain using a high throughput or robotics-based phage efficacy assay such as described in Example 1.

If no previously compounded cocktails are found to adequately kill the infective bacterial pathogen, the Tier 2 library for the same bacterial species can be screened specifically against the subject's infective bacterial pathogen. It is contemplated herein that according to the methods of the instant invention, therapeutic phage cocktails may be obtained by screening all phages in the Tier 2 working phage library against a target bacterial pathogen individually.

According to the methods of the instant invention, any phage showing any delay in resistant bacterial growth infects that bacterial target to some degree. As discussed above, such phages may produce growth holds to some extent, but insufficient to result in effective treatment of the bacterial infection on their own. Generally, promising growth hold-times may be approximately from about 4-8 hours. In a particular embodiment, the growth hold time of a therapeutic phage cocktail is about 18 hours or more. Upon identification, phages which display some amount of growth hold time may be variously combined into other phage combinations (cocktails) and rescreened, e.g. the phage efficacy assay is performed again with the various phage cocktails, to look for improved growth hold-times. Additionally, a phage efficacy assay can be performed again with these cocktails and the individual addition of another phage from the Tier 2 library (and/or the Tier 1 library and/or wild phages recently isolated), as needed. Such rescreenings can be used to rapidly arrive at new phage combinations which demonstrate improvements in growth hold-time. Such improvements may be additive increases in growth hold-times, or they may in fact demonstrate synergistic improvements in the delay in phage-resistant bacterial growth.

In view of the foregoing, it is contemplated herein that several iterations of screening (rescreening) according to the methods of the instant invention may be performed to obtain the final formulation of phages for compounding into a therapeutic phage cocktail that achieves and/or maximizes a synergistic increase in hold-time. In a particular embodiment, the method may encompass screening a phage library against a clinical bacterial pathogen in question using each phage individually per well of a plate (i.e., so each phage is screened individually against the pathogen), and identifying phages that give approximately a 4-8 hour hold time. These identified phages are then cocktailed, and the assay is repeated looking for a combinatorial and ideally synergistic hold-time between approximately 16-20 hours or more. If no synergy is seen, and/or if the cocktail hold-time does not achieve 16-20 hours, the 96-well assay can be performed again, only now each well contains the identified cocktail and at least one additional phage from the Tier 2 library and/or the Tier 1 library and/or a newly identified wild phage, in an attempt to identify new phages for the cocktail that will augment, and ideally, act synergistically to improve, growth hold time. It is in these rescreening steps that one may find an additional phage with a previously undetectable activity against the targeted pathogen, but now in the context of a cocktail, its activity, presumably against a phage-resistant sub-population, is now detectable and can be seen as required to achieve synergy and therapeutic efficacy.

According to the methods of the instant invention, cocktail compounding is flexible, e.g. if a previously identified cocktail against the same bacterial species as the targeted pathogen shows adequate activity and/or if a synergistic hold-time of 16-20 hours can be achieved from the initial Tier 2 library screen and cocktail formulation, then rescreening is not necessary. The method of the instant invention is also scalable, e.g., if the initial Tier 2 library screen and cocktail formulation fails to produce a synergistic cocktail with a 16-20 hour hold-time, rounds of iterative rescreening can be performed using a promising preliminary cocktail and individual phages from the Tier 2 library (and/or Tier 1 library, and/or newly isolated wild phages) until one identifies a cocktail that can achieve a synergistic hold-time of 16-20 hours. It is in the iterative rescreening that phages with undetectable activities against the targeted bacterial pathogen on their own will be identified, and the activity of such phages will be both detectable and required in the final formulation of the synergistic cocktail. Ideally, the identified and compounded phages will be capable of killing the bacterial strain together.

Of course, as mentioned above, the methods of the instant invention may be used to produce a therapeutic phage cocktail after just one screening. Indeed, the methods may identify a phage cocktail that produces a synergistic effect on bacterial growth hold-times after just one screening of a Tier 2 library. On the other hand, phage cocktails may be identified wherein the combined effect on bacterial growth hold-times is additive and/or insufficient.

Moreover, when a phage cocktail of the instant invention preys upon a bacterial strain, it may produce a resistant bacterial strain, e.g., through selection and/or active mutation. That is, the resistant strain may have been present in very low frequency in the parent population (e.g., it did exist but in such low frequency that the new phage's activity was previously undetectable) or such resistant strain may not have existed in the parent bacterial population prior to the activity of the cocktail, but arose as a result of treatment with the phage cocktail itself. It is contemplated herein that such resistant bacterial strains may be susceptible to some other phage, i.e., a phage that showed no inhibitory activity previously (e.g., a phage in the Tier 2 working phage library, and/or Tier 1 archival phage library, and/or one or more newly harvested "wild" or other previously untested phage).

Thus, while phage cocktails of the instant invention may show therapeutic effectiveness, phage cocktails with augmented clinical effectiveness may be desired. Specifically, while a bacterial growth hold may be therapeutically acceptable, further delay in bacterial growth may be desired in order to provide a more therapeutically effective composition. Accordingly, it is contemplated herein that the methods of the invention may comprise rescreening steps.

Indeed, in situations in which complete bacterial eradication is not achieved, it may be that all of the phages are killing the same isoform of the bacterial strain within the larger population, i.e., killing the dominant bacterial isoform in the bacterial population, but missing the low-frequency bacterial isoforms at the periphery of the population. In this case, one could go back and screen the library again in the presence of this cocktail, looking for other phages whose therapeutic contribution might now only be detectable in the context of the presence of this first cocktail. That is, these phages may infect rare members of the overall bacterial population, and their killing activity might only be detectable when the freshly discovered cocktail is used. Accordingly, it is contemplated herein that the methods of the instant invention provide a unique way of identifying and demonstrating the therapeutic value of a wide variety of phages, and which would otherwise be overlooked using conventional methods.

Thus, in a particular embodiment, in the event that an improved therapeutic affect is desired, (e.g., if an augmented or even a synergistic delay in bacterial growth is desired) various compounded phage cocktails (i.e., compounded according to step (f) of the method), can be rescreened (e.g., in high throughput using the phage efficacy assay disclosed in Example 1) against every individual phage in the Tier 2 working phage library (i.e., rescreened according to step (e) of the method) to find a combination of phage that produces an augmented or even synergistic inhibitory affect on bacterial hold-time/growth delay.

It is further contemplated herein that in additional embodiments, phage cocktails which produce synergistic affects on growth delay may be rescreened in order to find phage combinations which provide an even greater therapeutic benefit, including but not limited to, even greater synergistic affects on growth hold-time.

Accordingly, any phage cocktails of the instant invention may be rescreened not only against individual phages in a Tier 2 working phage library, but also against a Tier 1 archival phage library, and/or even against wild or other newly acquired phages to identify possible phage cocktails that display greater therapeutic benefit, including greater synergistic inhibitory effects on bacterial growth hold time.

Rescreening steps contemplated herein may be achieved, e.g., by addition of the entire compounded phage cocktail to a well of a culture plate, and a new phage (i.e., phage from any one of the Tier 2 working phage library, Tier 1 archival phage library, and/or wild or otherwise newly acquired phage) is added to the well and analyzed for a possible enhancement in the degree of growth inhibition, including but not limited to enhancement in any synergistic affect on growth inhibition, that may not have been detected before.

As understood herein, improving the therapeutic effect of a phage cocktail need not be limited to effects on bacterial growth holds, bacterial killing, or other measure of bactericidal activity. For example, it is understood herein that phage therapy exploits a predator prey relationship, thus resistance is anticipated and targeted according to the methods of the present invention. It is contemplated herein that while phage predation may cause a phage-resistant bacterial population to emerge, that population may be less virulent and/or may be altered such that they display reduced fitness for growth in the subject. In addition, the emergent population may be more susceptible to antibiotics; i.e., phage resistance may alter virulence and may induce re-sensitization to antibiotics. Thus, a phage cocktail of the instant invention may comprise phages that can augment the therapeutic efficacy of a phage cocktail in a manner beyond merely enhancing bacterial killing/delaying growth/bactericidal activity, e.g., by making the subject's MDR infection more responsive to antibiotics. Indeed, evidence of such findings is suggested in several of the examples provided below.

Additionally, during therapeutic application of a phage cocktail of the instant invention, the phages may act as good adjuvants by provoking the humoral and cell mediated immunity of a mammalian system against the bacterial pathogen. For example, and without intending to be limited by any particular mechanism of action, it is contemplated herein that bacterial debris attached to the individual phage particles may act as a good immunogen during effective lysis of bacteria after phage treatment and thus may enhance the therapeutic efficacy of a phage cocktail.

In the event that a suitable cocktail cannot be generated against a bacterial pathogen, screening of the Tier 1 phage library and/or new environmental samples against said pathogen may be used to identify new phages for inclusion into the Tier 2 working phage library and/or a cocktail against said pathogen. In addition, it is further contemplated herein that the bacterial diversity set and/or the phage libraries of the instant invention may be regularly or "iteratively" updated to include different bacterial strains or phage, respectively. As understood herein, "iteratively" encompasses regularly updating the contents of the bacterial diversity set and/or phage libraries on a regular temporal basis. For example, from time to time (e.g., once a year, or less or more frequently as desired) isolates of bacterial strains, including new bacterial clinical isolates, may be (re)evaluated for inclusion in the bacterial diversity set. Similarly, new wild phages may be harvested or otherwise obtained from other available sources and incorporated into the Tier 1 and/or Tier 2 working phage libraries after proper evaluation to confirm that the phages are appropriate, e.g., lytic, free of any toxin genes, etc. as discussed above. Accordingly, it is contemplated herein that phage cocktails of the instant invention may be assembled from a robust, characterized, and flexible phage libraries which contemplates that effective therapeutic cocktails might comprise 'fresh' wild-caught phages, and that the phage libraries may be constantly updated to chase clinically relevant strains of bacteria.

While the bacterial diversity set and/or the Tier 1 and Tier 2 phage libraries of the methods of the instant invention may be updated over time out of biological necessity, it is also contemplated herein that, in another embodiment, the Tier 1 library may not need to be updated to continue to be effective in the methods of the instant invention. For example, as clinically relevant bacterial strains change over time, phages in a Tier 1 archival phage library that were excluded from the Tier 2 library due to host range considerations, might now function to kill the new clinically relevant bacterial strains added to the bacterial diversity set, even though previously these phages seemed redundant and/or inappropriate for the Tier 2 library.

While the methods of the invention contemplate possible rescreening steps to identify a therapeutic phage cocktail and/or to augment the therapeutic efficacy of a phage cocktail, it is also contemplated herein that the methods of the instant invention may not require rescreening against a Tier 1 archival phage library and/or against wild/newly acquired phage upon establishing a robust Tier 2 working phage library which is iteratively updated as discussed above. Indeed, the methods of the instant invention encompass establishing a robust Tier 2 working phage library that is well characterized and may be used to compound therapeutic phage cocktails against a majority, or nearly all, clinically relevant pathogens of said species of bacterial pathogen. As understood herein, an "established" Tier 2 working phage library is a defined phage library which serves as a depository of phages screened to be free of any harmful entities, e.g., toxin genes, lysogenic genes and antibiotic resistance genes as discussed herein. An "established" Tier 2 library is understood to be a collection of phages that will be updated iteratively, as needed, as the dominant clinically relevant strains of bacteria will naturally change over time.

Significantly, it is contemplated herein that once a Tier 2 working phage library has been established, clinical samples of bacterial pathogens may be obtained from a subject and quickly screened against pre-existing phage cocktails and/or the established Tier 2 working phage library to identify phages for a therapeutic phage cocktail as disclosed herein. Accordingly, consistent with the idea of creating "established" Tier 2 libraries, it is contemplated herein that bacterial diversity sets, Tier 1 archival phage libraries, and Tier 2 phage libraries may all be generated "in advance", i.e., already available for use in compounding phage cocktails according to the instant invention upon presentation of an isolate of a bacterial pathogen. Thus, the performance of the steps of the methods of the instant invention are not limited to first receiving a clinical bacterial isolate from a clinician; a bacterial diversity set and phage libraries may be established according to the methods of the invention beforehand, in anticipation of the receipt of possible clinical bacterial isolates. As such, in contrast to prior art methods, the present invention can permit the rapid and reliable identification of a therapeutic phage cocktail for many subjects in need thereof, including many patients for whom there are few, if any, remaining clinical options.

The methods of the instant invention are scalable and tailorable. For example, in a particular embodiment, suitable phages of interest against a bacterial pathogen may be readily available such that one may not need to obtain phage from the wild to build a phage library for use in the methods of the instant invention. Thus, it is contemplated herein that in a particular embodiment, the methods of the instant invention may be performed without first needing to perform the step of collecting phages in environmental samples from diverse environmental sources.

Similarly, while it is contemplated herein that the methods of the instant invention may be performed in an iterative manner, as discussed herein, one of skill in the art will appreciate that the degree to which the steps of the method need to be repeated in order to obtain a therapeutic phage cocktail can vary. Indeed, because the method is modular and scalable, the method may be used to identify a first therapeutic phage cocktail, whereas compounding subsequent cocktails for the same patient (or other patients infected with the same bacterial pathogen) may not require performing all the steps of the method and/or performing iterative rescreening.

Indeed, while the present invention allows for the creation of therapeutic "personalized" phage cocktails, it is contemplated herein that multiple patients presenting with the same symptoms and clinical strain of bacteria may benefit from the same phage cocktail; i.e., a second patient presenting with the same bacterial strain as a first patient may benefit from treatment with a "personalized" phage cocktail developed to treat the first patient. This may be the case, for example, when patients may have been exposed to the same environmental conditions, e.g., patients from the same geographic location, hospital, or other medical treatment facility in which a particular strain of MDR bacteria may be prevalent. Thus, the methods of the invention encompass treating more than one patient with a "personalized" cocktail if deemed clinically sound to do so.

Thus, because the methods of the present invention produces personalized therapeutic cocktails, the manner in which a therapeutic phage cocktail is identified may vary according to the needs of the patient and the particular virulence of the bacterial pathogen; e.g., identification of a therapeutic phage cocktail may not require iterative screening or it may require only a few rounds of iterative screening. On the other hand, to successfully treat some patients, it may, in fact, require not only several rounds of iterative library rescreening to develop an appropriate cocktail, it may require several such cocktails developed over time as the bacterial strain changes within the patient in need of therapy, particularly if the infectious bacteria can readily develop phage resistance. Notably, even when additional rounds of screening are performed, it is contemplated herein that the methods of the instant invention permit the design and compounding of a therapeutically effective phage cocktail more rapidly than conventional methods.

Importantly, the method of the instant invention is empirical and is based on cocktail performance. While it is evident in the case of the *A. baumannii* cocktail described in Example 2 that one phage infects encapsulated bacteria, while the four others infect unencapsulated bacteria, it is critical to appreciate that this level of mechanistic understanding is not required to generate effective cocktails using the methods of the instant invention. In fact, such a mechanistic understanding will not be attained for most of the cocktails defined by the methods of the instant invention. Indeed, there is no need to identify the phage receptor or to understand the population dynamics that occur during phage infection and bacterial eradication, either in the lab setting during formulation, or even during successful treatment in a patient. This is a significant departure from the prior art, which often seeks to understand the mechanism of killing by a phage cocktail, and the receptors used by each phage. Characterizing each cocktail in this manner is laborious, time consuming, and expensive. In contrast, in the methods of the instant invention, by beginning with a robust and characterized phage library, optionally followed by one or more rounds of iterative screening as needed, therapeutically effective cocktails can be compounded simply based on performance.

Manufacturing:

Once a phage cocktail is identified that kills the infective bacterial pathogen in vitro (e.g., as evidenced by a phage efficacy assay), the phage cocktail may be manufactured for clinical use. In a particular embodiment, highly pure and high titer preparations of the phage cocktail may be manufactured using conventional methods according to GMP guidelines. In a particular embodiment, manufacturing methods comprise growing phage for a phage cocktail on cultures of the actual bacterial pathogen of interest and/or on laboratory strains, manufacturing strains, production strains, and/or on other domesticated strains of the same species as said bacterial pathogen and processed for clinical use.

Indeed, one of skill in the art will appreciate that the choice of the manufacturing strain can be consequential. Every time a phage grows on a different permissible host bacterial strain, there will be some level of host-adaption. For instance, if a phage is found that successfully infects a particular pathogen of interest, if that phage is then manufactured on an exogenous host, the resulting manufactured population will have adapted to the manufacturing strain, i.e., the resulting manufactured population will be the progeny phage that are best suited for infecting that manufacturing strain. This host-adaption may be inconsequential with respect to the ability of the resulting manufactured phages to infect the targeted bacterial strain, or the population of the manufactured phages may have significantly shifted away from being optimized for the targeted pathogen. Such a shift may be undetectable in vitro in the lab, but could be extremely significant in the context of a human or animal host with an immune system and mechanisms for eliminating phages, e.g., circulating macrophages and neutrophils, as well as Kupffer cells and dendritic cells. Thus for the method of the instant invention, in one embodiment, the actual targeted strain isolated from the patient in need of therapy will be used for the manufacture of each of the constituent phages of a cocktail identified by the methods of the instant invention. Use of the actual targeted bacterial pathogen for manufacturing of the constituent phages allows for the best possible match between the manufactured phages and the actual targeted bacterial pathogen. Phages which may be included in the formulation of a particular cocktail that do not have a detectable activity against the targeted bacterial pathogen, and therefore cannot readily grow on the targeted bacterial pathogen, may be grown on a permissive domesticated manufacturing strain.

In another particular embodiment, all of the phages in a cocktail identified by the method of the instant invention may be manufactured on permissive domesticated manufacturing strains. Additionally, in a particular embodiment, all of the phages in the Tier 2 library and/or Tier 1 library may be prepared in very high titer and very high purity on permissive domesticated manufacturing strains and stored so as to facilitate rapid compounding of the cocktail from these previously prepared phages.

As understood herein, "laboratory strains" include bacteria which are proven to be innocuous and can be used as a phage growth host. "Manufacturing or production strains", "domesticated strains", and "permissive strains" encompass bacterial strains capable of serving as hosts for the constituent phages of a particular cocktail, but are GMP and/or avirulent and/or attenuated for virulence and/or do not contain toxins, unwanted antibiotic resistance genes, or prophages.

In a particular embodiment, production of a personalized phage cocktail of the instant invention may be performed as follows. Selected phages from a Tier 2 library (all phages selected for the library will be grown and stored separately following the same procedures) or other phages as needed may be grown in small scale liquid lysate of approximately 5 ml-100 ml (phage amplification stage lasting approximately 1.5 hours), then grown in a large scale liquid lysate of approximately 1 L-20 L (phage amplification stage lasting approximately 2.5 hours), then the individual selected phages may be purified using tangential flow filtration (TFF) (approximately 3 hours), followed by a CsCl density gradient purification (ultracentrifugation lasting for approximately 16 hours), followed by dialysis with PBS (3 exchanges, pH 7.4 lasting for approximately 4 hours), and filtration through a 0.22 micron filter. The purified individual phages may then be titered and compounded into the identified cocktail. After the phage cocktail is compounded, it may be subjected to sterility testing on agar plates using conventional methods (approximately 16 hours). The cocktail may be further formulated to an acceptable titer, (e.g., to a titer of $5 \times 10^9$ pfu/ml of phage particles) in a pharmaceutically acceptable dosage, as deemed appropriate by the attending physician for administration to the patient.

Alternatively, as discussed herein, in another embodiment, CsCl density gradient purification may be performed using conventional methods on phages in the Tier 1 library, prior to, and thus simplifying, the production process after a therapeutic phage cocktail for a subject has been identified.

In a particular embodiment, it is contemplated that the phage cocktails of the instant invention may contain any number of individual phages. In a particular embodiment, the cocktail may comprise less than 10 individual phages. In other embodiment, the cocktail may comprise from about 10-15 phages.

In a particular embodiment, with respect to manufacturing personalized therapeutic cocktails, the so called scale-up for industrial production does not necessarily involve the large scale production of phages similar to the large scale GMP production of antibiotics, e.g., the production of hundreds of liters of a phage lysate. Instead, with regard to the instant invention, the concept of scale-up for industrial applications involves the increase in the number of personalized therapeutic cocktails that can be compounded simultaneously.

In a particular embodiment, it may be possible that a personalized therapeutic cocktail could show clinical efficacy on another patient's bacterial infection. In such a case, the phage cocktail in question, when applied to a second or third party patient, may be manufactured in the infectious bacteria of that second or third party and/or permissible domesticated manufacturing strains, as needed, according to the methods of the instant invention.

Compositions and Methods of Treatment:

The phage cocktails of the instant invention, in a pharmaceutically acceptable dosage form, are administered to a subject in a manner as deemed appropriate by an attending physician. Thus, in another aspect, the instant invention relates to compositions, including pharmaceutical compositions, comprising phage cocktails compounded according to the methods of the instant invention. In particular embodiments, the compositions are therapeutically effective phage cocktails of very high titer and very high purity, or of high titer and high purity, which are not found in nature. Indeed, it is contemplated herein that the phage cocktails produced according to the methods of the instant invention are particularly effective when compared to conventional therapeutic phage cocktails, and can reliably and rapidly provide therapeutically effective synergistic lytic effects on bacterial pathogens. Thus, methods of the instant invention may be used to design phage cocktails unique in composition as well as uniquely effective compared to compositions made according to conventional methods.

Moreover, as discussed above, while the methods of the instant invention may be used to formulate a personalized phage cocktail, it is contemplated herein that the cocktail could also be used to treat other individuals infected with the same or very similar bacterial strain(s). Thus the method of the instant invention may be used to generate phage cocktails that have broad therapeutic use.

As used herein, the term "composition" encompasses "phage cocktails" as disclosed herein, and includes, but is not limited to, pharmaceutical compositions comprising a plurality of purified phages.

"Pharmaceutical compositions" are familiar to one of skill in the art and typically comprise active pharmaceutical ingredients formulated in combination with inactive ingredients selected from a variety of conventional pharmaceutically acceptable excipients, carriers, buffers, diluents, etc. The term "pharmaceutically acceptable" is used to refer to a non-toxic material that is compatible with a biological system such as a cell, cell culture, tissue, or organism. Examples of pharmaceutically acceptable excipients, carriers, buffers, diluents etc. are familiar to one of skill in the art and can be found, e.g., in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable additional components included in the pharmaceutical compositions of the instant invention may vary, e.g., depending upon the desired route of administration and desired physical state, solubility, stability, and rate of in vivo release of the composition.

As contemplated herein, the phage cocktails of the instant invention, and particularly pharmaceutical compositions of the instant invention, comprise an amount of phage in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, e.g., approximately 0.5 ml. In another embodiment, up to 10 ml may be delivered in conjunction with a saline IV.

For administration by intravenous, cutaneous, subcutaneous, or other injection, a pharmaceutical formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art. For example, as discussed in Example 5 and depicted in FIG. 19, data indicate that the isotonic properties of Ringer's solution make a suitable buffer for phage cocktails, while "SM buffer" is typically used by one of skill in the art for phage dilution and storage. Of particular interest with phage therapeutics is the removal or limitation of host bacterial components from the phage cocktail preparation that may have deleterious affects on the host, which include but are not limited to LPS, peptidoglycan, bacterial toxins, and bacterial DNA. Therapeutic cocktail preparations can be designed to contain these kinds of materials in amounts below acceptable limits.

Methods of formulating pharmaceutical compositions are familiar to one of skill in the art. Notably, however, as discussed above, selection of phage for compounding in a phage cocktail can be counterintuitive. As provided by the methods of the instant invention, anticipating the bacterial changes that occur during infection or phage predation often calls for the inclusion of phage that cannot infect the parent strain of the infection. These phages infect the emergent strains during the infection and allow intelligent synergistic cocktails which show efficacy as a therapeutic despite not infecting the parent strain of the infection. Thus, it is contemplated herein that in a particular embodiment, a phage cocktail of the instant invention may comprise one or more phages that cannot detectably infect a parent strain of the bacterial pathogen causing infection in a subject, but can infect emergent bacterial strains which arise during the infection.

In another embodiment, it is contemplated herein that a therapeutic phage cocktail may stress the emergent bacterial strains such that the emergent bacterial strains regain sensitivity to one or more drugs, including antibiotics.

In another aspect, the present invention relates to methods of treating a bacterial infection comprising administering to a subject in need thereof an effective amount of a phage cocktail (or a pharmaceutical composition comprising an effective amount of a phage cocktail) compounded according to the methods of the instant invention.

As understood herein, a "subject in need thereof" includes any human or animal suffering from a bacterial infection, including but not limited to a multidrug resistant bacterial infection. Indeed, while it is contemplated herein that the methods of the instant invention may be used to target a specific pathogenic species, the method can also be used against essentially all human and/or animal bacterial pathogens, including but not limited to multidrug resistant bacterial pathogens, so long as the reagents (bacterial diversity set and/or phage libraries) exist for each said bacterial pathogen. Thus, in a particular embodiment, by employing the methods of the present invention, one of skill in the art can design and create personalized bacteriophage cocktails against many different clinically relevant pathogens, including multi MDR bacterial pathogens.

As understood herein, terms such as "effective amount" and "therapeutically effective amount" of a pharmaceutical composition of the instant invention, refer to an amount of a composition suitable to elicit a therapeutically beneficial response in the subject, e.g., by eradicating a bacterial pathogen in the subject and/or altering the virulence or antibiotic susceptibility of surviving phage-resistant bacterial pathogens and/or by providing an added benefit when a phage cocktail compounded according to the methods of the instant invention is simultaneously administered with either effective and/or ineffective antibiotics. Such response may include e.g., preventing, ameliorating, treating, inhibiting, and/or reducing one of more pathological conditions associated with a bacterial infection. One of skill in the art will appreciate that it is desirable that the initial dose of a phage cocktail of the instant invention be sufficient to control the bacteria population before it reaches a lethal threshold. Animal models suggest that $10^9$ to $10^{11}$ pfu/ml phage particles per dose would likely be the maximum dosage tenable based on protein load presented acutely to the liver in an adult (which would be scaled down in a pediatric population, i.e., EU limited $10^5$ dosing discussed in the below examples). It is suspected that this is a sufficient acute bolus to reduce the bacterial burden sufficiently to potentiate an immune response. Notably, phage "viremia" may be measured in the blood after administration. Animal models suggest that viremia is quite transient given the host immune response and sequestration in the reticuloendothelial system (liver and spleen).

Suitable effective amounts of the compositions of the instant invention can be readily determined by one of skill in the art and can depend upon the age, weight, species (if non-human) and medical condition of the subject to be treated. In addition, one of skill in the art will appreciate that the type of infection (e.g., systemic or localized), and the accessibility of the infection to treatment may also impact the dosage amount that is deemed effective. One of skill in the art will appreciate that initial information may be gleaned in laboratory experiments and an effective amount of a phage cocktail for humans subsequently determined through dosing trials and routine experimentation.

It is contemplated herein that the compositions of the instant invention may be administered to a subject by a variety of routes according to conventional methods, including but not limited to systemic, parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Administration can also be by continuous infusion or bolus injection.

In addition, the compositions of the instant invention can be administered in a variety of dosage forms. These include, e.g., liquid preparations and suspensions, including preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the compositions of the instant invention are administered to a subject as an injectable, including but not limited to injectable compositions for delivery by intramuscular, intravenous, subcutaneous, or transdermal injection. Such compositions may be formulated using a variety of pharmaceutical excipients, carriers or diluents familiar to one of skill in the art.

In another particular embodiment, the compositions of the instant invention, and/or pharmaceutical formulations administered in conjunction therewith, e.g., antibiotics, may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the active agent, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. Where appropriate, compositions for use with the methods of the instant invention may also be lyophilized and may be delivered to a subject with or without rehydration using conventional methods.

As understood herein, the methods of the instant invention comprise administering the compositions of the invention to a subject according to various regimens, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount may be administered to a subject as a single dose, a series of multiple doses administered over a period of days, or a single dose followed by one or more additional "boosting" doses thereafter. The term "dose" or "dosage" as used herein refers to physically discrete units suitable for administration to a subject, each dosage containing a predetermined quantity of the active pharmaceutical ingredient calculated to produce a desired response.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular composition. As understood by one of skill in the art, a "boosting dose" may comprise the same dosage amount as the initial dosage, or a different dosage amount. Indeed, when a series of doses are administered in order to produce a desired response in the subject, one of skill in the art will appreciate that in that case, an "effective amount" may encompass more than one administered dosage amount.

Kits and Articles of Manufacture

It is contemplated herein that the phage cocktails and/or one or more other compositions or reagents disclosed herein may be provided to a user (e.g., a clinician treating a subject with a MDR bacterial infection) in the form of a kit or other article of manufacture. Kits comprising pharmaceuticals or other agents or items for clinical use are familiar to one of skill in the art. Such kits may take many forms; typically, they comprise one or more packaging containers designed to safeguard the integrity and viability of the contents during transit and/or storage. In a particular embodiment, a kit of the instant invention may comprise one or more phage cocktails and/or one or more other reagents produced according to the methods of the instant invention, and may further comprise one or more additional reagents or items for use therewith, e.g., buffers, diluents, etc. as well as instructions or other information describing and/or facilitating the administration of the kit contents. In various embodiments, in addition to active pharmaceutical ingredients, excipients, diluents, buffers, etc. the kits of the instant invention may comprise various articles or medical devices made from a variety of pharmaceutically acceptable materials or reagents for facilitating treatment of a subject. These include, but are not limited to, vials, syringes, IV bags, etc.

As explained in the examples provided below, reagents and methods disclosed herein have been used to generate phage cocktails against *A. baumannii*, methicillin-resistant *Staphylococcus aureus* (MRSA), vancomycin-resistant Enterococci (VRE), and *Pseudomonas*. Notably, according to the methods of the instant invention, characterizing the actual mechanisms of action behind phage efficacy against a bacterial pathogen is not necessary in order to design therapeutically effective synergistic compositions; indeed, the methods of the instant invention can be used to rapidly find phage lytic synergy without needing to know the underlying mechanism for this synergy.

The phage cocktails of the instant invention maybe administered to a patient alone, or in combination with one or more pharmaceutical agents in any manner or dosing regimen, e.g., before, after, or concomitantly with one or more other pharmaceutical or other therapeutic agent. Indeed, in a particular embodiment, optimal therapy may comprise the integration of bacteriophage therapy coupled to antibiotics and source control (if possible) in parallel with optimization of the host immune function. As understood by one of skill in the art, "source control" refers to treating the infection directly at the source of the infection in the subject, i.e., before the infection spreads systemically. As discussed above, in addition to exploiting bacteriophages for direct bacterial lysis, bacteriophages may act synergistically with antibiotics in vivo, while potentiating reversion of bacterial susceptibility to antibiotic classes. Data such as these is provided herein in the below examples.

Thus it is contemplated herein that administration of a therapeutic phage cocktail may stress the emergent bacterial strains such that the emergent bacterial strains regain sensitivity to one or more drugs, e.g., an antibiotic to which it previously demonstrated resistance. In addition, it is further contemplated herein that phage cocktails of the instant invention may be administered to a subject concurrently with one or more antibiotics or other drugs to enhance overall therapeutic efficacy, e.g., to produce a synergistic therapeutic effect. Thus, it is contemplated herein that phages, and specifically the phage cocktails of the instant invention, may act synergistically with antibiotics, and/or potentiate reversion of pathogen susceptibility to antibiotic classes.

It is contemplated here that the use of the reagents disclosed herein, including the tiered phage libraries combined with a high throughput assay and an iterative screening process is a significant improvement over prior art. Simply using even a modest phage library to differentially compound either random or intelligently designed cocktails, in an attempt to find potentially therapeutic cocktails against a targeted bacterial pathogen would be a significantly laborious undertaking, as the vast majority of such cocktails would fail to meet therapeutic potential and one may never actually find a cocktail that shows therapeutic potential in this manner as potentially therapeutic cocktails against any given bacterial strain are expected to be exceedingly rare. Identifying synergistic cocktails would be even more dubious. In contrast, the iterative screening method of the instant invention essentially eliminates the need to screen numerous cocktails, the vast majority of which will fail to produce therapeutic potential. Instead, it is contemplated herein that the iterative screening method of the instant invention can provide the systematic and direct compounding of targeted cocktails, and specifically can provide the reliable production of synergistic cocktails containing phages with no detectable activity against the targeted pathogen on their own. The iterative screening method is also particularly feasible given the specific use of a liquid-based high throughput assay according to the methods of the instant invention. Thus the method of the instant invention provides a unique workflow, resulting in the reliable production of rare and counterintuitive cocktails that show therapeutic potential against any bacterial pathogen for which there exists a bacterial diversity set and a tiered phage library.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

It is understood herein that bacterial diversity sets and tiered phage libraries against various bacterial pathogens are currently being developed. That said, the examples provided below demonstrate the successful application of various reagents and steps of the method of the instant invention, and thus support the instant invention. As one of skill in the art will appreciate, all materials and reagents mentioned in the below examples are available from a variety of commercial vendors unless indicated otherwise. Conventional methods may be employed unless indicated otherwise.

Example 1

High Throughput Phage Efficacy Assay

A possible high throughput phage efficacy assay that may be used with the methods of the instant invention is described below. The method provided herein is an extension of a previously reported technique (Henry M, et al. Bacteriophage 2012; 2:159-67.) Specifically, the previously reported assay on its own is simply a high throughput means of identifying the hold-times of individual phages and/or phage cocktails. The method of the instant invention links this high throughput assay to characterized phage libraries and iterative rounds of screening and cocktail formulation, enabling the entire workflow to identify synergistic cocktails and reliably identify those phages that individually have no detectable effect on the targeted bacteria, but still possess critical therapeutic potential as a component of a synergistic cocktail, due to their ability to target phage-resistant subpopulations; allowing for the rapid compounding of such synergistic cocktails without the need to wastefully screen randomly generated cocktails, most of which will fail to have therapeutic potential. Apart from the instant invention, the therapeutic potential of such seemingly ineffective phages would go unidentified. Additionally, linking this high throughput assay to precharacterized libraries, allows for the rapid formulation and interrogation of phage cocktails, and whose therapeutic potential is determined solely on the performance of these differentially compounded cocktails, eliminating the need to have any a priori knowledge of a an infectious bacterium's phage susceptibility or the need to determine the mechanism of a synergistic cocktail against said bacterium, or the need to determine the receptors used by each phage in the cocktail.

Traditionally, one would seek to develop a phage cocktail using phages with different receptors, necessitating the need to first identify the receptor of each phage. The high throughput assay, linked to large and diverse characterized libraries described herein, eliminates this need.

It is contemplated herein that the assay may be used to identify and generate an effective therapeutic phage cocktail as well as to confirm the specificity, sensitivity, and sterility of phages prior to release as a therapeutic product.

The assay is based on the interaction between lytic phage and bacteria in a liquid environment. In this liquid assay system, tetrazolium dye is added with media. During active growth of bacteria, cellular respiration reduces the tetrazolium dye and produces a color change that is captured by a camera. In this system as many as 400 phage efficacy assays in the presence of a targeted bacterium can be performed simultaneously but separately, thus allowing monitoring of the kinetics of bacterial growth and the development of resistance over the course of the experiment. The interpretation of such phage-bacterial interaction data in liquid environment permits the selection of phages that are highly virulent against the given bacteria, evidenced by a hold-time of at least 4 hours. Further selection of these phages for cocktail preparation is evaluated using the same liquid assay in the presence of various mixtures of these virulent phages.

One of skill in the art will appreciate that different bacterial species may replicate at different rates, i.e., some bacteria grow more slowly than others. Thus, growth hold times observed with phage efficacy assays may vary. Generally, for use in the methods of the instant invention, the lack of appearance of phage resistant bacteria after about 20 hours of incubation at 37° C. indicates high therapeutic potential for a phage cocktail, however, hold-times ranging from about 16 to about 48 hours may also be used to evaluate efficacy in this regard. In particular embodiments, it is contemplated herein that growth hold-times of about 15, 16, 17, 18, 19, and 20 hours may also suggest efficacy according to the methods of the instant invention.

Ideally, the assay is performed at 37° C. (or thereabouts) for selecting therapeutic phages for use in human subjects since that is typically the temperature of the human body, and evaluating the phage/bacterial interaction at this same temperature is preferred. Of course, it is possible that the assay may be performed at other temperatures, depending on the typical body temperature of the subject to be treated.

Preparation of Phage Stocks for Phage Efficacy Assay:

All phages to be tested according to this growth efficacy assay are plaque purified, e.g., at least two times, and propagated on their specific host. Phage lysates are prepared according to conventional methods. See, e.g., Sambrook et. al. 1989. Molecular Cloning: A Laboratory Manual. 2nd ed. Col Spring Harbor Press, Cold Spring Harbor, N.Y. All phage stock-lysates are filter sterilized, e.g., by passing through 0.22 micron filters (Millex-GV, Millipore) for phage efficacy assay analysis.

Growth Media:

In a particular embodiment, trypticase soy (TS) broth (Becton Dickenson, N.J.) containing 10% tetrazolium dye (Biolog, CA) is used in a micro-titer plate (96 well serocluster, styrene, flat bottom, (Biolog, CA)) as the propagating media for the bacterial strains and phages. Phages are diluted separately or as mixtures in this broth as required for the test and inoculated with respective bacterial isolates.

Preparation of Bacterial Inoculum:

Bacterial isolates, including bacterial isolates obtained from clinical specimens may be tested using this assay. If need be, all bacterial isolates may be purified of infecting prophages, conversely, they may also be used as is. However, the bacterial isolates are colony-purified, e.g., at least two times on TS-agar plates. From TS-agar plates, 6 to 12 bacterial colonies are harvested within 18 to 24 hours of growth and suspended in 5-mL polypropylene tubes containing 2 mL of physiological saline solutions (0.9% sodium chloride, Irrigation, USP, Abbott Laboratories). The visual index of bacterial suspension is adjusted to 0.5 McFarland (McF) units. Optical density determinations are performed with a Vitek Colorimeter (HACH Company, Vitek Special DR100 Colorimeter, product #52-1210). Before measurement, each tube is vortexed to suspend bacteria. The meter is standardized to 0% light transmission with a crystal violet dye and to 100% with a tube of saline solution. A reading of 80-88% on this meter corresponds to an optical density comparable to 0.5 McF. The average titers of different bacterial strains are $10^8$ cfu/mL at 0.5 McF units. These adjusted stocks are further diluted on TS growth media (1/10th dilution), and 10 μl of these suspensions (approximately $10^5$ cfu) are used in wells of microtiter plate. For example, bacterial concentrations in each well under columns 1, 2, 3, 4, 5, 6, 7 and 9 in FIG. 1 will be $10^5$ cfu/mL.

Preparation of Serial Dilutions of Phage:

Test phages are serially diluted to make working concentrations of phage stocks. The concentration of the phage stocks are adjusted to obtain $2 \times 10^8$ plaque forming units (pfu)/ml. From the $10^8$ pfu/mL of stock, phages are serially diluted to 10 pfu/mL by transferring 10 μl of diluted phage (from each previous dilution) and mixing it with 90 μl of TS media in micro-titer plates (described below).

Dilution on Micro-titer Plate:

FIG. 1 depicts an example of a sample distribution of micro-titer plate wells for a possible lytic spectrum study of phage (test setup). Separate phage strains are added in column 1 to a total of $10^7$ pfu per well, which will produce an approximate 1000× Multiplicity of Infection (MoI), e.g., 1000:1. The phage from column 1 will then be serially diluted 10-fold to column 7 to a final MoI of 0.001:1. Control wells are located in columns 8 through 10 to assess sterility of the media and phage. Additionally column 10 provides for an unadulterated bacterial growth curve for the host strain. Columns 11 and 12 serve as wells to be used for diluting the bacterial host strain to achieve the proper inoculating concentration of $10^4$ cfu per well. In this assay, interaction of phage and different bacterial strains at MOIs of 10, 1, 0.1, 0.01, 0.001 and 0.0001 are evaluated in separate wells. Initially, 90 μL of TS-growth media is dispensed in all wells under column 1 to 11. Next 10 μL of phage stock (concentration $10^8$ pfu/ml) is dispensed in each well of columns 1 and mixed thoroughly. Then $10^7$, $10^6$, $10^5$, $10^4$, $10^3$, and $10^2$ pfu/mL phages in TS-growth media are prepared by serial dilution of transferring 10 μL of diluted phage (from each previous dilution) and mixing it with the 90 μL of TS-growth media in the micro-titer plate. Moreover, 10 μL of $2 \times 10^8$ pfu/mL phage stock is dispensed in each well under column 8. Additionally, in each well of columns 9, 10 and 11, 90 μL of TS-growth media is dispensed to prepare bacterial dilution for inoculums. 100

μL of bacterial inoculum (0.5 McF) is distributed in each well under column 12. 10 μL inoculums from these wells are transferred to wells under column 11 and mixed thoroughly by using a multi-channel electronic pipette (Rainin Instrument Co. Inc., EDP-Plus™ M8 250 μL pipette, Product # C03486) to prepare bacterial inoculum. 10 μL of these diluted inoculums (under column 11) are used to sequentially inoculate the wells under columns 9, 7, 6, 5, 4, 3, 2 and 1. The micro-titer plate is covered with sterile lids for 96-well microtiter-plates (Costar Catalog#3096) and incubated at 37° C. for about 18-24 hours in a Biolog device (Biolog, Inc, Hayward, Calif.) to monitor bacterial growth in presence of phage/phages. Plate is shaken gently prior to incubation for proper mixing of the contents.

Example 2

"Personalized" Therapeutic Cocktail of Wild Environmental Phages Rescues Mice from *A. baumannii* Wound Infections This example describes the isolation and compounding of a five member cocktail of wild or natural phages against *A. baumannii* and provides data which demonstrate therapeutic efficacy in a mouse full-thickness dorsal infected wound model.

Materials and Methods:

Bacterial Strains and Culture Conditions:

Two strains were used to isolate phages in this study. *A. baumannii* AB5075 is a previously described clinical strain isolated at Walter Reed Army Medical Center (Jacobs, A. C. et al (2014) MBio May 27; 5(3):e01076-14). AB5075 Passaged (AB5075P) was isolated after passage of AB5075 in our mouse wound model for 14 days (Thompson, M. G., et al. (2014). Antimicrob Agents Chemother 58(3): 1332-1342). The re-isolated AB5075 showed mixed colony morphology on Lennox LB agar (Becton, Dickinson and Company, Sparks, Md.) of opaque (wild type) and translucent colonies. A colony that displayed translucent morphology was chosen as a second target strain for phage isolation, and was designated AB5075P. In order to visualize wound bacterial burden during animal studies, the bioluminescent strain AB5075 attTn7::luxCDABE (AB5075::lux) was created. Briefly, a Tn7 plasmid containing the lux operon luxCDABE, pUC18T-mini-Tn7T-hph-lux, was introduced into AB5075 via conjugation (Kumar, A., C. (2010). J Microbiol Methods 82(3): 296-300), and integration of the lux operon into the chromosome at the attTn7 site was confirmed via PCR. Additionally, two Tn5 isogenic AB5075 mutants, AB5075 epsA::Tn5 and AB5075 ptk::Tn5, were used in several in vitro assays (Jacobs, A. C. et al (2014) MBio May 27; 5(3):e01076-14).

*A. baumannii* strains used to assess differences in host infectivity of phages AB-Navy1-4 are genetically diverse strains that were obtained from our Wound Infections culture collection and were originally received via the Army Multidrug-resistant Organism Repository and Surveillance Network (MRSN) and the Navy NAMRU-6. MDR *A. baumannii* clinical isolates used to assess phage cocktail specificity are military-relevant clinical isolates from wounded service members, and were isolated from Landstuhl Regional Medical Center, National Navy Medical Center, and Walter Reed National Military Medical Center between 2003 and 2010 during the height of the conflicts in Afghanistan and Iraq (Heitkamp, R et al., The ISME Journal [Manuscript #ISMEJ-16-00384OA], "Differential phenotypic diversification in antagonism among clinical strains of *Acinetobacter*" in review). Strains were maintained on tryptic soy broth (TSB; Becton, Dickinson and Company) or Lennox LB broth (Becton, Dickinson, and Company), and stored in 20-40% glycerol at −80° C.

Isolation of Phage Strains from Environmental Sources:

*A. baumannii* phages were isolated from raw sewage water harvested from the Seneca Wastewater Treatment Plant located in Germantown, Md. Briefly, powdered TSB medium (Becton, Dickinson and Company) was mixed with raw sewage to a final concentration of 3% w/v. AB5075 or AB5075P was grown to exponential phase, and 1 mL of each strain was added to 100 mL aliquots of TSB-sewage mixture. The *A. baumannii*-inoculated TSB-sewage mixture was incubated at 37° C. and 250 rpm overnight. The following day, 1 mL of the infected TSB-sewage mixture was harvested and centrifuged at 8,000×g for 5 min to pellet cells and debris. The supernatant was transferred to a sterile 0.22 μm Spin-X® centrifuge tube filter (Corning, N.Y.), and centrifuged at 6,000×g to remove any remaining bacteria. A 10 μL aliquot of the filtrate was mixed with 100 μL of exponential growth culture of AB5075 or AB5075P, incubated at 37° C. for 20 min, mixed with 2.5 mL of molten top agar (0.6% agar) tempered to 50° C., and poured over TSB agar plates (1.5% TSB agar). Plates were incubated overnight at 37° C., and subsequent phage plaques were individually harvested and purified three times on appropriate *A. baumannii* isolates using the standard procedures described by Sambrook et al. (Sambrook, J., E. F. Fritsch and T. Maniatis (1989). "Molecular Cloning: A Laboratory Manual. 2nd ed." Col Spring Harbor Press, Cold Spring Harbor, N.Y.)

Propagation and Purification of Phage Strains:

High-titer phage stocks for in vivo experimentation were propagated and amplified in corresponding host bacteria by standard procedures (Merril, C. R., B. et al (1996) Proc Natl Acad Sci USA 93(8): 3188-3192). Large-scale phage preparations were purified by cesium chloride density centrifugation as previously described (Biswas, B., et al (2002) Infect Immun 70(1): 204-210), and filtered through a 0.22 μm filter (Millipore Corporation, Billerica, Mass.) prior to treatment of animals. Phage stocks were stored at 4° C. indefinitely.

Electron Microscopy:

Standard methods of sample preparation were employed for transmission electron microscopy (TEM) and scanning electron microscopy (SEM). For both methods, samples were fixed in 4% paraformaldehyde with 1% glutaraldehyde in 0.1 M sodium cacodylate buffer. For TEM, the fixed and inactivated high-titer phage samples were spread on a copper grid, washed with water and negatively stained with uranyl acetate. These samples were imaged in a FEI Tecnai™ T12 Spirit TEM at 100 kV.

For SEM, fixed Tegaderm™ samples were washed three times with 0.1 M sodium cacodylate buffer, post fixed with 1% osmium tetroxide in buffer and then 0.5% uranyl acetate in water. The samples were subsequently dehydrated through an ethanol series, critically point dried and coated with gold-palladium. The coated SEM samples were imaged in an FEI Quanta 200 FEG SEM at 5 kV.

High-throughput Liquid Lysis Assay to Determine Host Infectivity and Cocktail Synergy:

An automated, indirect, liquid lysis assay described in Example 1 was used to evaluate the activity of phages against *A. baumannii* strains. Briefly, an overnight culture of each strain was inoculated into the wells of a 96-well plate containing TSB mixed with 1% v/v tetrazolium dye. Phages were added to each well, and plates were incubated in an OmniLog™ system (Biolog, Inc., Hayward, Calif.) at 37° C. overnight. The tetrazolium dye indirectly measures the respiration of the bacterial cells. Respiration causes reduction of the tetrazolium dye, resulting in a color change to purple. The color intensity of each well is quantified as relative units of bacterial growth. For host infectivity determination, bacteria were inoculated at $10^5$ colony forming units (CFU) per well and phage were added at a concentration of $10^6$ plaque forming units (PFU) per well for an MOI of 10. For cocktail synergy studies, bacteria were inoculated at $10^6$ CFU per well and phage were added at a concentration of $10^8$ PFU per well for an MOI of 100.

Efficiency of Plating for Phages on the Host Strain:

To determine how well each phage infected its original host strain, a dilution series spot plate assay was used to observe plaque formation (Sambrook, J., E. F. Fritsch and T. Maniatis (1989). "Molecular Cloning: A Laboratory Manual. 2nd ed." Col Spring Harbor Press, Cold Spring Harbor, N.Y.). To do so, 50 µL of an overnight culture of each A. baumannii strain was used to individually inoculate 5 mL of molten top agar tempered to 55° C. The inoculated agar was mixed thoroughly by brief vortexing and then spread over square LB agar plates. Top agar was allowed to set for approximately 45 min, at which time 4 µL aliquots of $10^{10}$ to $10^2$ PFU in 10-fold dilutions of each phage were spotted on the surface. Spots were allowed to fully absorb into the top agar, after which plates were incubated at 37° C. for 24 hours, and plaque formation was assessed.

Time-kill Analysis of A. baumannii AB5075 Treated with Phages:

Time-kill experiments were used to provide a quantitative analysis of phage bactericidal activity. Briefly, an overnight culture of AB5075 was diluted 1:1000 in fresh LB broth to a final concentration of ~$1\times10^6$ CFU per mL. Twenty mL aliquots were then transferred to 250 mL Erlenmeyer flasks and incubated at 37° C. with shaking at 200 rpm for 2 hours. Samples were then challenged with either $2\times10^{11}$ PFU per mL of AB-Army1 or an equal volume of sterile phosphate buffered saline (PBS) and returned to incubation as previously described. One hundred µL aliquots were taken at 0, 2, 4, and 24 hours, serially diluted in PBS, and plated on LB agar. Plates were incubated at 37° C. for 24 hours and subsequently enumerated.

Raman Spectroscopic Analysis of A. baumannii Strains:

Changes in AB5075 strains due to phage exposure were monitored using Raman spectroscopy. Each sample was obtained from LB agar plates and was directly transferred into a disposable weigh dish for spectral collection. Raman spectra were collected using an 830 nm Raman PhAT system (Kaiser Optical Systems, Inc., Ann Arbor, Mich., USA). Spectra were collected using a 3 mm spot size lens with 100 sec total acquisition time and 1 mm spot size lens with 100 sec total acquisition time for time-kill assay samples. Spectra were then preprocessed by baseline removal using a sixth order polynomial and intensity normalization to the 1445 $cm^{-1}$ Raman vibrational band prior to analysis.

Assessment of A. baumannii Virulence in a Galleria mellonella Worm Model:

Colonies of AB5075 bacteria previously exposed to AB-Army1 phages display a translucent phenotype similar to A. baumannii epsA and ptk capsule mutants known to be attenuated for virulence (Luke, N. R. et al (2010) Infect Immun 78(5): 2017-2023; Russo, T. A., et al (2010) Infect Immun September; 78(9):3993-4000. doi: 10.1128/IAI.00366-10. Epub 2010 Jul. 19). To determine if AB5075 previously exposed to AB-Army1 phage is attenuated, we assessed bacterial virulence in a wax worm model of infection (Peleg, A. Y. et al (2009) Antimicrob Agents Chemother 53(6): 2605-2609). A. baumannii strains were grown to exponential phase, washed in PBS, and resuspended in PBS to ~$1\times10^7$ CFU per mL. Galleria mellonella worms (Vanderhorst, Inc., St. Marys, Ohio) in the final-instar larval stage and between 200 and 300 mg were inoculated with 5 µL of resuspended bacteria into their last left proleg using a 10 µL Hamilton syringe (Fisher Scientific, Pittsburgh, Pa.). After infection, worms were incubated in plastic petri dishes at 37° C., and monitored for death over 5 days. Worms were considered dead when they displayed no movement in response to tactile stimuli.

Efficacy of Phages as a Therapeutic in an A. baumannii Mouse Wound Model:

Phage treatment was assessed in a previously described mouse wound model (Thompson, M. G., et al. (2014). Antimicrob Agents Chemother 58(3): 1332-1342), with some modifications. Briefly, 6-week-old female BALB/c mice were rendered neutropenic via cyclophosphamide injection, backs shaved, and a full-thickness wound was created on their dorsal side. Each wound was inoculated with ~$5\times10^4$ CFU of AB5075::lux, and a Tegaderm™ bandage was placed over the wound. Mice were single-housed from day 0 (inoculation) through day 6. For phage treatments, mice received $4\times10^9$ PFU of phages in PBS via IP injection, and $5\times10^9$ PFU of phages in PBS topically under the Tegaderm™ dressing, on top of the wound. Treatments were given simultaneously at 4, 24, and 48 hours post-infection. On day 3 post-infection, each Tegaderm™ covering was removed and wounds remained exposed to air for the remainder of the experiment. Select Tegaderm™ coverings were submitted for scanning electron microscopy (SEM) to compare biofilm formation among treatment groups. Mice weight and clinical scores were monitored and recorded through day 6 of the experiment. An IVIS® in vivo imaging system (PerkinElmer, Waltham, Mass.) was used to measure the bioluminescent signal of AB5075::lux as a means to visualize and perform relative quantification of bacterial burden in the wound bed over the course of the experiment. To do so, mice were anesthetized with isoflurane gas and placed dorsal side up, inside the IVIS® chamber. Bioluminescence measurements were taken with exposure times of 1 sec, 5 sec, and 10 sec on days 1, 3, and 5, respectively. Using Living Image® Software version 4.2 (PerkinElmer), pictures were analyzed and bioluminescence was quantified. To determine the average radiance, each wound was measured using a region of interest (ROI) of 2.8 $cm^2$. The area of bioluminescence was measured using the Auto ROI function with a threshold of 20%. The physical wound size was measured using a Silhouette wound measurement device (Aranz Medical Ltd., Christchurch, New Zealand) on days 3, 7, 9, and 13 post-infection.

Results:

Characterization of A. baumannii Phages Isolated from Sewage Water:

To develop and test a customized phage therapeutic for the treatment of an MDR A. baumannii wound infection, the model clinical isolate AB5075 was selected (Jacobs, A. C. et al (2014) MBio May 27; 5(3):e01076-14). This MDR A. baumannii strain has been used successfully in our murine wound model and causes a severe skin and soft tissue infection in mice (Thompson, M. G., et al. (2014). Antimicrob Agents Chemother 58(3): 1332-1342). In vitro cultures of A. baumannii AB5075 show mixed opaque and translucent colonies at a ratio of 100:1 (data not shown). Because wound healing is a lengthy process that likely exerts unknown selection pressures on A. baumannii, we passaged AB5075 in the aforementioned wound model and when reisolated chose a translucent colony to approximate a murine clinical isolate with rare colony morphology (see Materials and Methods). This passaged strain with a translucent morphology was chosen as a second target for phage isolation, and was named AB5075P. Lytic phages were then isolated from local sewage water using AB5075 or AB5075P as a host. From the AB5075 sewage water culture supernatant, one phage was isolated and designated AB-Army1 and produced clear point plaques (data not shown). Interestingly, immediately surrounding the AB-Army1 plaque there was a large zone of phenotypically distinct AB5075 compared to AB5075 in the adjacent lawn. Halos of this kind implicate a diffusible phage-encoded protein causing an enzymatic change to the surface of the bacteria, a well-recognized phenomenon of phages that infect capsular bacteria (Bessler, W., et al (1975) J Virol 15(4): 976-984; Sutherland, I. W. (1995) FEMS Microbiol Rev 16(4): 323-347; Hughes, K. A. et al (1998) J Appl Microbiol 85(3): 583-590; Hughes, K. A., et al I (1998) Microbiology 144 (Pt 11): 3039-3047; Linnerborg, M., A. et al (2001) Carbohydr Res 333(4): 263-269; Azeredo, J. and I. W. Sutherland (2008) Curr Pharm Biotechnol 9(4): 261-266; Cornelissen, A. et al (2011) PLoS One 6(4): e18597; Kassa, T. and S. Chhibber (2012) J Virol Methods 179(1): 135-141). An efficiency of plating assay showed that when a dilution series from $10^{10}$-$10^2$ of AB-Army1 was spotted on an overlay plate of AB5075, that AB-Army1 could infect at a concentration as low as $10^2$ PFU per mL. From AB5075P sewage water culture supernatants, four unique phages were isolated and designated AB-Navy1-4. All four phages displayed a gross morphology similar to each other but much larger than AB-Army1 and produced clear point plaques (data not shown). An efficiency of plating assay showed that when a dilution series from $10^{10}$-$10^2$ of all four individual phages was spotted on an overlay plate of AB5075P, that all four phages could infect at a concentration as low as $10^3$ PFU per mL. To demonstrate that AB-Navy1-4 were each unique, each was tested against a genetically diverse set of *A. baumannii* strains to compare host range using a Biolog system (Henry, M. et al (2012) Bacteriophage 2(3): 159-167). The host range of each phage was distinct, not only when comparing strains infected, but also the number of hours each phage could prevent growth of the bacterial host in liquid (hold time) (Table 1). Thus each of these phages to AB5075P appears to be unique.

TABLE 1

Host ranges of phages AB-Navy1-4 tested against a genetically diverse set of *A. baumannii* strains

|  | AB-NAVY1 | AB-NAVY2 | AB-NAVY3 | AB-NAVY4 |
| --- | --- | --- | --- | --- |
| Strain N0326 | 48 | 48 | 48 | 12 |
| Strain P0360 | DNI | DNI | 12 | 16 |
| Strain Q0683 | DNI | DNI | 6 | 22 |
| Strain Q0668 | 4 | DNI | 6 | DNI |
| Strain W0053 | 20 | 18 | 22 | 24 |
| W4448 | DNI | DNI | 16 | 12 |
| W4932 | 48 | 20 | 48 | 38 |
| W5256 | DNI | 36 | 38 | DNI |

Host infectivity is given in hours of hold time (i.e., time that the phage could prevent bacterial growth in liquid).
DNI = does not infect.

AB-Army1 infection leads to a putative loss-of-capsule phenotype in *A. baumannii* AB5075:

The infection of AB5075 with AB-Army1 was monitored in liquid cultures via a time-kill assay. In the absence of AB-Army1, AB5075 grows well with largely uniform opaque colony morphology indicative of capsule production. However, when AB-Army1 was present, the two hour time point had nearly a three log reduction in colony forming units (CFU) compared to the uninfected culture (Table 2). Additionally, 98% of the surviving AB5075 in the AB-Army1-infected culture now had translucent colony morphology at 2 hours, suggesting a loss of capsule production. It should be noted that phage were not inactivated or removed from the culture before plating, so phage infection and lysis could have occurred both in liquid and/or on the agar plate; however, lysis occurring under either circumstance would result in the same outcome observed here. In contrast, the uninfected AB5075 culture only showed a frequency of 2% translucent colonies at 2 hours (Table 2). The surviving translucent AB5075 in the AB-Army1-infected culture then grew over time, as indicated by the increase in CFU (titer) at the 4 and 24 hour time points (Table 2). This observed translucent morphology of AB5075 previously exposed to AB-Army1 is stable for at least 10 restreaks, and does not appear to be the transient phase variation observed by Tipton et al. (Tipton, K. A. et al (2015) J Bacteriol 197(15): 2593-2599). Because the AB-Army1-treated culture still contained phage and grew at 4 and 24 hours, we hypothesized that the translucent morphology of the surviving AB5075 was associated with insensitivity to the AB-Army1 phage. This phenomenon is consistent with selection for the loss of receptor and suggests the receptor for AB-Army1 is a capsule component.

TABLE 2

AB-Army1 phage infection leads to a putative loss-of-capsule phenotype in *A. baumannii* AB5075

| Time (hrs) | Treatment | % Capsule (+) | % Capsule (−) | Total CFU |
| --- | --- | --- | --- | --- |
| 0 | Untreated | 100% | 0% | 8.9E+06 |
|  | AB-ARMY1 | 99% | 1% | 8.2E+06 |
| 2 | Untreated | 98% | 2% | 2.2E+09 |
|  | AB-ARMY1 | 2% | 98% | 3.5E+06 |
| 4 | Untreated | 93% | 7% | 1.7E+10 |
|  | AB-ARMY1 | 3% | 97% | 6.1E+08 |
| 24 | Untreated | 85% | 15% | 1.3E+11 |
|  | AB-ARMY1 | 1% | 99% | 3.5E+11 |

When further investigated, it was confirmed that the translucent colony morphology observed in AB5075 previously exposed to AB-Army1, was similar to the colony morphology of isogenic AB5075 mutants harboring Tn5 insertions in genes known to be involved in capsule biosynthesis. The genes epsA and ptk are essential for capsule biosynthesis in *A. baumannii*, encoding for a putative polysaccharide export protein and protein tyrosine kinase, respectively (Luke, N. R. et al (2010) Infect Immun 78(5): 2017-2023; Russo, T. A., et al (2010) Infect Immun September; 78(9):3993-4000. doi: 10.1128/IAI.00366-10. Epub 2010 Jul. 19); Senchenkova, S. N. et al (2015) Carbohydr Res 408: 8-11). Notably, this translucent colony morphology was also similar to the translucent phenotype of AB5075P, the strain used to isolate phages AB-Navy1-4. When the host range of AB-Army1 and the AB-Navy1-4 phages was assessed against the capsule-positive AB5075 and the capsule-negative AB5075P, AB5075 epsA::Tn5, AB5075 ptk::Tn5, and a streak purified strain of AB5075 previously exposed to the AB-Army1 phage, AB-Army1 could only form plaques on capsule positive AB5075, while the AB-Navy1-4 phages could only form plaques on the capsule-negative strains. Thus it appears that exposure of AB5075 to AB-Army1 not only has a strong bactericidal effect, but also imposes a selection that results in a population of insensitive bacteria displaying a phenotype consistent with loss of capsule production by AB5075.

Raman Spectroscopy Links Capsule Changes Among Phage-treated and Untreated AB5075 Strains to Specific Spectral Features:

As a biophysical means to rapidly characterize the capsule-associated phenotypes we observed in our studies, Raman spectroscopy was used to interrogate changes in our *A. baumannii* strains. Analysis of Raman spectra revealed inherent spectral markers for encapsulated AB5075 strains (data not shown). Specifically, the Raman spectral band at 979 cm$^{-1}$ was only present in strains with opaque, capsule-positive colony morphology. The Raman spectral band at 979 cm$^{-1}$ was absent in the remaining strains which have a capsule-negative colony morphology (data not shown). Other spectral markers observed in the opaque strain of AB5075 included 1422 cm$^{-1}$ and 1379 cm$^{-1}$ (data not shown). While it is difficult to say precisely which cellular components in the bacteria the Raman spectral differences are attributed to, the distinct differences between wild type AB5075 and the translucent strains, particularly AB5075 epsA::Tn5 and AB5075 ptk::Tn5, clearly correlate changes in the 979 cm$^{-1}$ band with the changes in capsule phenotype. Raman spectral bands between 1300 cm$^{-1}$ and 1480 cm$^{-1}$ are largely attributed to CH$_2$ deformation and scissoring modes present in fatty acids (lipids) and molecules with long chains of methyl and methylene groups (proteins), known components of the bacterial cell surface (Naumann, D. (2001) FT-Infrared and FT-Raman Spectroscopy in Biomedical Research. Infrared and Raman Spectroscopy of Biological Materials. H. U. Gremlich, Yan, B. New York, CRC Press: 329-337; Socrates, G. (2004) Infrared and Raman Characteristic Group Frequencies: Tables and Charts. 3rd ed. New York John Wiley & Sons, Ltd.). The structure of the capsular polysaccharide in AB5075 has also recently been proposed and implicates the epsA and ptk loci for capsular polysaccharide biosynthesis specifically in AB5075 (Senchenkova, S. N. et al (2015) Carbohydr Res 408: 8-11).

Infection of *A. baumannii* AB5075 with Phages AB-Army1 and AB-Navy1-4 Leads to Effective Killing In Vitro:

The results above revealed that when AB5075 is exposed to AB-Army1 a selection for loss of receptor (capsule) occurs, resulting in a population of translucent colonies that are now sensitive to the AB-Navy1-4 phages. We hypothesized that the combination of all five phage into a single cocktail could result in a robust treatment that targets not only the original opaque AB5075 population, but also the emergent and capsule-negative AB-Army1-insensitive bacteria. To test this, a co-infection with the five-member phage cocktail, (i.e., AB-Army1+AB-Navy1-4) designated "AB Cocktail", was assessed in vitro against AB5075 by use of the method of Example 1.

Figure 2:
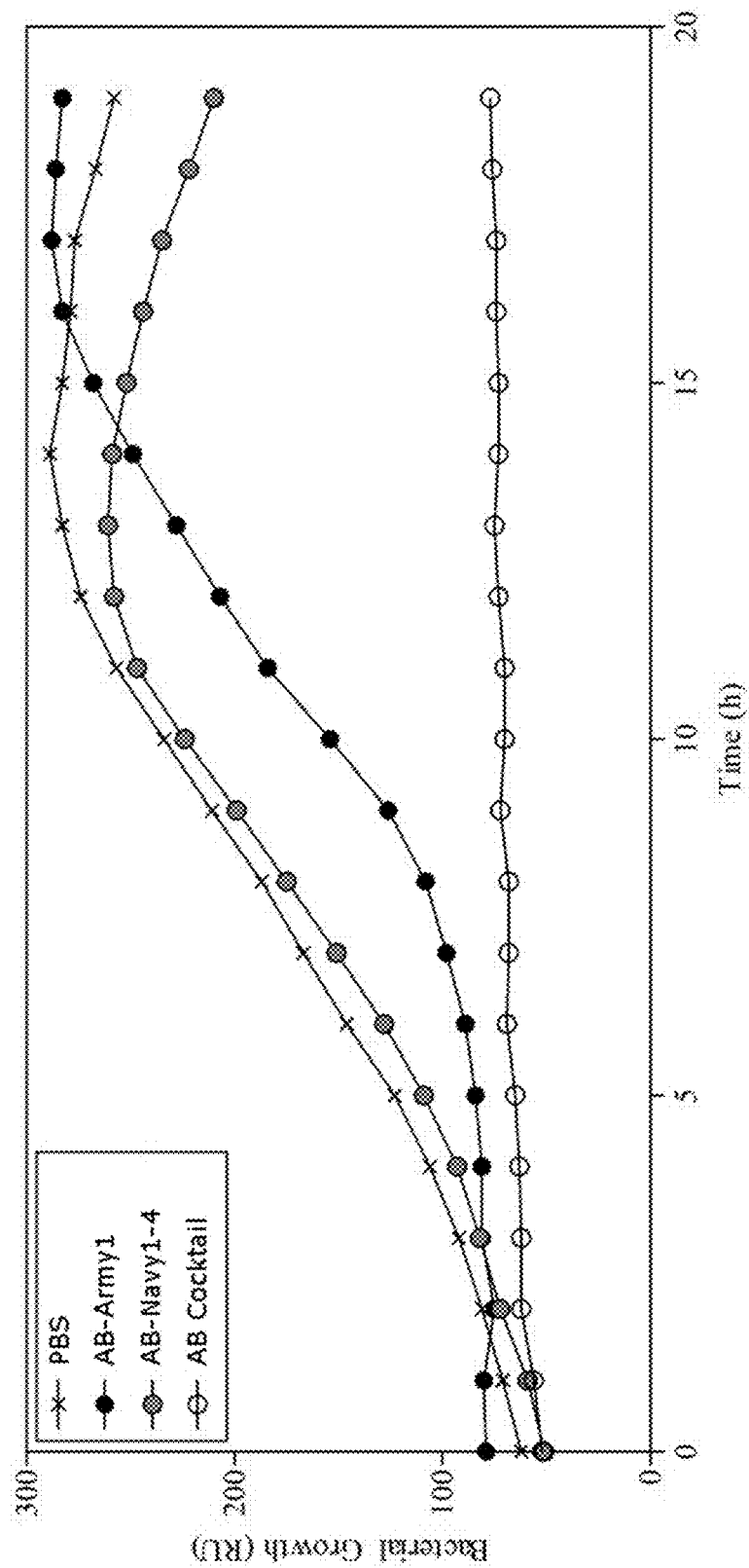
FIG. 2 depicts bacterial growth curves for bacteria AB5075 in the presence of phage as reported in Example 2. Bacterial growth hold time is indicated as the time when the curve stays flat. The X curve is growth of the bacteria alone in PBS. The black circles represent a curve depicting bacteria grown with just the phage directed to encapsulated bacterial cells (AB-Army1). The gray circles depict AB-NavyPφ1-4 which infects just the unencapsulated cells. The empty circles represent growth in the presence of the ABφ Cocktail (i.e., AB-Army1+AB-Navy1-4). Results indicate that infection of AB5075 with the five-member ABφ Cocktail results in complete killing in vitro. Treatment with AB-NavyPφ1-4 resulted in no change in growth compared to PBS-treated cells. AB-Armyφ1 infection resulted in an extended lag phase, due to the 99% killing of capsule-positive cells, and the eventual outgrowth of capsule-negative cells.

AB5075 cultures treated with only AB-Navy1-4 demonstrated similar growth kinetics to untreated controls (FIG. 2), further demonstrating that the encapsulated AB5075 is insensitive to these phages. The culture containing AB-Army1 showed a three hour lag in exponential growth, consistent with a selection event against encapsulated AB5075 and the following outgrowth of unencapsulated cells in the culture. However, cultures that contained the AB Cocktail showed complete growth inhibition over the course of the experiment (FIG. 2). Additionally, Raman spectra collected for each treatment at 0, 4, and 24 hours showed that the Biolog results were consistent with the loss of capsule observed in the time-kill experiments. AB5075 cultures that were untreated or treated with AB-Navy1-4 possessed the 979 cm$^{-1}$ Raman spectral band for all time-points, while AB5075 cultures treated with AB-Army1 or the AB Cocktail exhibited a greatly diminished 979 cm$^{-1}$ band at 4 and 24 hours. Thus there appears to be a combinatorial effect when all five phages are administered as a single therapeutic cocktail in vitro. To further assess the AB Cocktail activity, its infectivity against a panel of 92 MDR *A. baumannii* clinical isolates collected between 2003 and 2010 from wounded military personnel being treated at Landstuhl Regional Medical Center, National Navy Medical Center, and Walter Reed National Military Medical Center was tested. Again using the Biolog system, it was determined that the AB Cocktail infected 10 out of the 92 strains (data not shown), highlighting the specificity of the cocktail and thus the probable need for personalization when using phages therapeutically.

Virulence of AB-Army1-Treated AB5075 is Attenuated in a *Galleria mellonella* Model:

AB5075 bacteria previously exposed to AB-Army1 phage displayed a translucent phenotype similar to epsA and ptk capsule mutants. Because *A. baumannii* epsA and ptk mutants have been shown to be attenuated in an animal model (Russo, T. A., et al (2010) Infect Immun September; 78(9):3993-4000. doi: 10.1128/IAI.00366-10. Epub 2010 Jul. 19), we hypothesized that translucent AB5075 previously exposed to AB-Army1 phage would be less virulent than wild type AB5075 in a *G. mellonella* wax worm model of infection (Peleg, A. Y. et al (2009) Antimicrob Agents Chemother 53(6): 2605-2609; Loh, J et al (2013) Virulence 4(5): 419-428). Evaluation of AB5075, AB-Army1-exposed AB5075, AB5075P, AB5075 epsA::Tn5, and AB5075 ptk::Tn5 in the worm model confirmed that all four translucent strains were avirulent compared to capsule-positive AB5075 (data not shown). After day 4 post-infection, the survival rate of worms infected with AB5075 was 5%, while all other groups had survival rates of 85% or greater. Analysis of these curves using a Mantel-Cox test with Bonferroni correction for multiple comparisons determined the difference was statistically significant (P<0.0006). During the experiment, one of the PBS control worms died, likely due to injection trauma from the route of infection. A control group of untouched worms had 100% survival during the course of the experiment.

Figure 3:
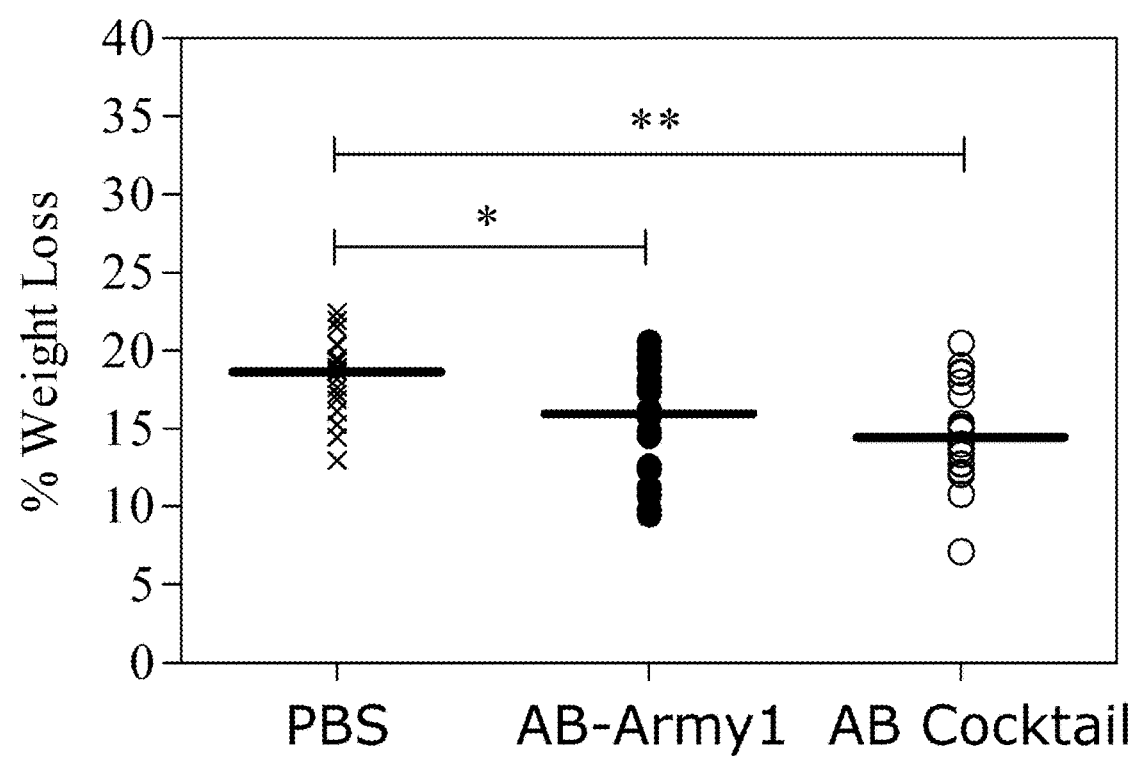
FIG. 3 depicts change in mouse weight on day two post-infection discussed in Example 2. On day 2, the median weight loss was 18.7, 16.0, and 14.5% for PBS, AB-Army1, and AB Cocktail treated mice, respectively. Statistical analysis using a Kruskal-Wallis test followed by Dunn's multiple comparison test found a significant difference between control and cocktail-treated mice (P≤0.01) and control- and monophage-treated mice (P≤0.05). Weights for day 1-5 post-infection were also collected (data not shown).

Treatment of AB5075-infected Wounds with the AB Cocktail Leads to Vastly Improved Clinical Outcomes in a Mouse Wound Model:

We wanted to determine if the bactericidal activity of the AB Cocktail observed in vitro could be recapitulated in a mouse wound model, and result in an effective treatment against AB5075-infected wounds. Briefly, neutropenic mice were subjected to a full-thickness dorsal wound via a 6 mm biopsy punch, and the wound was infected with MDR *A. baumannii* AB5075::lux, a bioluminescent isogenic strain of AB5075 (see Materials and Methods). The measured outcomes for the wound experiments included: 1) surgery/infection-associated weight loss, 2) average radiance of bioluminescent bacteria in the wound bed, 3) area of the infection as monitored by the area of bioluminescence, 4) physical wound size, and 5) biofilm formation on wound dressings. Infection-associated weight loss is an established measure of morbidity in mice (Thompson, M. G., et al. (2014). Antimicrob Agents Chemother 58(3): 1332-1342). The body weight of each animal was measured through day 5 of the infection, and the percent weight loss was calculated in comparison to day 0. The height of weight loss occurred on day 2, and the mice began to gain weight on day 3 (data not shown). On day 2, the median weight loss was 18.7%, 16.0%, and 14.5% for PBS, AB-Army1, and the AB Cocktail treated mice, respectively (FIG. 3). Statistical analysis using a Kruskal-Wallis test followed by Dunn's multiple comparison test found a significant difference between PBS- and AB Cocktail-treated mice (P≤0.01) and PBS- and AB-Army1-treated mice (P≤0.05). Thus, mice receiving either phage treatment lost less weight than the PBS-treated group during the infection and recovery.

Figure 4:
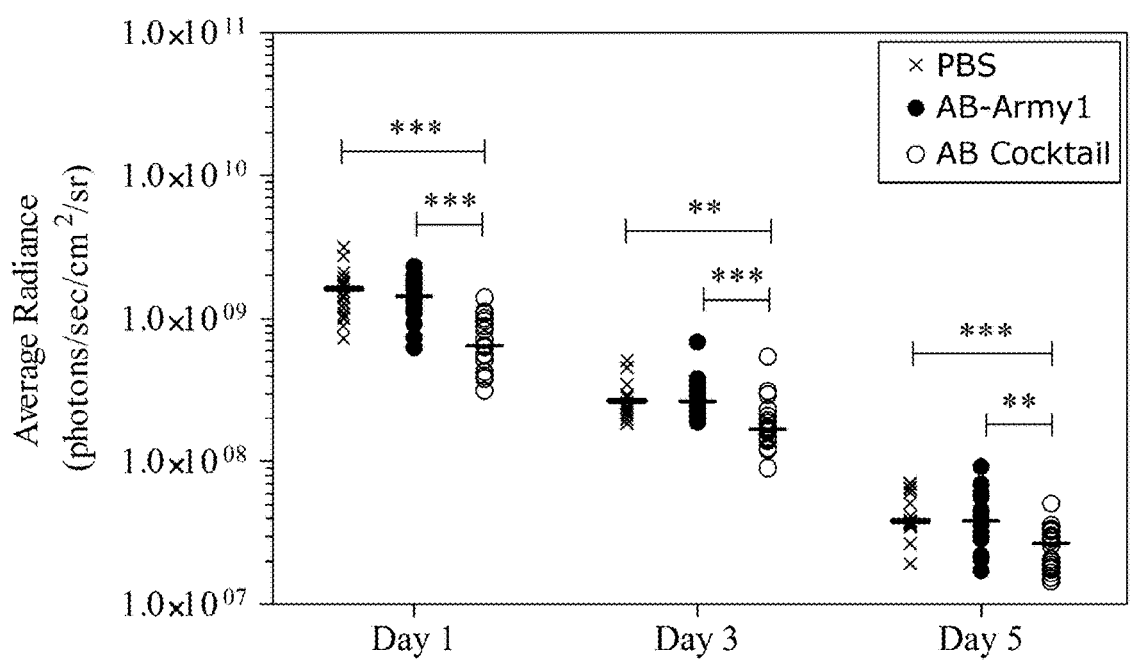
FIG. 4 depicts bioluminescence of *A. baumannii* AB5075::lux in the mouse wound discussed in Example 2. The photon emission of each wound was measured using an IVIS® In Vivo Imaging System on days 1, 3, and 5 post-infection. Statistical analysis was completed using a Kruskal-Wallis test followed by Dunn's multiple comparison test. P≤0.01; *P≤0.001.
Figure 5:
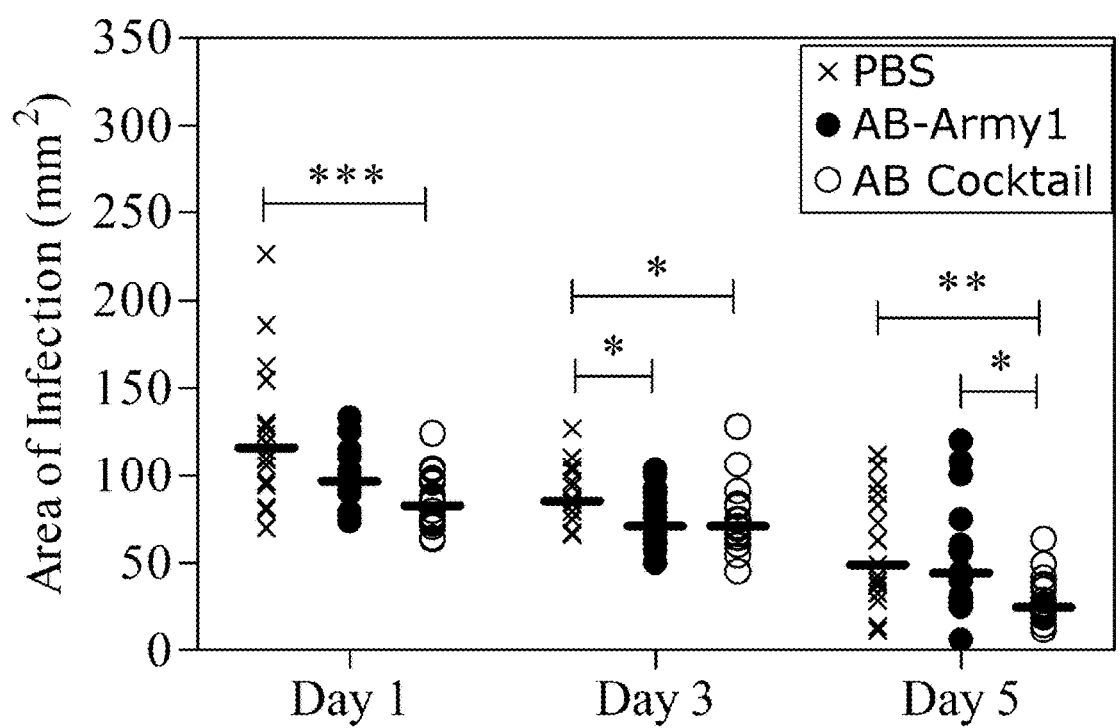
FIG. 5 depicts the infection area of *A. baumannii* AB5075::lux in the mouse wound discussed in Example 2. The area of the bioluminescence of *A. baumannii* was measured to evaluate the dispersal of AB5075::lux to areas outside of the initial boundaries of the surgical wound. Statistical analysis was completed using a Kruskal-Wallis test followed by Dunn's multiple comparison test. *P≤0.05; P≤0.01; *P≤0.001.
Figure 6A:
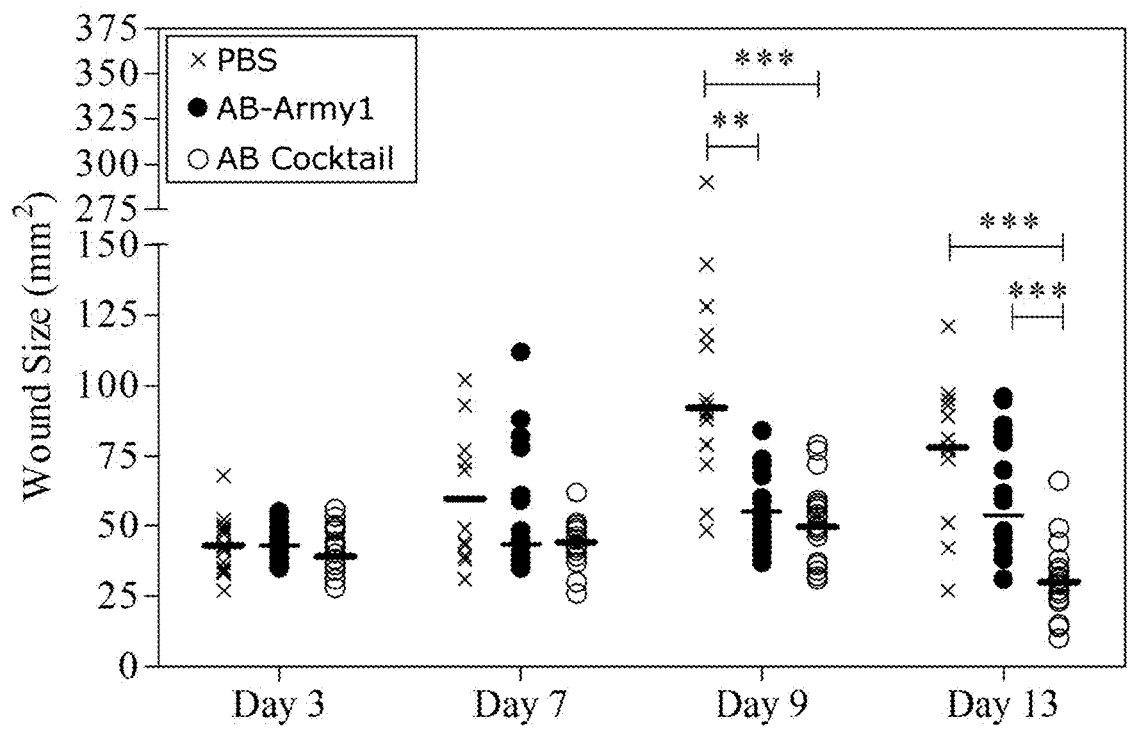
FIG. 6A and FIG. 6B depicts the size of mouse wounds over the course of infection discussed in Example 2. The size of each mouse wound was measured by Aranz on days 3, 7, 9, and 13 post-infection. (A) Comparison of treatments on days 3, 7, 9 and 13. (B) Comparison within each treatment group across days 3, 7, 9, and 13. Statistical analysis was completed using a Kruskal-Wallis test followed by Dunn's multiple comparison test. P≤0.01; *P≤0.001.

During the course of the infection, the wounds were monitored for bioburden as a function of average radiance and area of bioluminescence using an IVIS® in vivo imaging system. Bioluminescence was measured on days 1, 3, and 5 post-infection. After day 5 the bioluminescence was below background levels for all treatment groups. Heat maps of the wound bioburden suggested a difference in both signal intensity and area of infection among the groups; the most evident difference seen on day 5 when the AB Cocktail-treated wound displayed no signal (data not shown). When quantified, the AB Cocktail-treated mice had significantly less bioluminescence than the PBS- or AB-Army1-treated mice throughout the experiment, indicative of a reduced bacterial burden in the AB Cocktail-treated mice with respect to the other treatment groups (P<0.01; FIG. 4). The area of the bioluminescence was also measured, to evaluate how far the *A. baumannii* AB5075::lux disseminated into tissue surrounding the surgical wound bed. For each day measured, the area of bioluminescence in the AB Cocktail-treated wounds was significantly smaller than PBS-treated (P≤0.05, FIG. 5), suggesting that this treatment prevented the dissemination of AB5075::lux into the surrounding tissue. Thus both the bioburden and infection area, as monitored by bioluminescence, were significantly reduced in the five-member phage cocktail treated mice throughout the infection. Previous studies have shown that the proliferation of bacteria outside the initial boundaries of the surgical wound results in necrosis of the surrounding tissue, and an increase in wound size over the course of the experiment (Thompson, M. G., et al. (2014). Antimicrob Agents Chemother 58(3): 1332-1342). In agreement with these observations, the area of bioluminescence measured here was consistent with the physical wound size, as measured by Aranz (FIG. 6A). On day 9, there was a significant difference in median wound size between the PBS and AB Cocktail (P≤0.001), and PBS and AB-Army1 (P≤0.01) groups. A similar trend was also observed on day 13 between the PBS and AB Cocktail (P≤0.001), and AB-Army1 and AB Cocktail (P≤0.001) groups. Thus on days 9 and 13, the AB Cocktail-treated group had significantly smaller wounds.

Figure 6B:
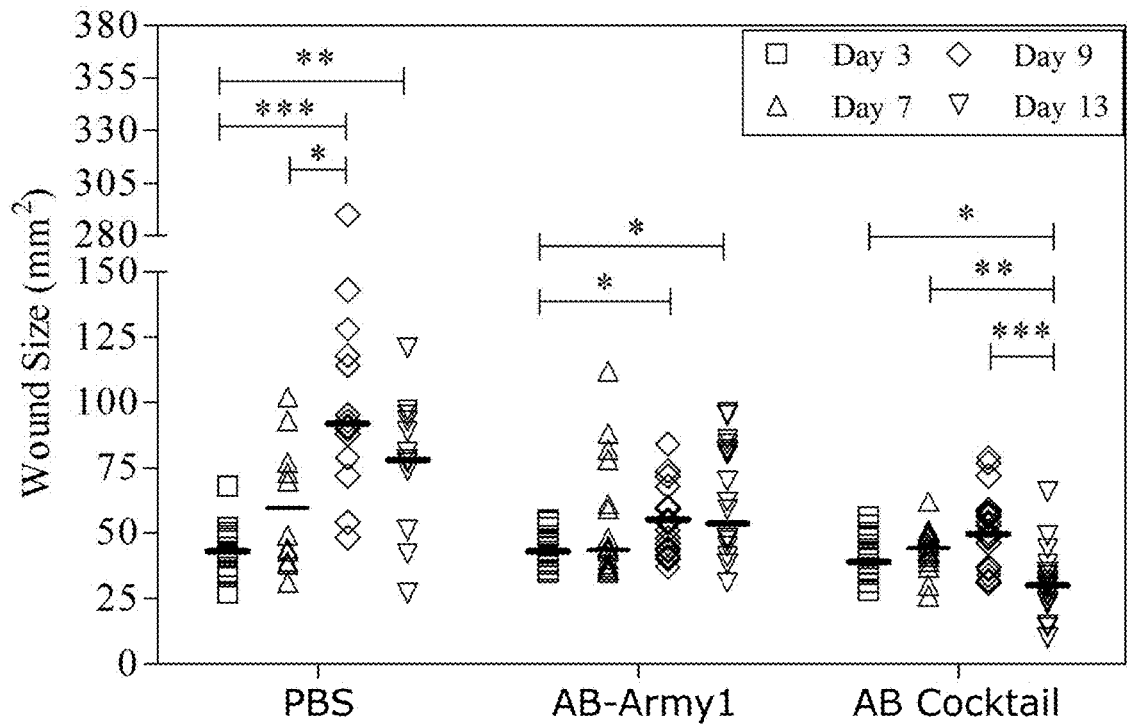

Additionally, median wound size was compared within each group across days (FIG. 6B). During the course of the experiment, maximum wound size was reached on day 9 and then the wounds began to heal and contract. In the PBS-treated mice, there was a significant increase in wound size between days 3 and 9 (P≤0.001). Less drastic but significant increases were also seen in the AB-Army1-treated mice between days 3 and 9 (P≤0.05). Conversely, there was no statistical difference in wound size for the AB Cocktail group between days 3 and 9, further suggesting that the five-member cocktail treatment prevented bacterial dissemination and tissue necrosis outside of the original surgical wound bed, and as a result the wounds never increased in size. It is important to note that there was a statistically significant difference in wound size for the AB Cocktail-treated mice on day 13, as compared to days 3, 7, and 9. However, this difference was due to a decrease in wound size on day 13 as a result of healing (FIG. 6B). Tegaderm™ dressings that were removed on day 3 post-infection from each group of mice were fixed and visualized by SEM to determine if phage treatment affected the ability of *A. baumannii* AB5075::lux to form biofilm on the bandage. A robust biofilm formed on the Tegaderm™ in the PBS- and AB-Army1-treated mice, as visualized by complex exopolysaccharide structure; however, very little mature biofilm structure is present on the Tegaderm™ from the AB Cocktail-treated mice (data not shown).

It is important to note that during the animal experiment there were three total deaths occurring on days 2 and 3 in the PBS control group. There were also two mice that had to be euthanized due to hind limb paralysis on days 4 and 5 in the PBS control group. In addition, all of the mice in the PBS control group displayed additional clinical signs of illness, including conjunctivitis, ruffled fur from reduced grooming, and decreased mobility. These kinds of negative outcomes were never observed in either of the phage treatment groups.

Discussion

This example demonstrates the successful isolation and purification of several wild environmental phages against *A. baumannii* and that these phages can be rapidly compounded into a cocktail that successfully treats *A. baumannii* wound infections in mice. The isolation and purification of these phages from local sewage water shows that phages with lytic activity against a clinically-relevant pathogen can be easily and rapidly purified from environmental sources. It should be noted that the *A. baumannii* isolates used for phage isolation were not cured of any potential prophages first, as is customary when propagating phages in a laboratory setting. Although contaminating lysogens could be present in our phage preparations, the lytic activity of the phages was not hindered, as we still saw lysis in vitro and efficacy in vivo.

Using these phages in the five-member AB Cocktail, we demonstrated effective killing of AB5075 in vitro and showed that the observed bactericidal activity occurs in a synergistic manner. AB-Army1 imposes a strong selection for the loss of receptor, likely a capsule component, and the resulting emergent unencapsulated cells were then sensitized to the AB-Navy1-4 phages. When testing the AB Cocktail against a collection of 92 MDR *A. baumannii* clinical isolates, we found that only 10 of the strains were successfully infected, highlighting the narrow spectrum of phages and the need for personalization when developing phages as a therapeutic against MDR infections.

In agreement with our in vitro findings, a similar bactericidal effect was also observed when the AB Cocktail was used as a therapeutic against AB5075::lux-infected wounds in mice. When compared to PBS-treated controls, mice treated with the five-member AB Cocktail had a reduction in weight loss, wound bioburden, area of infection, and wound size throughout the course of the study. A lack of biofilm observed on Tegaderm™ dressings of AB Cocktail mice also suggests that phage treatment prevents biofilm formation, and this specific mode of action may play a role in preventing the dissemination of bacteria into the surrounding tissue. The AB Cocktail-treated group also had no fatalities or paralysis events. By every metric followed here, the personalized phage cocktail we developed serves as an effective treatment against MDR *A. baumannii* AB5075 wound infections in this model (Thompson, M. G., et al. (2014). Antimicrob Agents Chemother 58(3): 1332-1342). While the individual AB-Army1 phage did show some efficacy, it was not as effective as the full AB Cocktail, consistent with the combinatorial effect seen in vitro. It should be noted that we administered a high dose of phage both topically and systemically here, 4 hours post infection. While it is known that at 4 hours post-infection *A. baumannii* AB5075 has increased by at least a log in the mouse wound model (Thompson, M. G., et al. (2014). Antimicrob Agents Chemother 58(3): 1332-1342), work is on-going to determine if these phages can be effective against a more established infection and if a single route of administration at a lower dose would produce similar outcomes.

Phages are narrow spectrum even to the subspecies level, which is of value when trying to avoid damage to the host microbiome, but poses a significant challenge when developing a therapeutic to be used widely to treat infection. Thus, it is likely that phages will be most viable as a personalized therapeutic, where a specific bacterial isolate from a patient is used to produce a customized cocktail that is rapidly compounded to treat that specific patient and infection. Here we demonstrate that wild, environmental phages can be easily purified and rapidly compounded against the MDR clinical isolate AB5075 using a high throughput liquid assay. Personalized phage cocktail formulation in a clinically relevant time-frame from a known library may require new diagnostic techniques to assist screening phage libraries. Here, Raman spectroscopy could distinguish between strains susceptible to AB-Army1 and those that are resistant. Because of the speed of Raman spectroscopy and no requirement for culturing, we are pursuing the use of Raman spectroscopy to assist in rapid cocktail formulation.

In this work we isolated lytic phages specific to *A. baumannii* from limited environmental sources and compounded a proof-of-concept five-member phage cocktail against the model MDR pathogen *A. baumannii* AB5075 (Jacobs, A. C. et al (2014) MBio May 27; 5(3):e01076-14). Further, we successfully demonstrated the efficacy of this cocktail in a murine full thickness wound infection model. These results highlight the potential for developing targeted phage therapeutics to combat the growing threat of MDR bacterial pathogens.

Data also show that the phage cocktail prevents biofilm formation, lowers the bioburden in the wound, prevents the spread of infection and necrosis to surrounding tissue, and decreases infection-associated morbidity. This effective cocktail is composed of four phages that do not kill the parent strain of the infection, and one phage that simply delays bacterial growth in vitro via a strong but incomplete selection event. Interestingly, the cocktail here appears to function in a combinatorial manner, as one constituent phage targets encapsulated *A. baumannii* and selects for loss of receptor, shifting the population to an unencapsulated state that is then sensitized to the remaining four phages in the cocktail. Additionally, capsule is a known virulence factor for *A. baumannii*, and data demonstrate that the emergent unencapsulated bacteria are avirulent in a *G. mellonella* model. While it is not necessary to understand the mechanism of action by which phage inhibit bacterial growth, these results highlight the importance of anticipating population changes during phage therapy and designing phage cocktails to control emergent strains, as well as the benefits of using phages that target virulence factors. Because of the efficacy of this cocktail isolated from a limited environmental pool, a pipeline for developing new phage therapeutics against additional clinically relevant multidrug resistant pathogens using environmental phages sourced from around the globe is being established.

This example demonstrates that synergistic cocktails can provide therapeutic efficacy. Notably, in this example, a tiered library against AB5075 was not iteratively screened, as the method of the instant invention directs, because such a library did not exist at the time against *A. baumannii*. Thus, uncharacterized natural phages from the wild were screened to identify phages that, when cocktailed, showed therapeutic potential. Though useful for a proof of concept animal study, uncharacterized natural phages from the wild would be inappropriate for human use. Additionally, though not specified above, screening wild phages to find those appropriate for use in the *A. baumannii* therapeutic cocktail described above required almost 9 months of work.

In addition, the specific method in the example above required passaging the infectious targeted bacterial strain (AB5075) through a mouse wound, in order to facilitate the discovery of phages that have therapeutic activity when compounded into a cocktail, but have no detectable activity against the targeted pathogen on their own, e.g. phages AB-Navy1 through AB-Navy4. Such a step is not possible or ethical in humans.

It is contemplated herein that having a diverse characterized tiered library to iteratively screen according to the methods of the instant invention would have facilitated much more rapid cocktail discovery, and would facilitate the discovery of synergistic cocktails with counterintuitive composition. The specific methods used in the example above are also limited as they are incapable of rapidly and reliably producing synergistic phage cocktails as contemplated according to the methods of the instant invention.

Example 3

Compounding of Phage Cocktail Directed To Methicillin-resistant *Staphylococcus aureus* (MRSA)

It is contemplated herein that the methods of the instant invention are not restricted to a single bacterial species, but can be used against multiple different bacterial pathogens. Accordingly, in addition to studies with *A. baumannii* described in Example 2, studies with *Staphylococcus aureus* have been performed. It is contemplated herein that data provided below indicate that synergistic cocktails can be compounded against different strains of bacteria, thus demonstrating the broad applicability of the disclosed methods. Also, notably, *Staphylococcus* is a gram positive microorganism. Thus, the methods can be used against multiple pathogens, regardless of bacterial surface type.

Skin and soft tissue infections (SSTI) caused by methicillin resistant *Staphylococcus aureus* (MRSA) are difficult to treat. In this study, seven novel phages with broad lytic activity for *Staphylococcus aureus* (*S. aureus*) were isolated and identified. Screening of a diverse collection of 170 clinical isolates by efficiency of plating (EOP) assays shows that these novel phages are virulent and effectively prevent growth of 95% of MRSA and methicillin sensitive *S. aureus* (MSSA) isolates. Phage K, which was previously identified as having lytic activity on *S. aureus*, was tested on the *S. aureus* collection and shown to prevent growth of 82% of the isolates. These same novel phage were examined by electron microscopy, the results of which indicate that the phage belong to the Myoviridae family of viruses. The novel phage group utilizes β-N-acetyl glucosamine (GlcNac) moieties on cell wall teichoic acids as cell surface receptors. The phages were distinct from, but closely related to, phage K as characterized by restriction endonuclease analysis and protein profiling. Furthermore, growth rate analysis indicates that a combination of phage K, with phage SA0420φ1, SA0456φ1 or SA0482 φ1 have a synergistic phage-mediated lytic effect on MRSA and suppress formation of phage resistance for 48 hours. These results indicate that a broad spectrum lytic phage mixture can suppress the emergence of resistant bacterial populations and hence have great potential for combating *S. aureus* infections.

Materials and Methods:

Bacterial Strains and Growth Methods:

The *S. aureus* clinical isolate collection was available at Naval Medical Research Center (NMRC) (Silver Spring, Md.). Strains with the prefix NSC or NSI were collected at the Naval Medical Research Unit-6 (NAMRU-6) in Lima and Iquitos, Peru, respectively. Community acquired *S. aureus* isolates were collected from the community hospital at Fort Benning, Ga. MRSA strains were isolated from hospital staff, outpatients, and inpatients over a five-year period. Strains were grown at 37° C. in Tryptic soy broth (TSB). Solid media contained 1.5% (wt/vol) bacteriological agar (BD).

Bacteriophage Isolation:

Phage K samples were purchased from the American Type Culture Collection (Manassas, Va.) (ATCC19685-B1) and propagated in *Staphylococcus hyicus*. The novel phages were isolated from untreated sewage obtained from the municipal water treatment plant at Frederick, Md. Three 500 ml batches of influent sewage water were collected and fortified with 15 grams of Trypticase soy (TS) and 1 mL of MRSA strains (NSC0414, NSC0420, NSC0456, NSC0470, NSC0482, NSC0409 and NSC0419) and incubated for 24 hours at 37° C. Following incubation, 1 ml was centrifuged for 5 minutes at 8000 g and the supernatant sterilized by 1 minute of centrifugation at 8000 g with a 0.22 μm microfuge filter (Costar® Cat#8160). A total of 10 μl of filtrate were screened for lytic phage via plaque assays using the soft agar overlay technique. (Hershey A D et al., The Journal of General Physiology 1953; 36:777-89.) Plates were incubated at 37° C. for 24 hours before scoring for the presence of plaques. Plaques were purified three times by removing plugs and overnight elution in SM buffer (50 mM Tris pH 7.5, 100 mM NaCl, 8 mM $MgSO_4$ and 0.01% gelatin) followed by amplification in the host strain. Phage titer was assessed by plating ten-fold serial dilutions and calculating the plaque forming units (PFU).

Host Range Analysis and Phage Comparison:

The host range of the novel phage group and phage K was examined via an efficiency of plating assay (EOP) (Kutter E. Methods Mol Biol 2009; 501:141-9) for *S. aureus* clinical isolates. Specifically, 3.5 μl of a 10-fold dilution series of phages SA0414φ1, SA0414φ2, SA0420φ1, SA0456φ1, SA0470φ1, SA0482φ1, SA11987φ1 and phage K (starting at $1 \times 10^8$ PFU/ml) were spotted on TSA seeded with 800 μl of bacterial clinical isolates at 0.6 $OD_{600}$. A total of $1 \times 10^5$ phage particles were loaded in the first row. Plates were incubated overnight at 37° C. and scored for the ability to inhibit bacterial growth. Plaque formation at any dilution is considered an indication of phage virulence. Phage species specificity was tested by spotting 10 μl of $1 \times 10^8$ PFU/ml on bacterial lawns of *S. cohnii, S. epidermitis, S. haemoliticus, S. saprophiticus, S. sciurii, S. xylosus* and *S. hyicus*. A clear area was considered indicative of virulence.

Phage Purification:

The corresponding *S. aureus* host strain was grown to 0.1 $OD_{600}$ at 37° C. Cells were infected with phage stock at a multiplicity of infection (MOI) of 0.5 and incubated at 37° C. until the culture was clear. The lysate was cleared via centrifugation at 10,000 g for 10 minutes and 360 grams (10% w/v) of polyethylene glycol 8000 (PEG) was added to the supernatant and precipitated overnight at 4° C. The solution was centrifuged at 5,000 g for 1 hour, the supernatant decanted, and the pellet resuspended in 5 ml of SM buffer. Next, 0.75 grams of cesium chloride per ml of precipitate was added and mixed by inversion. The sample was centrifuged on a 90 Ti rotor at 58,000 g at 4° C. for 24 hours. The resulting band was retrieved and dialyzed by using a 10,000 Da MWC Slide-A-Lyzer® dialysis cassette (Pierce, Appleton, Wis.), in 4 L of dialysis buffer (100 mM NaCl, 8 mM $MgSO_4$, 50 mM Tris-Cl). After 24 hours the dialysis buffer was exchanged and dialyzed for 4 hours. Phage was collected from the dialysis cassette and titered.

Phage DNA Purification:

Purified phage (150 μl) was mixed with 6 μl of 0.5M EDTA pH 8, 10 μl of Proteinase K (20 mg/ml) and 7.5 μl of 10% SDS and incubated for 1 hour at 56° C. Once cooled to room temperature, three extractions with 150 μl of Tris-EDTA saturated phenol and three extractions with 150 μl of 24:1 Chloroform: Isoamyl alcohol. The supernatant was mixed with 10 μl of 3M sodium acetate and 1 ml of 100% ice cold ethanol overnight at −20° C. The DNA sample was centrifuged at 10,000 g for 5 minutes and the pellet washed three times with 750 μl of 70% isopropanol. The pellet was air dried for 5 minutes and resuspended in 50 μl of distilled water. The DNA concentration was determined by reading $OD_{260}$ on a spectrophotometer.

Pulse-field Gel Electrophoresis (PFGE):

Purified phage DNA (20 μg) was digested with EcoR1 restriction endonuclease for 3 hours at 37° C. The digested samples were loaded into a 1% pulse field agarose gel prepared with 0.5×TBE and resolved on for 11 hours at 14° C. with a pulse rate of 30 volts/s and a switch time of 1-6 seconds under constant buffer recirculation. Upon completion, the gel was incubated for 10 minutes in 0.5×TBE containing 0.1 μg/ml ethidium bromide followed by three, 10 minute washes with 0.5×TBE and imaged on a BioRad® gel documentation system.

Electron Microscopy:

Standard methods of sample preparation were employed for transmission electron microscopy (TEM) and scanning electron microscopy (SEM). Briefly, cesium chloride purified bacteriophages ($1 \times 10^5$-$5 \times 10^7$ total phage) were fixed in 4% paraformaldehyde with 1% glutaraldehyde in 0.1 M sodium cacodylate buffer for 2 hours. After fixation, a portion of each sample was spread onto carbon coated copper grids, washed with water to remove fixative, and negatively stained with 1% uranyl acetate. The grids were imaged with an FEI Tecnai T12 TEM at 100 kV. The remaining sample was processed for SEM analysis. The fixed samples were washed three times with 0.1 M sodium cacodylate buffer, post fixed for 1 hour with 1% osmium tetroxide buffer, washed, and then immersed in a 0.5% uranyl acetate solution for 1 hour. The samples were subsequently dehydrated through an ethanol series, critically point dried, and coated with gold-palladium. The coated SEM samples were imaged in an FEI Quanta 200 FEG SEM at 5 kV.

Preparation of Microtiter Plates for Growth Rate Assay:

Microtiter plates (96 well) were prepared as follows. 90 μl of TS broth with 1% v/v tetrazolium dye was added to each well. 10 μl of $1 \times 10^8$ PFU/ml of each phage were diluted 10-fold down to 10 PFU per well. 10 μl of 0.4 $OD_{600}$ of bacteria ($4 \times 10^6$ cells) were added to each experimental well for a final volume of 100 μl corresponding to a multiplicity of infection (MOI) range of 2.5 to $2.5 \times 10^{-5}$. Media and phage only controls were added. The 96 well plates were incubated using the phage efficacy assay methods of Example 1 at 37° C. for 48 hours. Phage mixtures were prepared at equal volumes of phage for a final titer of 1×10⁸ PFU/ml.

The isogenic strains with null mutations for ΔtarO, ΔtarM, ΔtarS and the ΔtarMΔtarS double mutant were provided by Dr. Suzanne Walker (Harvard Medical School, Boston, Mass.).

Results:

Isolation of Novel S. aureus Phage:

In an effort to isolate broad spectrum lytic phage against MRSA strains, seven MRSA clinical bacterial isolates were used as hosts to isolate phage from environmental sources, primarily raw sewage which is a rich source of environmental phage. (Synnott A J et al. Applied and Environmental Microbiology 2009; 75:4483-90.) Seven plaque-forming phages were identified in their corresponding S. aureus host strains: SA0414Φ1, SA0414Φ2, SA0420Φ1, SA0456Φ1, SA0470Φ1, SA0482Φ1, and SA11987Φ1 henceforth referred to collectively herein as "novel phage". Phage SA0414Φ1 and SA0410Φ2 represent two isolates with distinct plaque morphologies within the same phage isolation that were studied independently (data not shown). (Xia G, et al. The Journal of Biological Chemistry 2010; 285:13405-15.)

Figure 7:
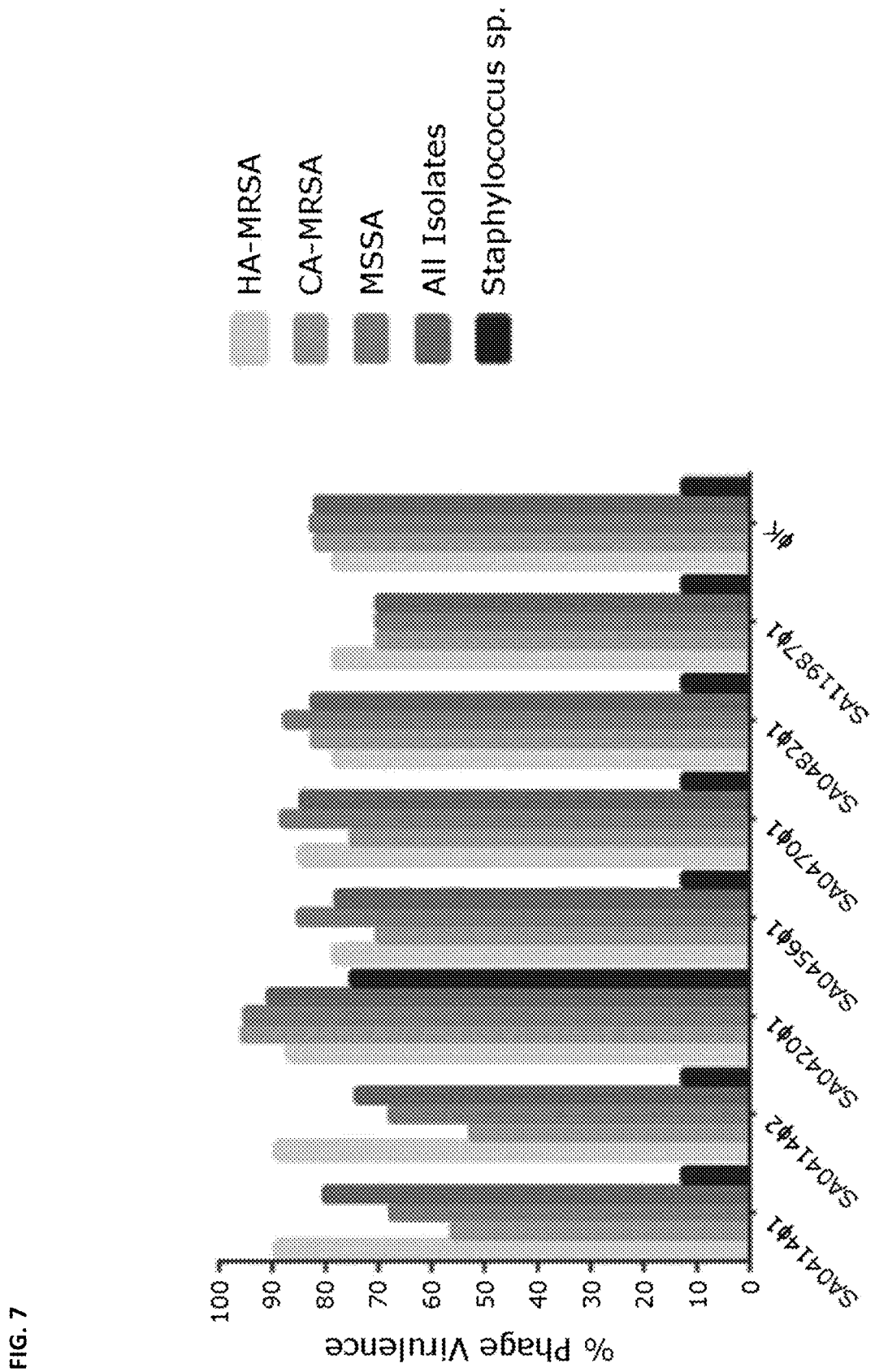
FIG. 7 depicts the virulence spectra of the indicated *S. aureus* phage as a percentage of strains infected as discussed in Example 3. The *Staphylococcus* species used in this study include *S. cohnii, S. epidermidis, S. hyicus, S. haemoliticus, S. saprophyticus, S. sciuri*, and *S. xylosus*. "HA-MRSA" refers to Healthcare-Associated MRSA isolates; "CA-MRSA" refers to Community-Acquired MRSA isolates; "MSSA" refers to methicillin sensitive *S. aureus* isolates.

The S. aureus Phages are Polyvalent in Nature:

To determine the spectrum of the novel phage, a set of 170 S. aureus clinical isolates was obtained from different geographical regions to enrich strain diversity. This bacterial diversity set includes MSSA (methicillin sensitive S. aureus) and MRSA (methicillin resistant S. aureus) from both community and health care settings. The S. aureus isolates were screened for lytic activity by efficiency of plating (EOP) assays. The EOP assay determines the relative virulence of each phage against a S. aureus strain, thereby allowing side-by-side comparisons of phage virulence (Kutter E. Phage host range and efficiency of plating. Methods Mol Biol 2009; 501:141-9.) In addition, spotting phages on strain-specific S. aureus lawns creates individualized phage profiles. Results indicate that the novel phage were virulent against 70%-91% of the strains tested (data not shown; FIG. 7). Data also indicate that, individually, phage SA0414Φ1 and SA0414Φ2 were virulent against 80% and 74% of the isolates, respectively. This establishes a distinction between these independent isolates of strain NSC0414. Phage SA0470Φ1 affected 85%, phage SA0420Φ1 affected 91%, phage SA0456Φ1, SA0482Φ1 and SA11987Φ1 each affected 78%, 84% and 82% of isolates (data not shown; FIG. 7). For Healthcare-Associated MRSA (HA-MRSA) isolates, virulence ranged from 78%-89% whereas for Community-Acquired MRSA (CA-MRSA) strains, virulence range is 43%-93% of the isolates (data not shown; FIG. 7). In the case of MSSA strains, the phages were proven virulent against 85%-93% of the strains tested. To assess species specificity, the S. aureus phage were tested against S. cohnii, S. epidermitis, S. haemoliticus, S. saprophiticus, S. sciurii, S. xylosus and S. hyicus. The results demonstrate that phage SA0414Φ1 and SA0414Φ2, SA0456Φ1, SA0470Φ1, SA0482Φ1, and SA11987Φ1 can only form plaques on S. aureus and S. hyicus. In contrast, SA0420Φ1 was capable of infecting all Staphylococcus species tested with the exception of S. xylosus (FIG. 7). In addition, the phage did not infect gram negative bacterial species Escherichia coli, Enterococcus faecium, Acinetobacter baumannii, Klebsiella pneumoniae and Pseudomonas aeruginosa (data not shown). The results of these experiments indicate that the novel phages are polyvalent phage and specific to S. aureus and S. hyicus.

Previous studies demonstrated that phage K is a polyvalent S. aureus phage. The virulence of phage K was tested in this collection of clinical isolates and results show phage K is virulent against 82% of the isolates. For HA-MRSA strains, virulence was 78% compared to 87.5% of the CA-MRSA and 82.5% MSSA strains (data not shown; FIG. 7). It is noteworthy that phage K was not virulent on strains NSC0637 and NSC0096; however the novel phage infected these strains (data not shown; FIG. 7). This establishes a phenotypic distinction between the novel phage and phage K. In addition, phage K is virulent on a geographically independent set of strains underscoring the polyvalent nature of phage K.

Electron Microscopy Analysis of S. aureus Phages:

S. aureus phages are members of the Myoviridae, Syphoviridae and Podoviridae family of viruses. (Deghorain M, Van Melderen L. Viruses 2012; 4:3316-35.) Due to the similarities in virulence spectrum of the novel phage and phage K, structural similarities amongst the phage are possible. To assess the morphology of the S. aureus phage, electron microscopy studies were performed on the novel phage group and contrasted to phage K. Consistent with the structural features of phage K, the novel phage have a polyhedral shaped capsids and long contractile tails (data not shown). Furthermore, the phage genomic DNA size is greater than 140 Kb (data not shown). These results classify the novel phage as members of the Myoviridae family. In addition, we identified the novel phage in both the relaxed and contracted conformations (data not shown). The binding of the phage to S. aureus strain ATCC11987 was monitored by electron microscopy. The results indicate that all phage effectively recognize and bind at multiple sites on the S. aureus cell surface (data not shown.)

The S. aureus Novel Phage Group and Phage K are Distinct from Each Other:

Due to consistency in morphologies and lytic spectra between phage K and the novel phage, it was considered possible that these could be independent environmental isolates of phage K (data not shown). To assess this, EcoR1 DNA restriction profiles of the novel phage were compared with phage K via pulse field gel electrophoresis (PFGE) as described above. The results show that phage K generates a pattern distinct from phage SA0420φ1, SA0456φ1, SA0470φ1, SA0482φ1, and SA11987φ1 (data not shown). Additionally, comparison of the novel phage digestion patterns shows no difference in EcoRI digestion patterns, suggesting they are closely related (data not shown). Collectively, these results strongly suggest that the S. aureus phage are novel in nature and are not environmental isolates of phage K.

Figure 8:
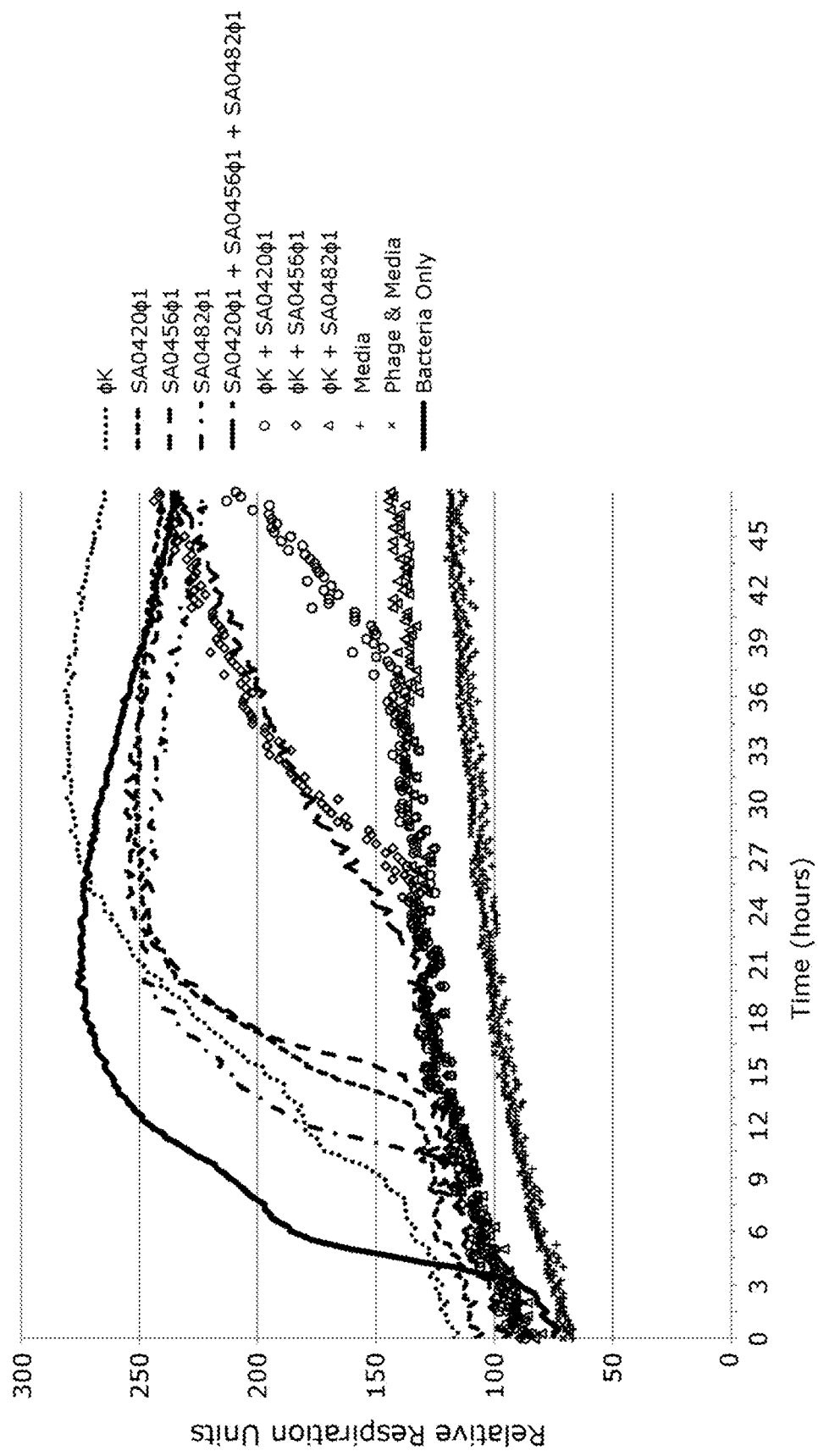
FIG. 8 depicts analysis of bacteriophage cocktails on *S. aureus* as discussed in Example 3. MRSA strain NSI0016 was monitored for 48 hours in a growth assay described in Example 1. A total of $4 \times 10^6$ cells were added per well. Phage was added to a final Multiplicity of infection (MOI) of 2.5 and growth was measured every 15 minutes for 48 hours. The plots represent triplicate experiments; all combinations contain identical total phage quantities.

In Vitro Inhibition of S. aureus Growth by the Novel Phage Group and Phage K Mixtures are Synergistic:

Studies indicate S. aureus can develop resistance to the lytic effects of phage infection. (Rosato R R, Cameron J A. Biochimica et Biophysica Acta 1964; 83:113-9.) To determine if resistance to the novel phage group and phage K is observed amongst the clinical isolates, a growth curve analysis was performed utilizing the automated phage efficacy assay system described in Example 1 provided herein. This system monitors and characterizes phage infection at continuous intervals, providing insight into phage resistance and effectiveness. For this study, strain NSI0016 was used as host. Phage K incubation with strain NSI0016 resulted in bacterial growth inhibition for 8 hours, indicating that resistance to Phage K arises in this strain (FIG. 8). Phage SA0420Φ1, SA0456Φ1 and SA0482Φ1 inhibit bacterial growth for 10, 12, and 15 hours, respectively. However, phage resistance is also evident after these incubation periods. Media-only or phage-only controls show baseline oxidation levels of reporter dye (FIG. 8). These results suggest that all phage are virulent against strain NSI0016, but insufficient to control growth for time spans larger than 8-15 hours.

Figure 9:
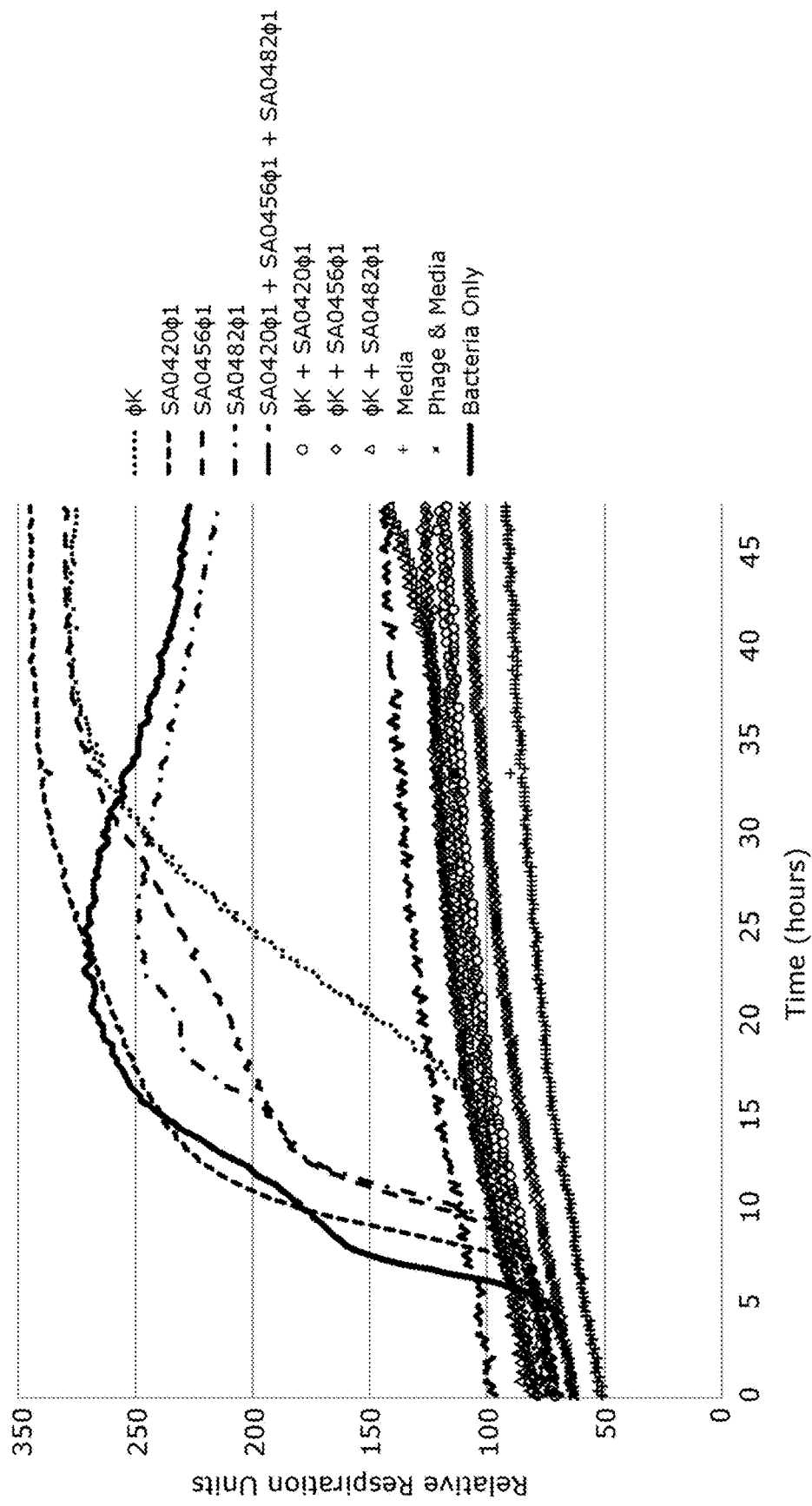
FIG. 9 depicts analysis of bacteriophage cocktails on *S. aureus* strains as discussed in Example 3. MRSA strain 3195.CO1 was monitored for 48 hours in a growth assay described in Example 1. A total of $4 \times 10^6$ cells were added per well. Phage was added to a final Multiplicity of infection (MOI) of 2.5 and growth measured every 15 minutes for 48 hours. The plots represent triplicate experiments; all combinations contain identical total phage quantities.

To see if emergence of phage-resistance could be reduced by using phage combinations, phage SA0420φ1, SA0456φ1 or SA0482φ1, with phage K were tested (FIG. 9). The combination of phage K with phage SA0420φ1 inhibited growth for 20 hours while SA0456φ1 growth was inhibited for 26 hours. In the case of phage SA0482φ1, the combination with phage K inhibited growth of NSI0016 for 36 hours. The effects of these phage combinations are more pronounced on strain 3195.CO1, where phage SA0420φ1, SA0456φ1 and SA0482φ1 in combination with phage K completely inhibit bacterial growth (FIG. 9). The results demonstrate that this phage combination can synergize to inhibit growth of NSI0016 and 3195.CO1 (FIG. 8 and FIG. 9). These results show that combining phage K with SA0420φ1, SA0456φ1, SA0482φ1 or a combination of the novel phage has a synergistic growth inhibition effect, suggesting the combination may reduce formation of phage resistance.

The S. aureus Phages Require Cell Wall Teichoic Acid Molecules for Infection:

Studies have suggested that phage K utilizes teichoic acid molecules as cell surface receptors for infection. (Xia G, et al. Journal of Bacteriology 2011; 193:4006-9.) The tarO gene encodes the N-acetyl glucosamine transferase, the enzyme responsible for initiating wall teichoic acid (WTA) synthesis in S. aureus. The catalytic activity of the tarO gene product can be inhibited by treatment with tunicamycin. (Brown S, et al. Annu Rev Microbiol 2013; 67:313-36; Pasquina L W, et al. Current Opinion in Microbiology 2013; 16:531-7.) To elucidate the cell surface receptor utilized by the novel phage group, tunicamycin was used as an inhibitor of the N-Acetyl glucosamine transferase activity. Addition of 0.1 mg/ml of tunicamycin caused a 1000-fold inhibition in the ability of the novel phage group to infect bacteria (data not shown). In comparison, phage K Infection was inhibited 100-fold by tunicamycin treatment (data not shown). To assess the contribution of WTAs to phage infection of strains from our S. aureus collection, a sub-set of strains were screened for tunicamycin-mediated inhibition of phage infection. Exposure of strain 1028.N to tunicamycin caused a 100,000 fold inhibition of S. aureus infection by the novel phage group. This strongly suggests that teichoic acid molecules are involved in infection of the S. aureus clinical isolates in this study (data not shown).

To further assess the WTA pathway involvement in the novel phage group infection of S. aureus, a series of null mutants were used. The strain RN4220 was selected as host due to the absence of a capsule, prophage, and restriction digestion modification systems known to produce immunity against phage infection. (Brown S, et al. Proceedings of the National Academy of Sciences of the United States of America 2012; 109:18909-14.) EOP assay show that the novel phage group infect strain RN4220, albeit at a lower efficiency than phage K. Infection by phage SA0414φ1 and SA0414φ2 was only evident at the highest phage titer (data not shown).These results indicate that this strain background is suitable for assessing the contribution of WTA biosynthetic enzymes to infection by the novel phage group.

To assess further the involvement of the WTA pathway, isogenic null mutants of tarO, tarM, tarS and the ΔtarM ΔtarS double mutant were utilized. (Brown S, et al. Annu Rev Microbiol 2013; 67:313-36; Brown S, et al. Proceedings of the National Academy of Sciences of the United States of America 2012; 109:18909-14; Xia G, et al. The Journal of Biological Chemistry 2010; 285:13405-15.) The ΔtarO strain is impervious to infection by the novel phage group, however, the effects on phage K lysis inhibition are minimal on this assay (data not shown). EOP on ΔtarS mutant show complete inhibition of the lytic activity of the novel phage group, implicating β-GlcNAc moieties of the WTAs in phage infection. In contrast, the deletion of ΔtarM enhances the lytic activity of the phage. The ΔtarM ΔtarS double mutant shows a lytic phenotype that resembles the ΔtarS single mutant (data not shown). These results indicate that β-GlcNAc moieties on WTA are essential for the novel phage infection of S. aureus.

Discussion

Reducing antimicrobial agent resistance is crucial for development of therapies against multiple-drug resistance in organisms such as S. aureus. (WHO, Antimicrobial resistance: global report on surveillance World Health Organization, 2014.) The results outlined in this example describe 7 novel polyvalent S. aureus phage virulent against 70% to 91% of the clinical isolates in our collection (data not shown; FIG. 7). Phage K has been reported as a broad spectrum phage against MRSA strains. (O'Flaherty S, et al. Applied and Environmental Microbiology 2005; 71:1836-42.) Here, we have expanded on those studies by finding phage K virulent against 82% of the of S. aureus strains (data not shown, FIG. 7). Importantly, the novel phage complements the virulence of phage K. For example, in strains NSC0096 and NSC0637, phage K is ineffective, yet members of the novel phage group are virulent against these same strains (data not shown). This makes phage K and all members of the novel phage group suitable candidates for a phage mixture for therapeutic treatment of S. aureus infections. Either phage K or the novel phage group fail to infect gram negative bacteria and are specific to S. aureus, showing minimal staphylococcal species cross virulence by infecting S. hyicus (FIG. 7). One exception was phage SA0420φ1 which infected several Staphylococcus species including S. cohnii, S. epidermitis, S. haemoliticus, S. saprophiticus, and S. sciurii. This suggests that phage SA0420φ1 targets cell surface receptors common to all Staphylococcus species tested.

Electron micrograph studies demonstrate the novel phage group are members of the Myoviridae family, characterized by a polyhedral capsid, a long contractile tail and genomes larger than 140 Kb (data not shown) (Deghorain M, Van Melderen L. Viruses 2012; 4:3316-35.) Indeed, our study determined that genome sizes of all the members of the novel phage group are 140 Kb or larger, consistent with members of the Myoviridae family (data not shown). The polyvalent nature of the novel phage showed a similarity with phage K, however, restriction analysis demonstrates otherwise (data not shown). Further distinction comes from lytic spectrum EOP analysis, where comparison of equal titers generates virulence profiles distinct for each strain-phage combination reflecting genetic differences among the novel phage (data not shown, FIG. 7). In the case of phage SA0414φ1, it has an average non-contracted tail size of 90.6 nm and an average contracted tail size of 53.8 nm and an average capsid size 98.5 nm. In contrast, SA0414φ2 has an average non-contracted tail size of 206.5 nm, an average contracted tail size of 112.5 nm and an average capsid size of 105.5 nm. Even though their lytic spectra are very similar, the difference in size establishes a morphological distinction between these phages (data not shown, FIG. 7). Taken together, the results indicate that the novel phages are polyvalent in nature and effective against *S. aureus* clinical isolates.

This study shows that phage K resistance develops in strain NSI0016 after 8 h. Phage resistance is prevented or delayed by the addition of phage SA0420φ1, SA0456φ1 or SA0482φ1. Different degrees of enhanced virulence are observed when combining phage K with SA0420φ1, SA0456φ1 or SA0482φ1 (FIG. 8 and FIG. 9). Additionally, the combination of phage SA0420φ1, SA0456φ1 and SA0482φ1 effectively reduced phage-resistance on NSI0016 and 3195.CO1 (FIG. 8 and FIG. 9). The synergistic effects observed in phage K combinations suggest that the novel phage group utilized an infection mechanism distinct from phage K. However, the additive effects observed in the SA0420φ1, SA0456φ1 and SA0482φ1 triple combination indicate that there are differences in the mechanisms of infection among them. Perhaps, differences in novel phage affinity toward cell surface receptors may alter phage replication kinetic in a particular host resulting in distinct latent periods and bust sizes.

Previous studies have implicated cell wall teichoic acids as important components for absorption of phage in the Myoviridae virus family. (Xia G, et al. J Bacteriol 2011; 193:4006-9; PMID: 21642458). Treatment with tunicamycin, an inhibitor of N-acetyl glucosaminidase activity, led to the inhibition of infection by the novel phage group suggesting a role of this modification in the infection mechanism (data not shown). Importantly, the effect of tunicamycin is not confined the RN4220 strain for treatment of clinical isolate strain 1028.N1 shows a 10,000 fold reduction in phage infection (data not shown). In other clinical isolates, a 10-fold reduction is observed (data not shown). The deletion of the N-acetyl glucosamine transferase, ΔtarO, impedes infection by members of the novel phage group, implicating cell wall teichoic acids as a key component for infection (data not shown). Furthermore, the deletion of ΔtarS, the β-N-acetyl glucosaminidase, rendered the cells insensitive to infection by the novel phage group. This suggests that β-N-acetyl glucosamine modification of cell wall teichoic acids act as cell surface receptors for the novel phage group (data not shown).

Interestingly, the deletion of tarM, the α-Nacetyl glucosaminidase, enhances the ability of the novel phage group to infect strain RN4220 (data not shown). This may be due to increased β-N-acetyl glucosamine modification of WTAs enhancing binding of the novel phage group. Alternatively, the α-N-acetyl glucosaminidation may have an inhibitory effect on phage infection. Of note is the fact that the extent of WTA modification in *S. aureus* varies among strains. Some *S. aureus* strains have been reported to exclusively harbor α or β-GlcNAc modifications in WTAs while other strains consist of a mixture of both modifications. (Brown S, et al. Annu Rev Microbiol 2013; 67:313-36; Jenni R, Berger-Bachi B. Arch Microbiol 1998; 170:171-8; Winstel V et al. mBio 2014; 5:e00869.) This level of heterogeneity could explain the difference in phage susceptibility among *S. aureus* isolates. Saliently, phage K infection was not affected by ΔtarS or ΔtarM and only mildly by ΔtarO, suggesting that phage K may use other receptors besides WTAs. The enhancement of growth inhibition observed in phage K combinations with SA0420φ1, SA0456φ1 and SA0482φ1 support the notion that the novel phage group use a common cell surface receptor distinct from that of phage K.

It is noteworthy that β-N-acetyl glucosamine modifications of WTAs have been linked to potentiation of β-lactam antibiotic resistance on MRSA strains. (Brown S, et al. Annu Rev Microbiol 2013; 67:313-36; Brown S, et al. Proceedings of the National Academy of Sciences of the United States of America 2012; 109:18909-14.) β-N-acetyl glucosamine modifications serve as binding sites for the PBP2a, the enzyme responsible for β-lactam resistance in *S. aureus*, allowing for continuous cell wall synthesis. Interestingly, the WTA β-N-acetyl glucosamine modification needed for β-lactam resistance is also essential for novel phage group infection. An intriguing possibility lies in competition between the phage and PBP2a for a common site of action. Our preliminary studies suggest a phage-antibiotic synergy (PAS) effect of the novel phage group and β-lactam antibiotic (unpublished results; (Kamal F, Dennis J J. Applied Environmental Microbiol 2015; 81:1132-8; Comeau A M et al Med Sci (Paris) 2008; 24:449-51; PMID: 18466714; Comeau A M et al. PloS One 2007; 2:e799; PMID: 17726529). This suggests that the novel phage group would be suitable candidates to augment β-lactam antibiotic treatment and strengthen the notion that the novel phage group is a useful tool to combat the emergence of MDR organisms (data not shown).

Several other studies have identified phage with virulence against methicillin resistant *S. aureus* strains. (O'Flaherty S, et al. Applied Environmental Microbiol 2005; 71:1836-42; PMID: 15812009; Synnott A J, et Applied Environmental Microbiol 2009; 75:4483-90.) However, few studies have identified phage with broad spectrum properties. In this study we have isolated seven *S. aureus* polyvalent phage which possess the potential for use as treatment against antibiotic resistant *S. aureus* infections which may overcome the emergent phage resistance.

Figure 10:
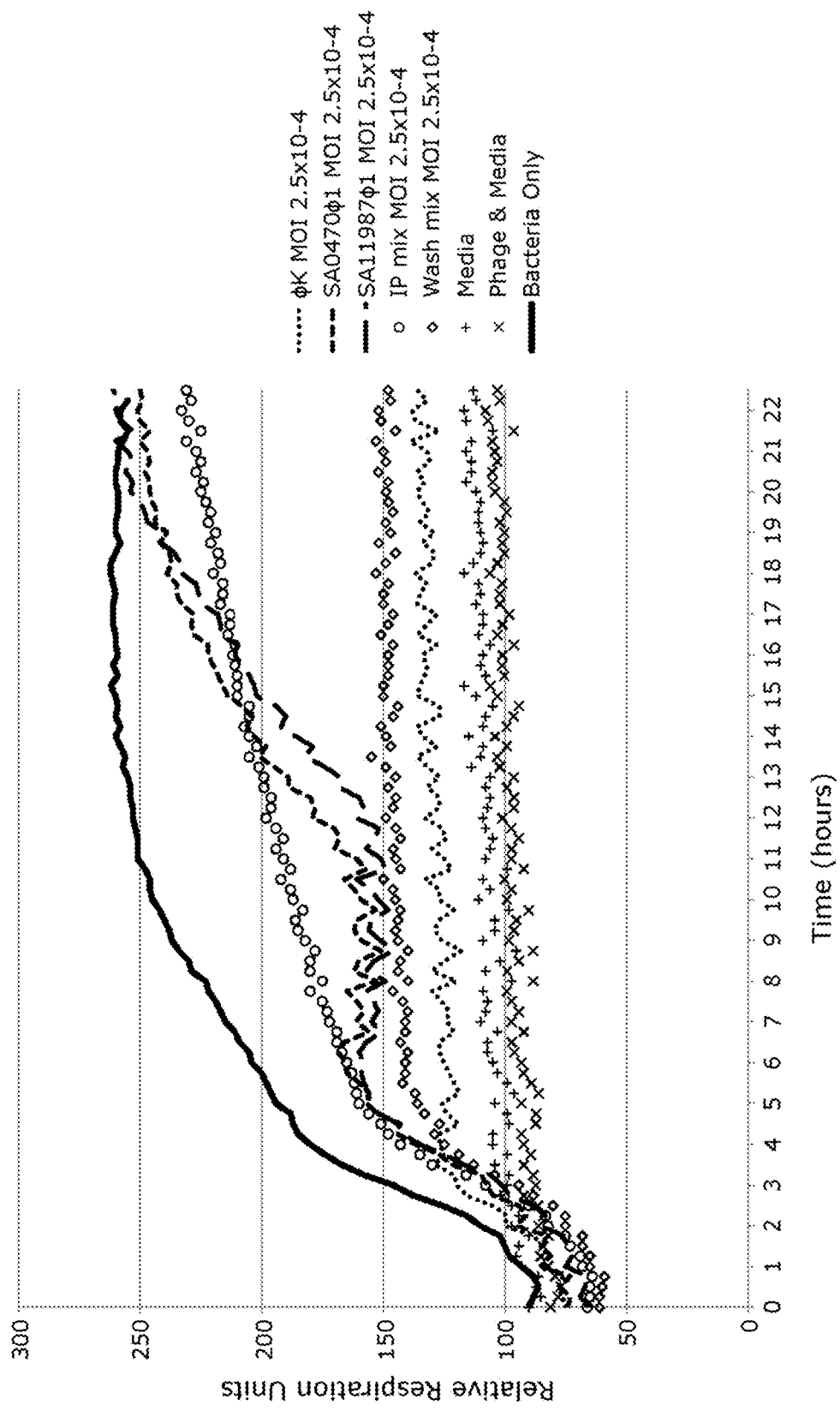
FIG. 10 depicts the measurement of phage activity against *S. aureus* strain Xen36 in the growth assay disclosed in Example 1. Strain Xen36 was tested with $1 \times 10^9$ pfu/mL of phage SA0470$^\Phi$1, SA11987$^\Phi$1 and phage K individually or in a combination mixture for 24 hours at 37° C. "IP Mix" refers to the phage mixture phage K, SA0470$^\Phi$1 and SA11987$^\Phi$1; "Wash Mix" refers to the same phage mixture which was used for a wound wash during an in vivo study (data not shown). The plot includes the lowest effective MOI for each bacteriophage tested.
Figure 11:
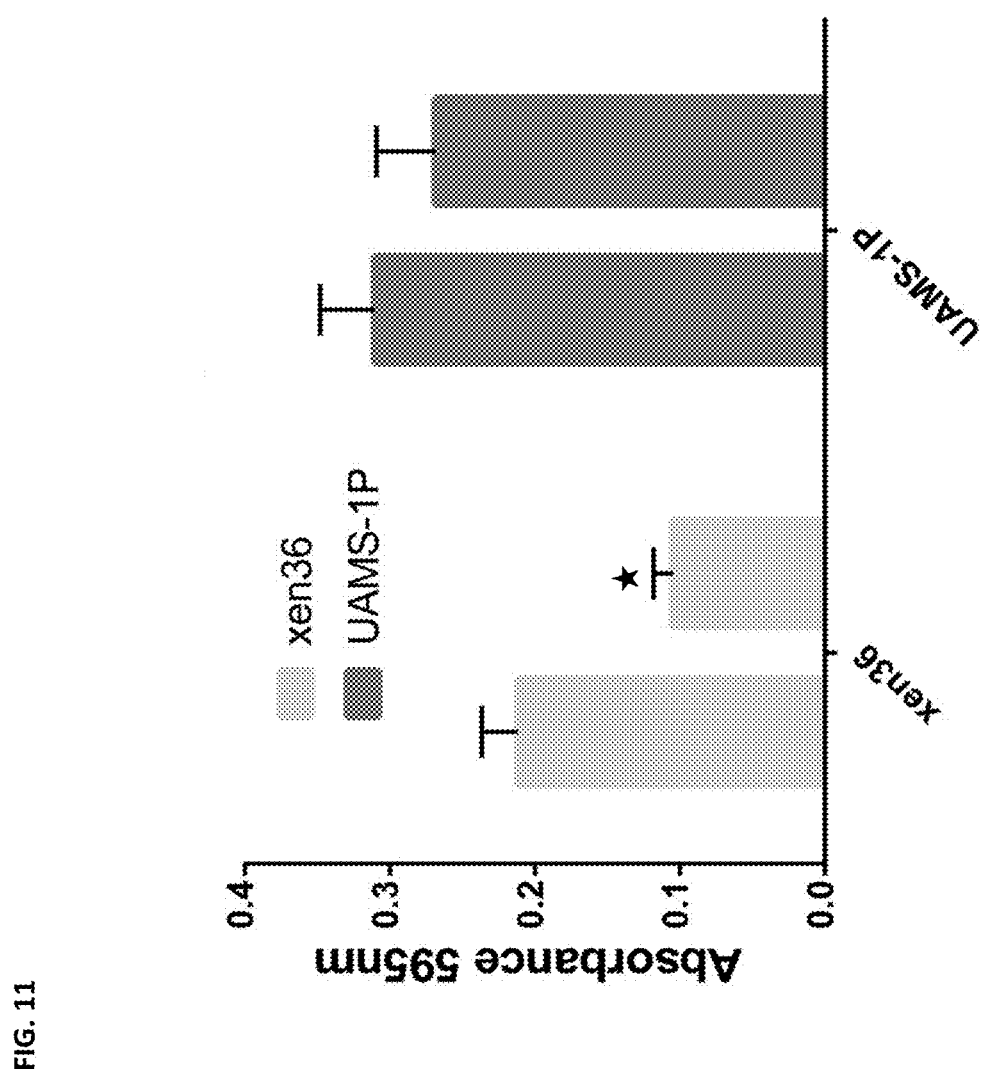
FIG. 11 depicts inhibition of biofilm formation of *S. aureus* strain Xen36 in the presence of a mixture of phage K, SA0470$^\Phi$1 and SA11987$^\Phi$1. The biofilms were incubated with a mixture of phage K, SA0470$^\Phi$1 and SA11987$^\Phi$1 for 24 hours at 37° C. Statistical significance was determined by a Student's t-Test (two tailed), $P<0.05$ (0.0194). The star symbol indicates statistical significance.

Additional studies have indicated that the combination of phage K, SA0470φ1, and SA11987φ1 can produce additive bacterial killing of a clinical strain of *S. aureus*, Xen36, including inhibiting biofilm formation in Xen36 cultures. See FIG. 10 and FIG. 11. In addition, studies indicate that the combination of phage K, SA0420φ1, and SA0482φ1 can also be used to avoid phage resistant growth in *S. aureus* strain NSC0308/MR100 (data not shown.)

Example 4

Vancomycin and Phage Synergy Against Vancomycin-resistant *Enterobacter faecalis* (VRE)

Colonization of the gastrointestinal tract with vancomycin-resistant *Enterococcus faecium* (VRE) has become endemic in many hospitals and nursing homes in the United States. Such colonization predisposes the individual to VRE bacteremia and/or endocarditis, and immunocompromised patients are at particular risk for these conditions. The emergence of VRE requires the exploration of alternative antibacterial therapies, and thus it is contemplated herein that the methods and reagents of the instant invention may also be employed against VRE.

Specifically, as described in detail below and depicted in FIG. 25, we have studied the combinatorial effects of phages on VRE, and confirmed that a combination of phage and vancomycin can be synergistically effective against VRE, and that these data can be detected using the assay in Example 1.

Materials and Methods:

A culture of VRE was first grown in tryptic soy broth (Remel Cat# R455054) to an Optical Density (OD) of 0.5 at 600 nm. Tryptic soy with tetrazolium dye D (BioLog Cat#74224) was added to a 1% v/v ratio and then sterilized through a 0.22 μm filtration unit (Millipore Cat#

SCGP00525). VRE stock phage was serially diluted in tryptic soy broth with dye in separate Eppendorf tubes to a final concentration of $10^7$ pfu/ml. Vancomycin (Sigma, Cat# SBR00001-10 ml) was diluted separately in tryptic soy broth with tetrazolium dye to a concentration equal to 4 times the Minimal Inhibition Concentration (MIC) for the bacteria being used.

Briefly, microtiter plates for the phage-antibiotics synergy assay were prepared as follows. Tryptic soy broth with dye was added to the plate first. Next 50 μl of tryptic soy with tetrazolium dye was added to each well. Vancomycin at a concentration of 4 times the MIC diluted in tryptic soy with tetrazolium dye was added to row A, from column 1 through 8; Vancomycin was added at minimal inhibitory concentration for *E. faecalis*, i.e., 16 μg/ml for each well in which it was added. The wells with Vancomycin were serially diluted 1:1 from row A down to row F. Phage were added to each well starting at $10^7$ pfu/well in column 1 and then serially diluted 1:10 across from column 1 to 6. Individual phage was added at an MOI of 100. Finally all wells were inoculated with approximately $10^4$ cfu of *E. faecalis* bacteria per well. This design allows for antibiotic dilutions going down the columns and dilutions of phage going across the rows. Referring to the description of the "checkerboard assay" in Example 6, columns 7 and 8 represent antibiotic control wells and rows G and H represent phage control wells. However, wells G7, G8, H7, and H8 represent bacteria only control wells. Once all of the wells in the microtiter plate are inoculated with bacteria, the microtiter plates were incubated for 48 hours at 37° C. according to the methods in Example 1. The color change of all plates was recorded every 15 minutes over the course of the 48 hour incubation period.

Results of this experiment clearly indicate that phage and Vancomycin synergistically hold VRE growth, while phage alone or Vancomycin alone were unable to hold the growth of VRE. Specifically, results indicate that alone, VREϕ19 could not delay bacterial growth. VREϕ47 and VREϕ53 used alone could delay bacterial growth by up to 12 hours each. Vancomycin was able to delay bacterial growth for up to 18 hours. When added together, vancomycin and VREϕ19 could delay bacterial growth for up to 21 hours. See FIG. 25. However, vancomycin with either VREϕ47 or VREϕ53, were observed to prevent bacterial growth for over 24 hours.

The results depicted in FIG. 25 also suggest the nature of the stress or pressure on bacterial pathogens by phage cocktails. That is, a phage cocktail may not only have a bactericidal effect, but can render low frequency resistant mutants that eventually emerge less virulent and/or more susceptible to antibiotics. Thus, co-therapy with phage cocktails in the presence of antibiotics can create a synergy with the antibiotics and delay or prevent resistant mutants to the antibiotic from appearing.

Data such as these indicate that successful results obtained with phage therapy that takes place in a human also being treated with antibiotics may be due to the combined effect of the different therapies. As contemplated herein, phage cocktails of the instant invention can be part of a combined antibactericidal therapy, and results assayed as described herein. Notably, as long as the phages utilized are characterized and safe for administration to a subject (e.g. phages from a Tier 2 library), the mechanism of action of the combined therapy need not be solved.

Example 5

Clinical Application of Phage Therapy to Treat a Terminally Ill Patient Who was Infected with Multi Drug Resistant *A. baumannii*

It is contemplated herein that the methods of the instant invention may be used to create a therapeutic phage cocktail for clinical use. In the case described below, some of the reagents and steps of the instant invention were successfully employed towards identifying a therapeutic phage cocktail which was administered to a critically ill patient.

Summary: Upon request from a clinician with a MDR *A. baumannii* clinical isolate ("TP strain/isolate"), the killing efficacy of 98 *A. baumannii* phages (in a Tier 1 phage library) on the TP isolate was evaluated using the high throughput liquid assay described above in Example 1. Specifically, approximately $5 \times 10^4$ cfu bacteria/well were infected with a multiplicity of infection (MOI) of 20 and incubated for 20 hours at 37° C. Bacterial respiration was measured at 15 minute intervals. Assay results indicated that the library contained 10 very virulent phages which very effectively killed the TP isolate. Out of these 10 phages, 4 of the phages were selected to prepare a phage cocktail designed to prevent emergence of phage resistant *A. baumannii* ("Navy phage cocktail 1").

Phage therapy had started as intracavitary instillations at day 109 using the "Texas A&M phage cocktail" (also referred to herein as "ϕPC") containing three new phage isolates (C1P12, C2P21 and C2P24) and phage AC4 from AmpliPhi Corporation (San Diego, Calif.). Intravcavitary installations were continued at 6-12 hourly intervals. During this time the patient was unresponsive to commands and had developed renal failure with a creatinine of 3.68 mg/dL. Over the next 36 hours his clinical condition was stable but he remained comatose, intubated and on three pressors with worsening renal and hepatic function. After 36 hours of initiation of intracavitary instillations of the phage cocktail, phage therapy was introduced through intravenous administration of an additional phage cocktail ($5 \times 10^9$ pfu/dose) consisting of four different anti-*A. baumannii* bacteriophages (Abϕ1, Abϕ4, Abϕ71, Abϕ97 or "Navy phage cocktail 1").

Intravenous administration of phage cocktails was well tolerated. After intravenous administration of Navy phage cocktail 1, the patient's pressor requirements diminished and he abruptly awoke from his coma and became conversant with his family for the first time in several weeks. When reduced phage susceptibility of serial isolates of the patient's *A. baumannii* was detected in vitro, a new Navy phage cocktail of AbTP3ϕ1 in combination with Abϕ71 was developed and used for treatment ("Navy phage cocktail 2"). Two days later it was discovered that the patient's *A. baumannii* was once again susceptible to minocycline and that antibiotic was added to his regimen at that time. The combinations of intracavitary and IV therapy with phage cocktails were continued (generally at 6-8 hourly intervals). Over the ensuing three weeks, patient's mental status continued to improve and he was fully conversant and lucid. He was weaned off the ventilator and his pressors were gradually weaned and were discontinued. Patient's renal function gradually improved to the point that it had fallen to 1.1 mg/dL. Phage therapy was continued for additional 8 weeks. The patient demonstrated continued clinical improvement over the next two months and he was discharged home on Aug. 12, 2016.

As discussed in detail in the case report below, Navy phage cocktail and Navy phage cocktail 2 were generated using a subset of the methods of the instant invention, namely a Tier 1 *A. baumannii* phage library was screened to identify phages with a sufficient hold-time against the targeted pathogen, and a subset of these phages were compounded into cocktails.

Materials and Methods:

Identification and Purification of Anti-*A. baumannii* Bacteriophages:

Phages identified at the Center for Phage Technology at Texas A&M University and purified at San Diego State University were obtained from multiple academic, clinical and corporate sources, including 37 phages that had been previously isolated against *A. baumannii* strains using conventional methods. Only one of these phages, AC4 from AmpliPhi Corporation, was fully active against a pre-therapy isolate from the patient (TP1), with raw phage lysates producing $\sim 10^9$ pfu/ml. Another 100 environmental samples available at the Center were screened by enrichment (Carmody L A, et al. J Infect Dis. 2010; 201(2):264-71. Epub 2009/12/17 doi: 10.1086/649227) yielding three new isolates (C1P12, C2P21 and C2P24) with the same plating capability as AC4. Working stocks were prepared by plate lysates grown from single plaques. Large volume phage stocks were prepared by infecting mid-log 1 liter SB cultures of the host strain at an input MOI~$<10^{-2}$ in the presence of 5 mM $MgSO_4$. The infected cultures were grown until lysis onset, as measured by A550, at which time Na citrate was added to final 10 mM. The infected culture was aerated until lysis was complete. Lysates were cleared by centrifugation (6000 g, 40 min) in the cold and sterilized by filtration through 0.22 mm membranes. Phages were harvested by centrifugation at 6000 g for 10 hrs in the cold. Phage pellets were gently resuspended in 10 ml of DPBS, sterilized again by filtration, and subjected to octanol extraction to remove lipopolysaccharide (LPS) (Bonilla N, et al. Peer J. 2016; 4: e2261. doi: 10.7717/peerj 0.2261). These three phages were combined with the AmpliPhi phage to comprise a 4-phage cocktail that was used for intracavitary therapy ($\phi$PC).

Phages provided by the Biological Defense Research Directorate of the Naval Medical Research Center were originally isolated from various environmental samples using routine isolation techniques as previously described (Biswas B, et al. Infection and immunity 2002; 70:204-10).

*A. baumannii* Susceptibility to Phages:

Ninety-eight *A. baumannii* isolates from a Tier 1 phage library were initially screened by monitoring the growth of the *A. baumannii* clinical isolates (TP1 and TP3) in the presence of phage using the high throughput assay described in Example 1. The most virulent phage candidates (Ab$\phi$1, Ab$\phi$4, Ab$\phi$71, Ab$\phi$97 against strain TP1 and AbTP3$\phi$1 against strain TP3) were selected for addition to the therapeutic cocktails.

Large scale phage amplification of each phage strain before purification was performed in two steps. First, initial amplification of the triply plaque-purified phage (via a plate lysate method) was followed by a 3.6 L large-scale liquid lysate preparation where phages produced were used as seed cultures (Biswas, B et al. Infection and Immunity 2002; 70:204-10.) Approximately 3.6 L of each phage lysate preparation was centrifuged at 10,000 g for 20 minutes to remove bacterial debris and the lysate was further filtered through 0.22 μm vacuum filters and concentrated using a Millipore Pelican 2 cassette, 300K MWCO tangential flow filtration system to a volume of approximately 0.5 L. Following concentration, the culture medium was replaced with PBS via diafiltration. The resulting lysate was further concentrated to a final volume of 0.2 L prior to collection. Finally, the concentrated phage mixture was purified using cesium chloride (CsCl) density gradient centrifugation (Sambrook J, Fritsch E F, Maniatis T, Molecular cloning: A laboratory manual. New York: Cold Spring Harbor Laboratory Press; 1989) and subsequently dialyzed in PBS to remove cesium chloride. Purified phages were combined into a four-phage cocktail designated "Navy phage cocktail 1" containing Ab$\phi$1, Ab$\phi$4, Ab$\phi$71, Ab$\phi$97.

After the patient's *A. baumannii* became insensitive to Navy phage cocktail 1, a second phage cocktail was prepared by combining Ab$\phi$71 from the original cocktail with a newly isolated phage (AbTP3$\phi$01) that was capable of lysing *A. baumannii* TP3 and referred to as "Navy phage cocktail 2".

Host Range Analysis of a Phage Cocktail Against an *A baumannii* Diversity Set:

Different *A. baumannii* isolates in a bacterial diversity set (total 93 isolates) were tested against Navy phage cocktail 1 (Ab$\phi$1 Ab$\phi$4 Ab$\phi$71 and AbT$\phi$497). Approximately $10^4$ cfu bacteria/well were infected with a multiplicity of infection (MOI) of 10,000 and incubated for 72 hours at 37° C. Bacterial respiration was measured at 15 minute intervals using the assay described in Example 1 which monitors a colorimetric redox reaction of a tetrazolium based dye. Result indicated that this cocktail was effective to prevent the growth of 9 *A. baumannii* clinical isolates in our collection (data not shown.)

Transmission Electron Microscopy:

*A. baumannii* phages were grown on their corresponding host by standard procedures and purified via CsCl density gradient centrifugation (Sambrook J, Fritsch E F, Maniatis T, Molecular cloning: A laboratory manual. New York: Cold Spring Harbor Laboratory Press; 1989.) The inactivated preparation was spread onto electron microscope grids, negatively stained with uranyl acetate, and imaged with a FEI Tecnai T12 transmission electron microscope.

Endotoxin Estimations of the Navy Phage Cocktails:

Endotoxin estimations of the phage cocktails used in this example were determined using a Lonza Endpoint Chromogenic LAL Assay-QCL-1000 300 Test Kit Cat#50-648U.

Detailed Clinical Course:

A 68-year old diabetic man developed gallstone-induced acute pancreatitis while vacationing in Egypt during November, 2015. After stabilization in an Egyptian hospital, he was airlifted to a hospital in Germany where an abdominal CT scan revealed a pancreatic pseudocyst. Pseudocyst fluid obtained through two pigtail cystgastrostomy tubes grew *Candida albicans* and MDR *A. baumannii*. The patient was hydrated and received courses of vancomycin, meropenem, colistin, and tigecycline. The organism was initially susceptible to colistin and tigecycline but resistance developed while receiving these antibiotics. He was airlifted to University of California San Diego (UCSD) Medical Center on Day 15 of his illness arriving with a diffusely tender abdomen and a leukocyte count of 14,900. An abdominal CT scan revealed a large fluid collection adjacent to the pancreas measuring 14.5×8.8×5.7 cm with adjacent fluid and fat stranding, compatible with a pancreatic pseudocyst. The pancreatic parenchyma was mottled but demonstrated normal enhancement with no evidence of pancreatic necrosis. Ascites and a fatty liver were also noted. The CT scan also revealed that the pseudocyst was connected to the gastric lumen via a double pigtail cystgastrostomy tube, and a pancreatic stent was in place with some associated pneumobilia.

Another culture of the pseudocyst obtained from a percutaneous drain grew *A. baumannii* resistant to cephalosporins, meropenem, gentamicin, amikacin, trimethoprim/sulfamethoxazole, tetracycline, ciprofloxacin and colistin.

*Candida glabrata* and MDR *A. baumannii* were also isolated from a subhepatic fluid collection on day 34. Susceptibility testing revealed synergy between colistin and azithromycin against the MDR *A. baumannii* (Lin et al. EBioMedicine 2015; 2:690-8), and treatment with these two antibiotics was initiated on day 36. Multidrug MDR *A. baumannii* was repeatedly isolated from multiple abdominal drains, and the patient developed worsening delirium that was attributed to a combination of metabolic factors, depression, medications and uncontrolled infection.

The patient's clinical condition deteriorated acutely on day 51 and his percutaneous pseudocyst drain produced several liters of fluid. He developed respiratory failure and hypotension requiring intubation, fluid resuscitation, pressors and emergent transfer to the ICU. *Bacteroides fragilis* grew from blood cultures. The percutaneous pseudocyst drainage catheter had become displaced into the peritoneal cavity and his peritoneal cavity was presumed infected with organisms previously contained in his pancreatic pseudocyst. Rifampin was determined in vitro to provide added antibiotic synergy against the MDR *A. baumannii* and it was therefore included in his regimen.

The patient continued to deteriorate over the subsequent two months of his hospitalization despite intensive antibiotic therapy. He developed emphysematous cholecystitis on day 68 and *A. baumannii* and *B. fragilis* were grown from a cholecystostomy drain. Low-grade fever persisted and he became increasingly delirious with declining renal function and increasing leucocyte counts. Cultures of multiple drains, peritoneal fluid and respiratory secretions all produced MDR *A. baumannii*. Blood pressure support and pressors were intermittently required. A blood cultures on day 96 grew *Candida glabrata*. Renal and hepatic function worsened.

By day 108 he was on multiple pressors, unresponsive, with a plasma creatinine of 3.68 mg/dl. In the face of maximal supportive care and absent additional antimicrobial agents at our disposal, an Emergency Investigational New Drug Application was submitted to the Food and Drug Administration requesting authorization to treat his uncontrolled *A. baumannii* infection with a combination of phages.

Phage therapy was initiated on day 109 with the installation of phage cocktail "φPC" containing four of anti-*A. baumannii* phages (~$10^9$ pfu/dose of (PC) through percutaneous catheters draining the pseudocyst cavity, the gall bladder and a third intra-abdominal cavity. Intracavitary instillations of this cocktail were continued at 6-12 hourly intervals. Over the next 36 hours the patient remained comatose, intubated and on three pressors with worsening renal and hepatic function. Therefore, phage therapy was intensified and broadened with an additional phage cocktail, "Navy phage cocktail 1" consisting of four additional anti-*A. baumannii* phages (~$10^9$ pfu/dose of Navy phage cocktail 1) that was administered intravenously beginning on day 111. Since this was well tolerated, IV phage therapy was repeated at increasingly frequent intervals over the next two days. On day 113 his pressor requirements diminished and he abruptly awoke from his coma and recognized his daughter for the first time in several weeks. Azithromycin, colistin and rifampin were discontinued; meropenem and fluconazole were continued. However, the following morning, his pressor requirements abruptly increased and, although the acute deterioration was most consistent with bacterial sepsis, concerns were raised that his clinical deterioration might be attributable to the escalation of his phage therapy. Phage therapy was withheld, and blood cultures were obtained and his meropenem dose was increased. Blood cultures subsequently grew *Bacteroides thetaiodomicron* and his clinical improvement continued. On day 115 a previously obtained *A. baumannii* isolate was found to be susceptible to minocycline at 3 μg/mL and minocycline was added to his regimen. Intracavitary and intravenous phage therapy was resumed on days 116 and 118, respectively.

Over the next three weeks, his course remained complex but he generally demonstrated ongoing improvement. He was weaned off the ventilator and his creatinine fell to 1.92 mg/dL by day 126. On day 128 the cholecystostomy drain was accidently removed and one blood culture grew a minocycline susceptible *A. baumannii*. The drain was repositioned and the organism was no longer isolated from his bloodstream although it continued to be isolated from percutaneous drainage catheters. Beginning on day 139 the Navy phage cocktail 1 was also added to the intracavitary instillations. Pressors were gradually weaned and discontinued on day 143.

Combinations of intracavitary and intravenous therapy with φPC and Navy phage cocktail 1, respectively, were continued (generally at 6-8 hourly intervals) until day 174. An *A baumannii* isolate obtained on day 171 had become resistant to minocycline. When reduced susceptibility of serial isolates of the patient's *A. baumannii* was demonstrated in vitro, a third phage cocktail (designated Navy phage cocktail 2) was developed to effectively target the phage-resistant bacterial isolate and administered during the last two weeks of therapy.

With ongoing clinical improvement minocycline and meropenem were discontinued on day 175 and 185, respectively. Three *A. baumannii* isolates obtained the day after discontinuing minocycline were resistant to minocycline but an isolate obtained 12 days later was again susceptible to minocycline. This isolate from 198 was the last isolate of *A. baumannii* obtained from any site. The patient demonstrated continued clinical improvement over the next two months. All drains were removed by day 257. He was discharged home on day 259.

Figure 12:
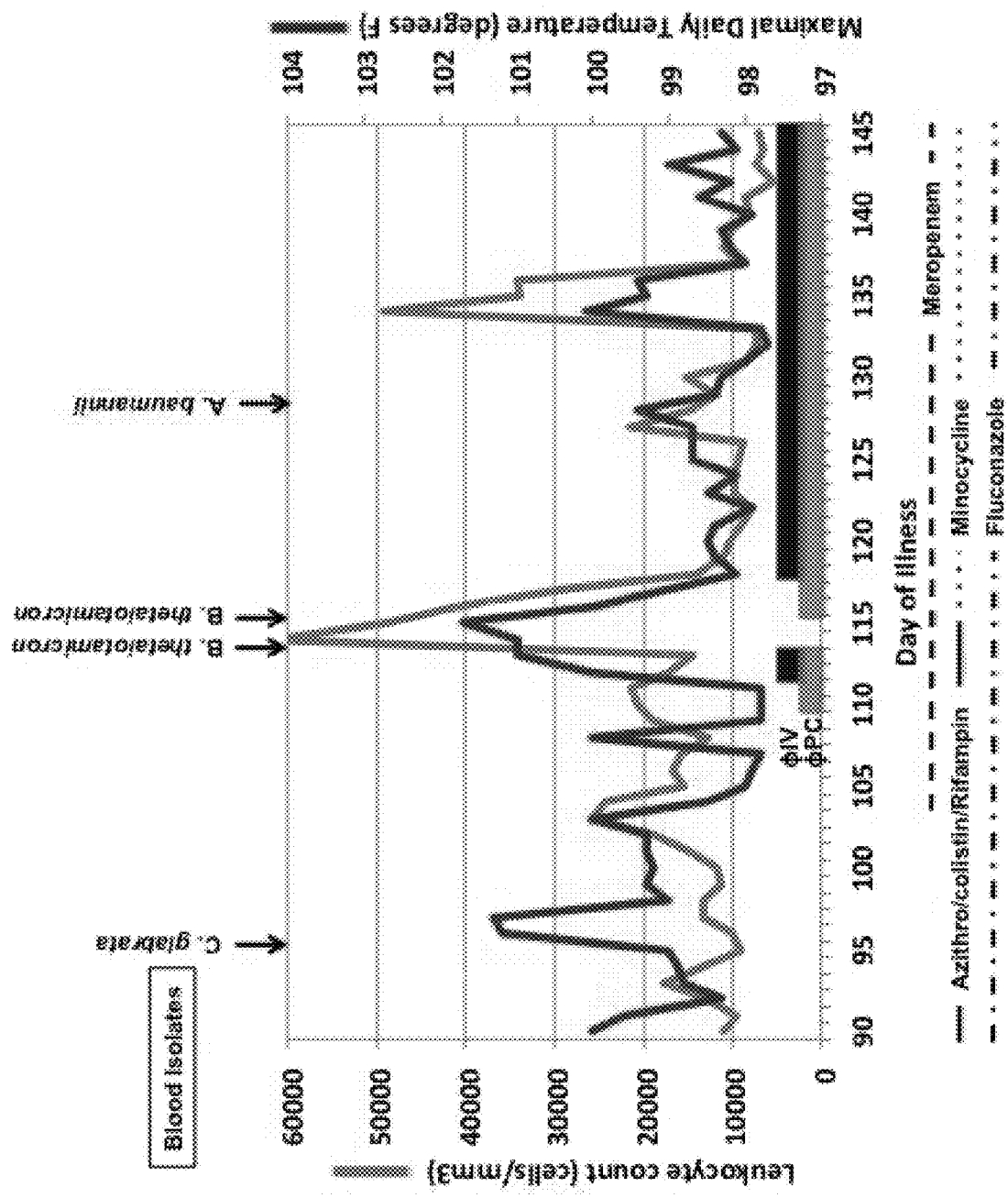
FIG. 12 depicts the clinical course before and during the initial phase of bacteriophage therapy for the case report described in Example 5. Selected blood and peritoneal fluid cultures are depicted above the graphic data. Antibiotic and phage administration are indicated below the graphic data. A/C/R is an abbreviation for Azithromycin/Colistin/Rifampin. The darker line corresponds to the daily maximal fever and the lighter line corresponds to the white blood cell count. As depicted, "ϕIV" is Navy phage cocktail 1; "ϕPC" is also referred to herein as the "Texas A&M cocktail."
Figure 15B:
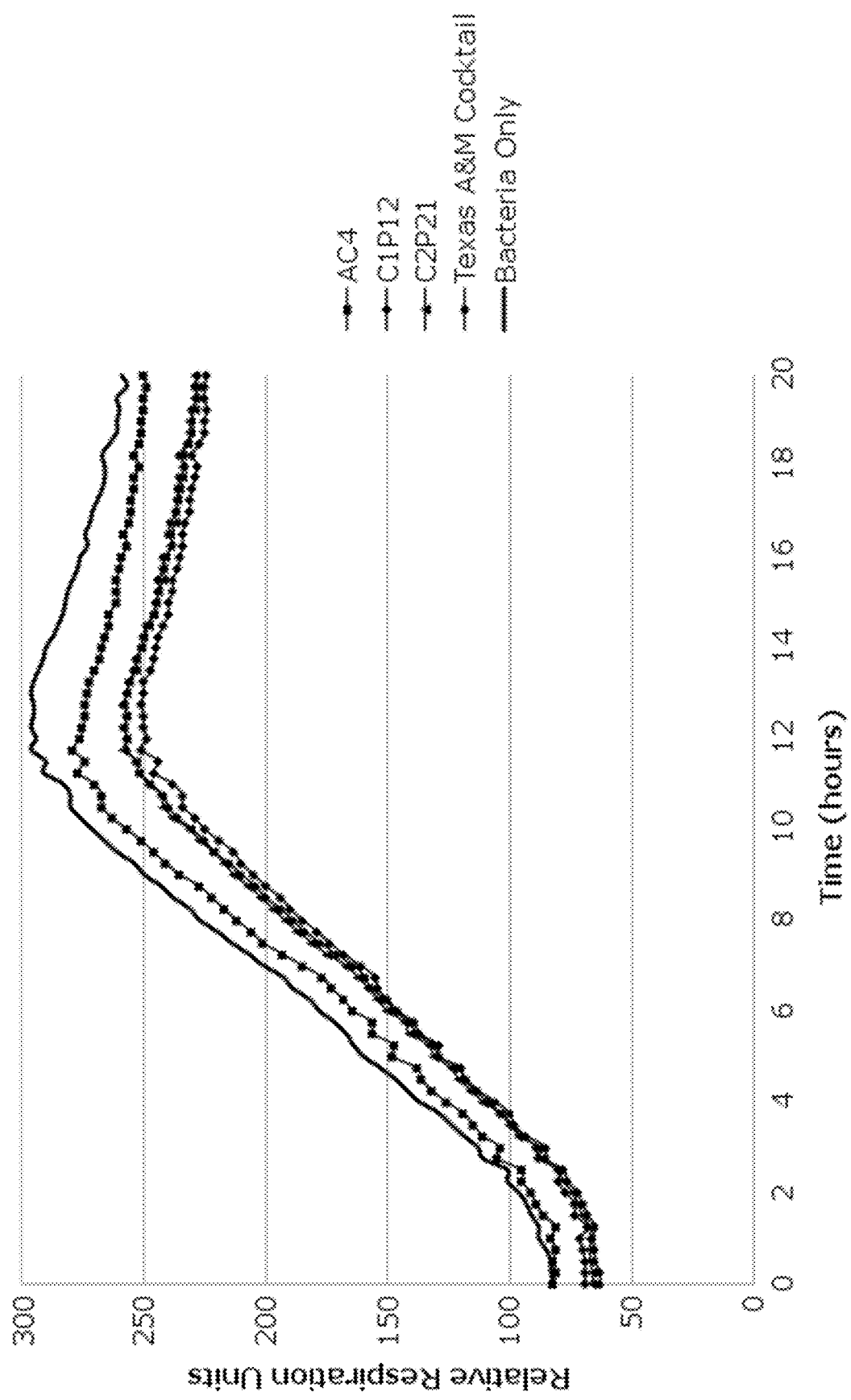

Results:

FIG. 12 depicts the clinical course before and during the initial phase of bacteriophage therapy. Clinical isolates harvested before and after phage therapy are provided in FIG. 13. Clinical details of the phage therapy (dose/day) are provided in FIG. 14. FIG. 15A, FIG. 15B, FIG. 15C, FIG. 15E, FIG. 15F, FIG. 15G depict the activity of phage cocktails φPC and Navy Phage cocktail 1 (referred to therein as "AbφMIX") against serial isolates of *A. baumannii* isolated from intra-abdominal drains before bacteriophage therapy (strainTP1) (FIG. 15A and FIG. 15E), and four days (Strain TP2; FIG. 15B and FIG. 15C) and eight days (Strain TP3; FIG. 15F and FIG. 15G) after initiation of bacteriophage therapy. FIG. 16 depicts the phage titer from plasma samples during phage therapy.

Endotoxin estimations of the phage cocktails for the patient are provided in Table 3 below. (The FDA recommended guideline is 5 EU/kg/hour; 75 kg body weight×5 EU/kg/hour=375 EU/hour.)

TABLE 3

Endoxotin Estimations

| Navy Phage Cocktail | Purification Method | Endotoxin Estimation |
|---|---|---|
| #1: ABΦ1 + ABΦ4 + ABΦ71 + ABΦ97 | TFF | $1.4 \times 10^5$ EU/ml |
| #2: ABΦ1 + ABΦ4 + ABΦ71 + ABΦ97 | CsCl density gradient | $5.8 \times 10^3$ EU/ml |
| #3: ABΦ71 + ABTP3Φ1 | TFF & CsCl density gradient | $1.6 \times 10^3$ EU/ml |

*A. baumannii* Susceptibility to Phages:

Each of the phages used clinically (separately and in combination) demonstrated antimicrobial activity against the patient's pre-phage therapy *A. baumannii* isolate. With continued treatment, in vitro susceptibility studies of serial *A. baumannii* isolates demonstrated stepwise selection of resistance to the eight phages in the original therapeutic cocktails. Representative data related to the antimicrobial activity of the phages comprising the Navy phage cocktail 1 and ϕPC cocktails over the initial three weeks of therapy are presented in FIG. 15A-15C and FIG. 15E-15G, respectively.

As depicted in FIG. 15A, Phage C1P12, C2P21, and the Texas A&M phage cocktail prevented bacterial growth for approximately 10 hours. However, phage AC4 alone could prevent bacterial growth for approximately 13 hours. As depicted in FIG. 15B, Phage AC4, C1P12, C2P21, and the Texas A&M phage cocktail could not prevent or delay the normal growth of the *A. baumannii* TP2 strain. As depicted in FIG. 15C, Phage AC4, C1P12, C2P21, and the Texas A&M phage cocktail could not prevent or delay the normal growth of the *A. baumannii* TP3 strain.

Figure 15D:
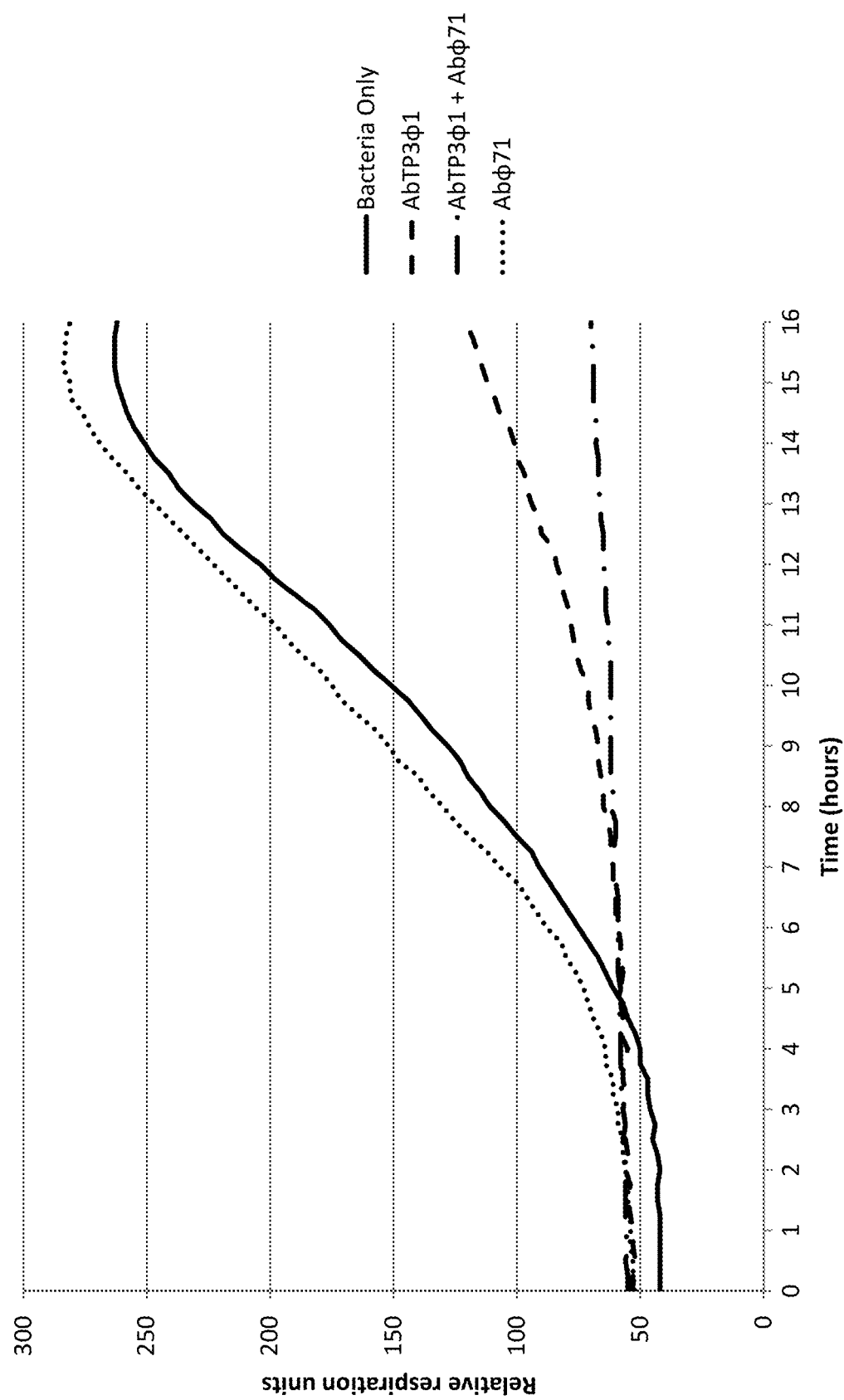

With regard to FIG. 15D, approximately $10^5$ cfu bacteria/well were infected with a multiplicity of infection (MOI) of 100 and incubated for 20 hours at 37° C. Bacterial respiration was measured at 15 minute intervals using the assay described in Example 1. Results in FIG. 15D indicate that phage Abϕ71 was not effective for holding the growth of TP2 isolate where as AbTP3ϕ1 was partially effective to hold the bacterial growth. However, a cocktail of AbTP3ϕ1 and Abϕ71 was effective to hold the growth of the TP3 isolate.

Figure 15E:
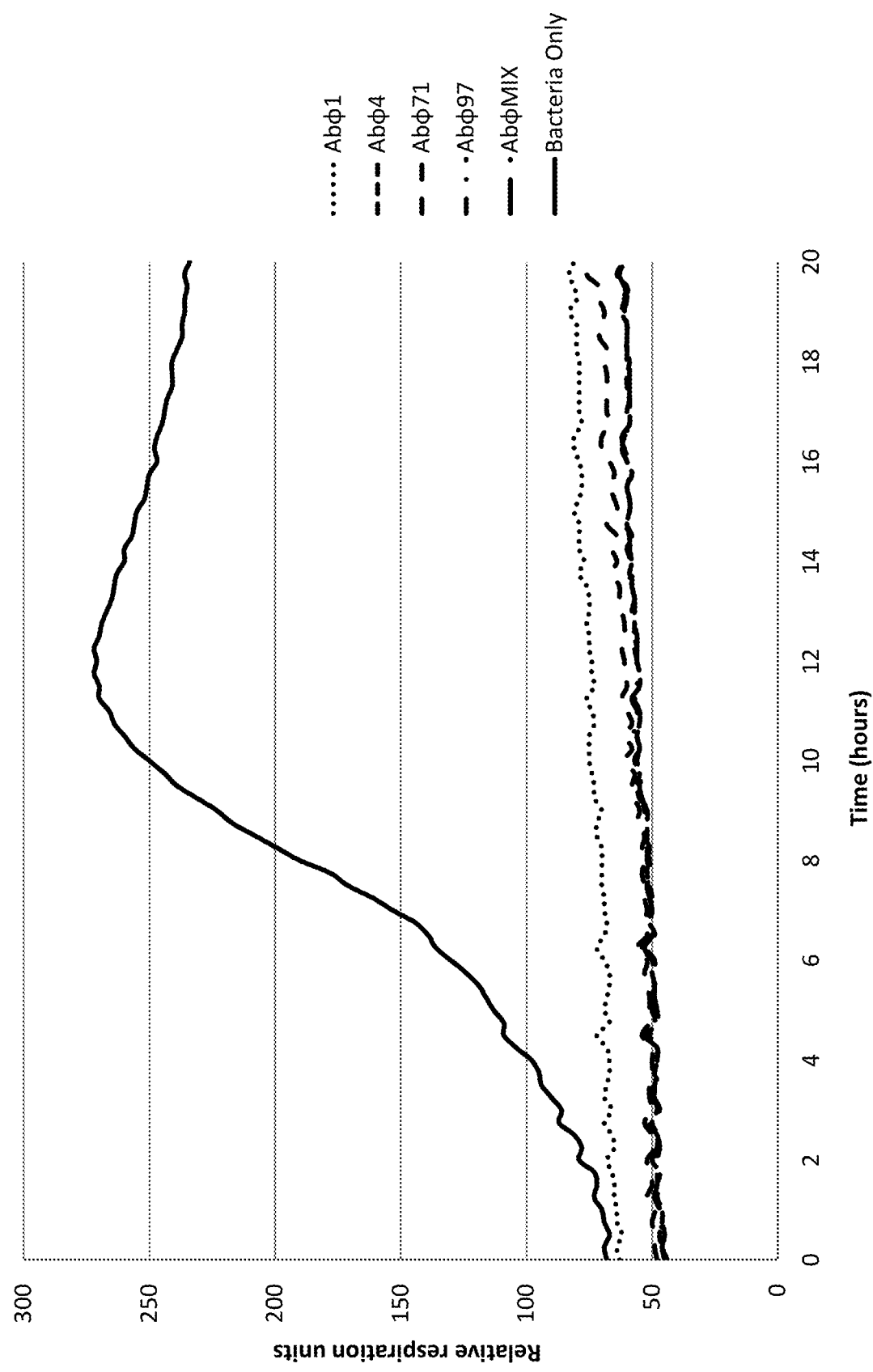
Figure 15F:
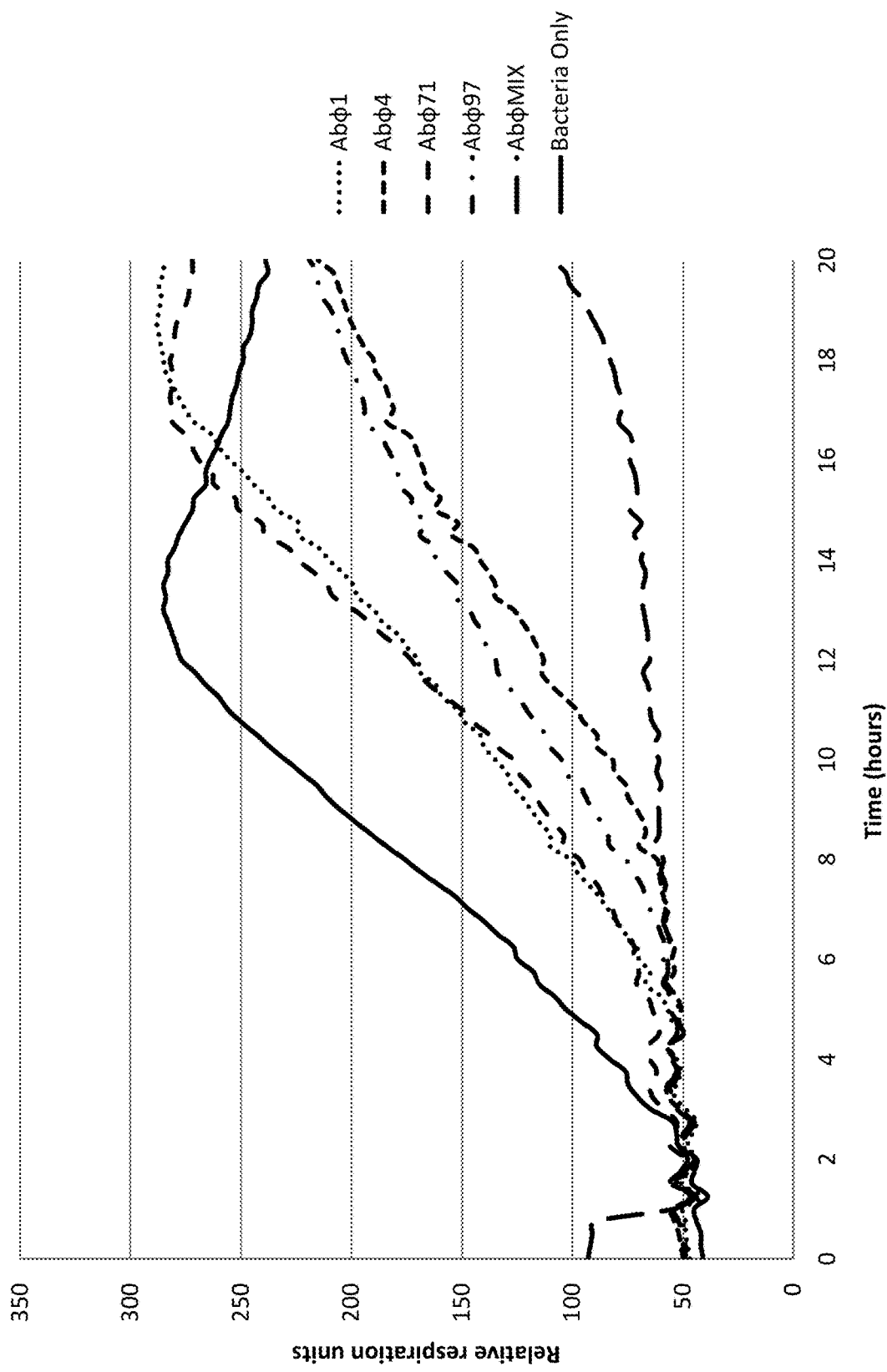
Figure 15G:
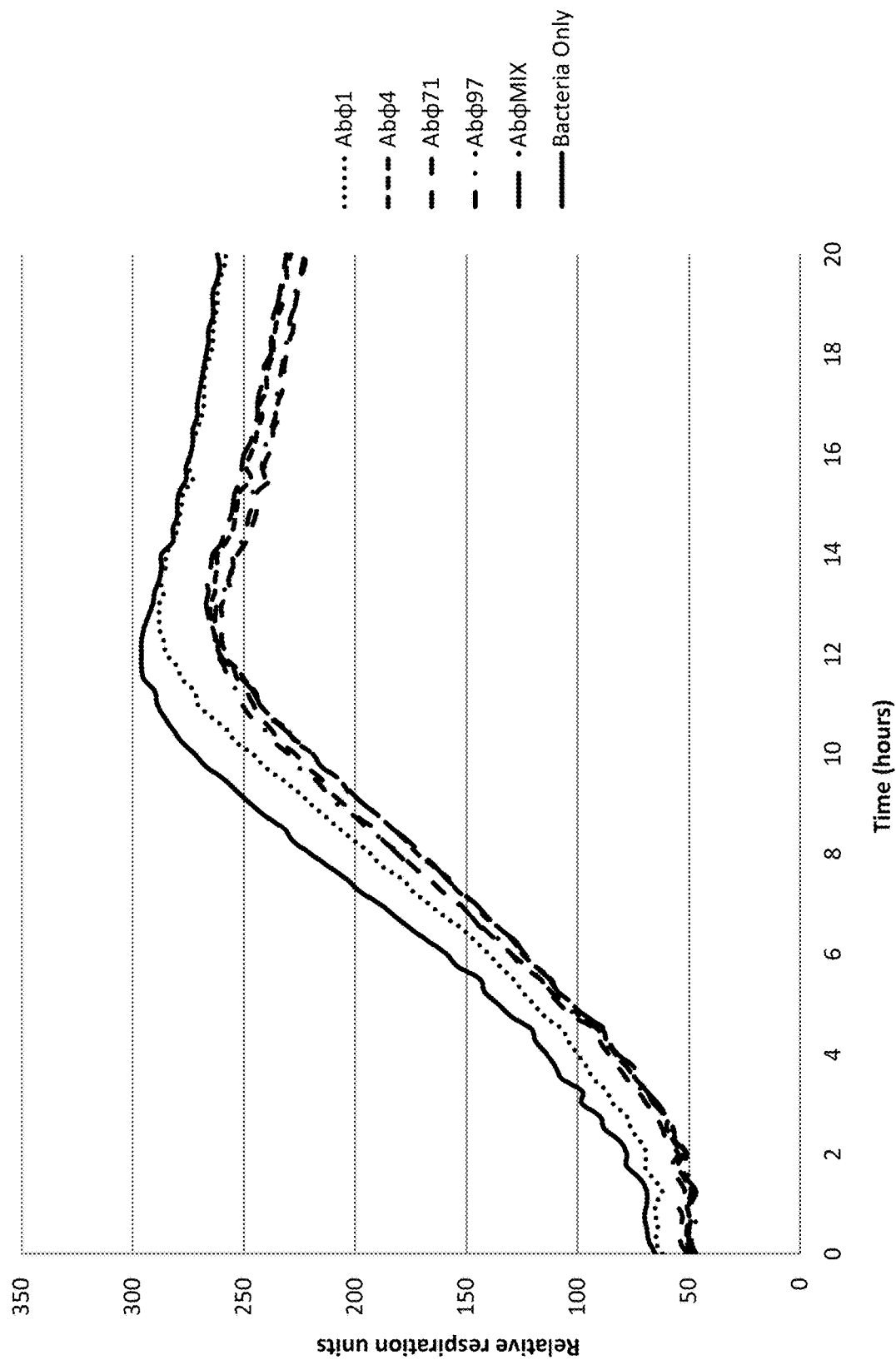
Figure 16:
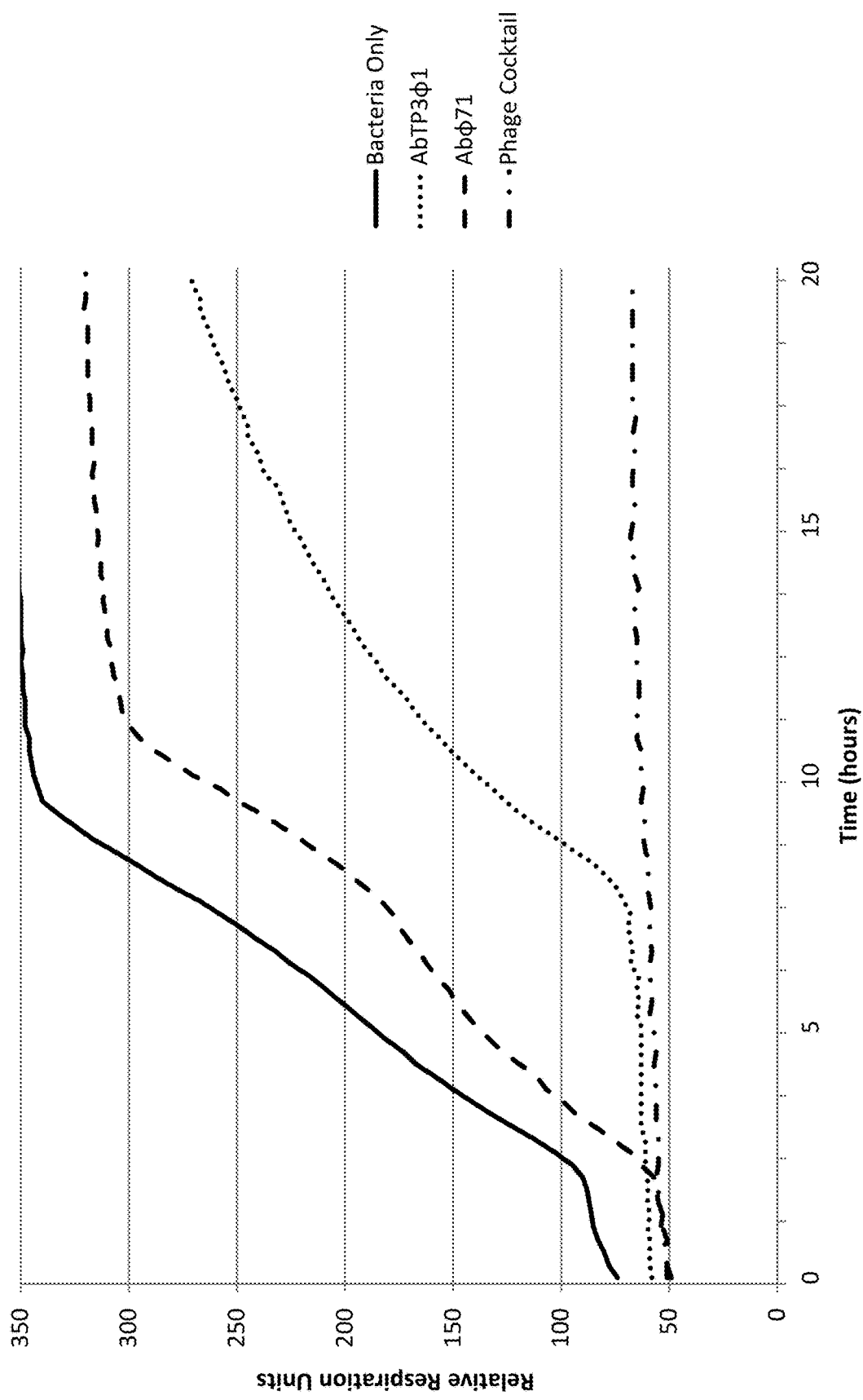
FIG. 16 is a graph which depicts the synergy observed between Abϕ71 and AbTP3ϕ1 discussed in Example 5. The y axis represents relative respiration units; the x axis indicates time (in hours). As indicated, data is provided for bacteria only (solid line), AbTP3ϕ1 (dotted line), Abϕ71 (dashed line), and the phage cocktail of Abϕ71 and AbTP3ϕ1 (dotted and dashed line). As depicted therein, TP3 was ABϕ71 resistant. However, TP3 was completely susceptible to the phage cocktail of ABϕ71+ABTP3ϕ1.

With regard to FIG. 15E, approximately $10^5$ cfu bacteria/well were infected with a multiplicity of infection (MOI) of 100 and incubated for 20 hours at 37° C. Bacterial respiration was measured at 15 minute intervals in the assay described in Example 1. Results indicate that all phages were capable to hold the growth of TP1 isolate. Thus, data indicate that the bacteria were completely susceptible to all phages including the phage cocktail.

With regard to FIG. 15F, approximately $10^5$ cfu bacteria/well were infected with a multiplicity of infection (MOI) of 100 and incubated for 20 hours at 37° C. Bacterial respiration was measured at 15 minute intervals using the assay described in Example 1. This result indicated that phages were partially effective for holding the growth of TP2 isolate.

With regard to FIG. 15Q approximately $10^5$ cfu bacteria/well were infected with a multiplicity of infection (MOI) of 100 and incubated for 20 hours at 37° C., and bacterial respiration was measured at 15 minute intervals using the assay described in Example 1. These results indicate that phages were ineffective for holding the growth of TP3 isolate after emergence of phage resistant bacteria after initial phage treatment.

By day 8 of phage therapy, each of the phages had lost activity individually and in their respective cocktails against the *A. baumannii* isolates that emerged in the presence of the phages. After it was discovered that an *A. baumannii* (TP3) isolated on day 8 of phage therapy had become resistant to both of the initial phage cocktails (ϕPC and Navy phage cocktail 1), that isolate was used to select for additional phages with lytic activity against this isolate. An additional phage (designated AbTP3ϕ1) inhibited isolate TP3 when combined with phage Abϕ71 from the original Navy phage cocktail 1. The phage sensitivity of the *A. baumannii* TP3 isolate is depicted in FIG. 16. As depicted therein, TP3 was ABϕ71 resistant. However, TP3 was completely susceptible to the phage cocktail of Abϕ71+ABTP3ϕ1.

Figure 15H:
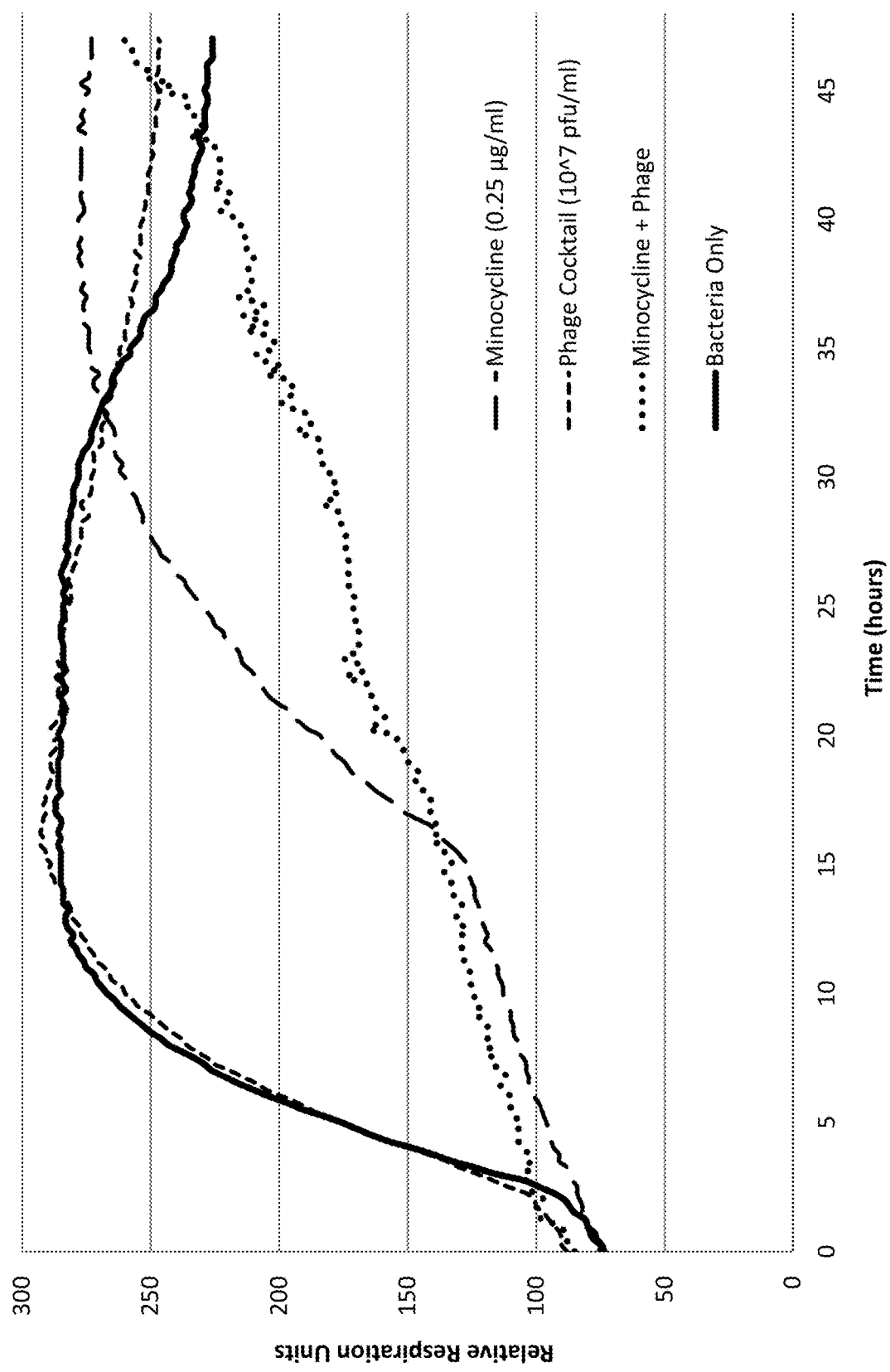

The activity of Navy phage cocktail 1 was tested in combination with different concentrations of minocycline to determine whether the phage cocktail affected the activity of sub-minimum inhibitory concentrations (MIC) of the drug. These data are depicted in FIG. 15H and also discussed in Example 6. With regard to FIG. 15H, approximately $10^5$ cfu bacteria/well were infected with a multiplicity of infection (MOI) of 100 and incubated for 20 hours at 37° C. Bacterial respiration was measured at 15 minute intervals using the assay described in Example 1. As discussed in Example 6, a "checkerboard assay" was used to monitor the effect of Navy phage cocktail 1 and Minocycline on TP3 isolates. Results indicated that the Navy phage cocktail 1 and antibiotic produced an additive effect on the TP3 isolate. Notably, although Navy phage cocktail 1 itself had lost activity against the organism, Navy phage cocktail 1 appeared to prevent the outgrowth of bacteria when added to a sub-inhibitory concentration of minocycline.

Figure 17:
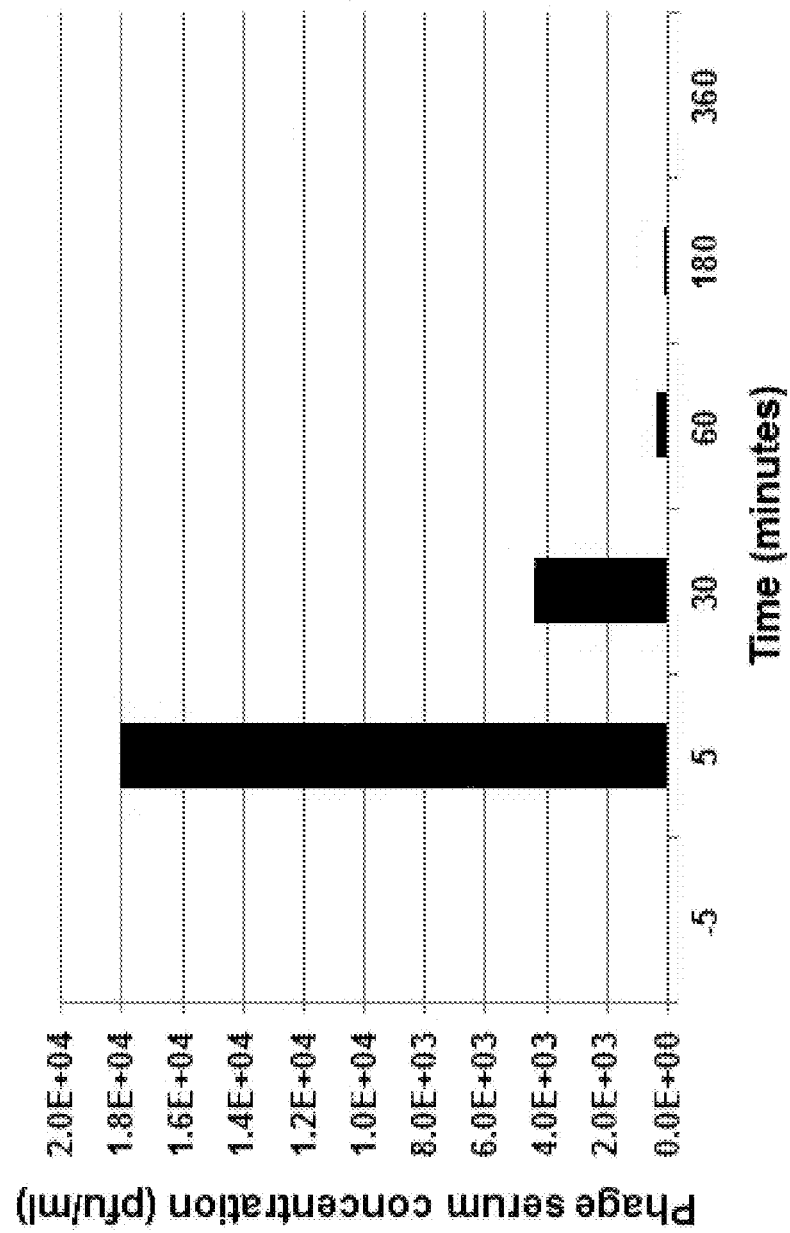
FIG. 17 depicts the phage titer from plasma samples during phage therapy discussed in Example 5. Plasma sample collected 5 minutes prior and following administration of $5 \times 10^9$ pfu of phage via intravenous injection indicated that phage titers in systemic circulation increase rapidly from 0 pfu/ml to $1.8 \times 10^4$ pfu/ml. Phage titer dropped to $4.4 \times 10^3$ pfu/ml, $3.3 \times 10^2$ pfu/ml, 20 pfu/ml within 30, 60 and 120 minutes, respectively, post injection. Plasma samples collected 6 hours following initial injection contained no detectable phage titer (limit of phage detection was 20 pfu/ml).
Figure 18:
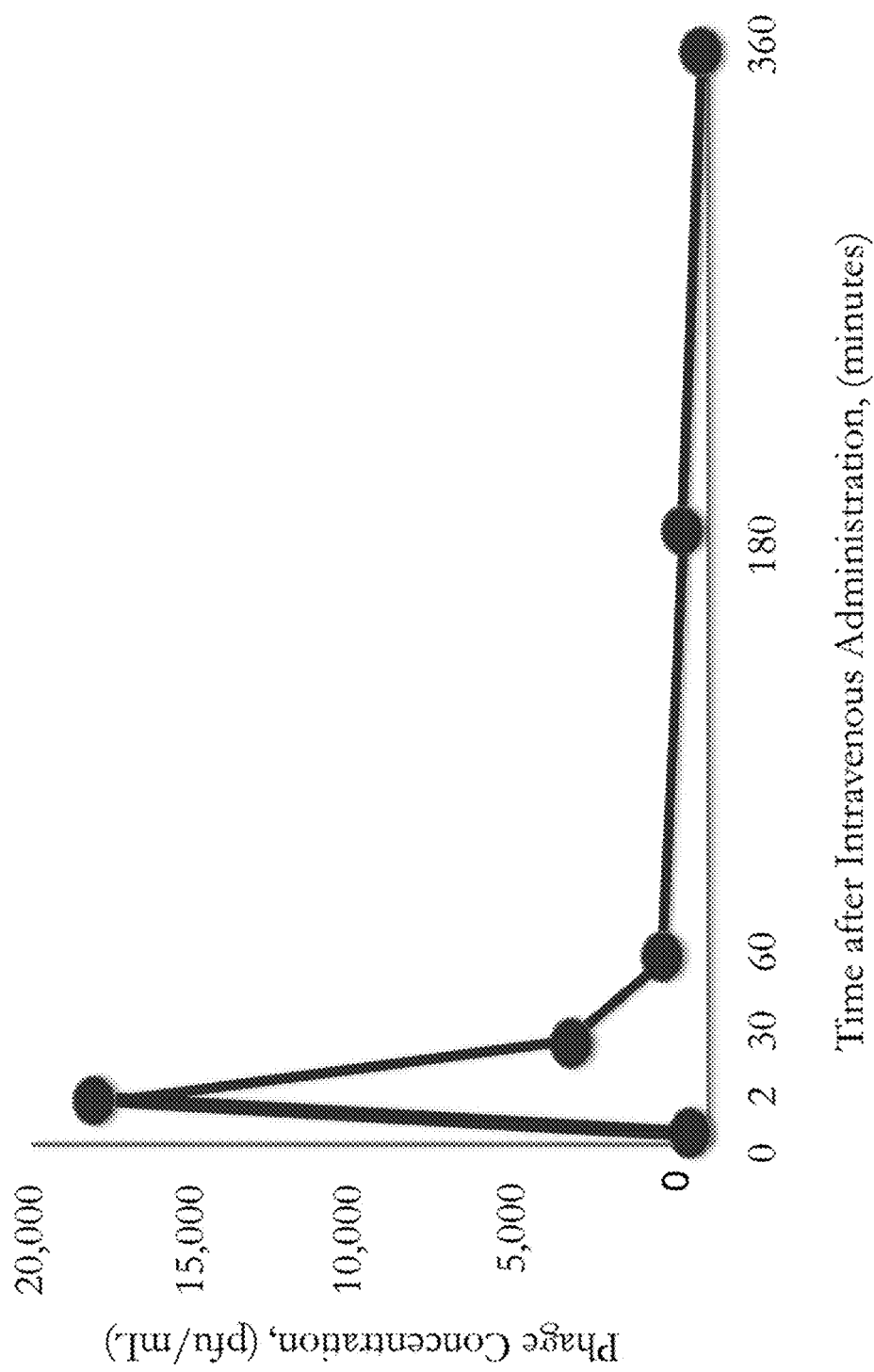
FIG. 18 depicts in vivo pharmacokinetics relevant to the case study described in Example 5. Specifically, the graph depicts the plasma phage concentration vs. time after intravenous administration (i.e., how long the phage circulate in the bloodstream). Image courtesy of Dr. Robert Schooley, UCSD.

Phage Pharmacokinetics:

To better understand the pharmacokinetics of IV administration of therapeutic phages, we examined the titer of active phage in plasma samples after IV administration of Navy phage cocktail 1. We found phage concentrations of 18,000 plaque forming units (pfu) per ml in plasma five minutes after an IV bolus of $4 \times 10^9$ pfu of phages. These levels fell over the 6-hour dosing interval (FIG. 17). When pharmacokinetic studies were repeated after three weeks of phage therapy, no phage activity could be demonstrated in the plasma by 5 minutes after administration presumably because of the emergence of a phage-specific antibody response (not shown). FIG. 18 also depicts in vivo pharmacokinetics relevant to the case study described herein. Specifically, the graph depicts the plasma phage concentration vs. time after intravenous administration (i.e., how long the phage circulate in the bloodstream).

Figure 19:
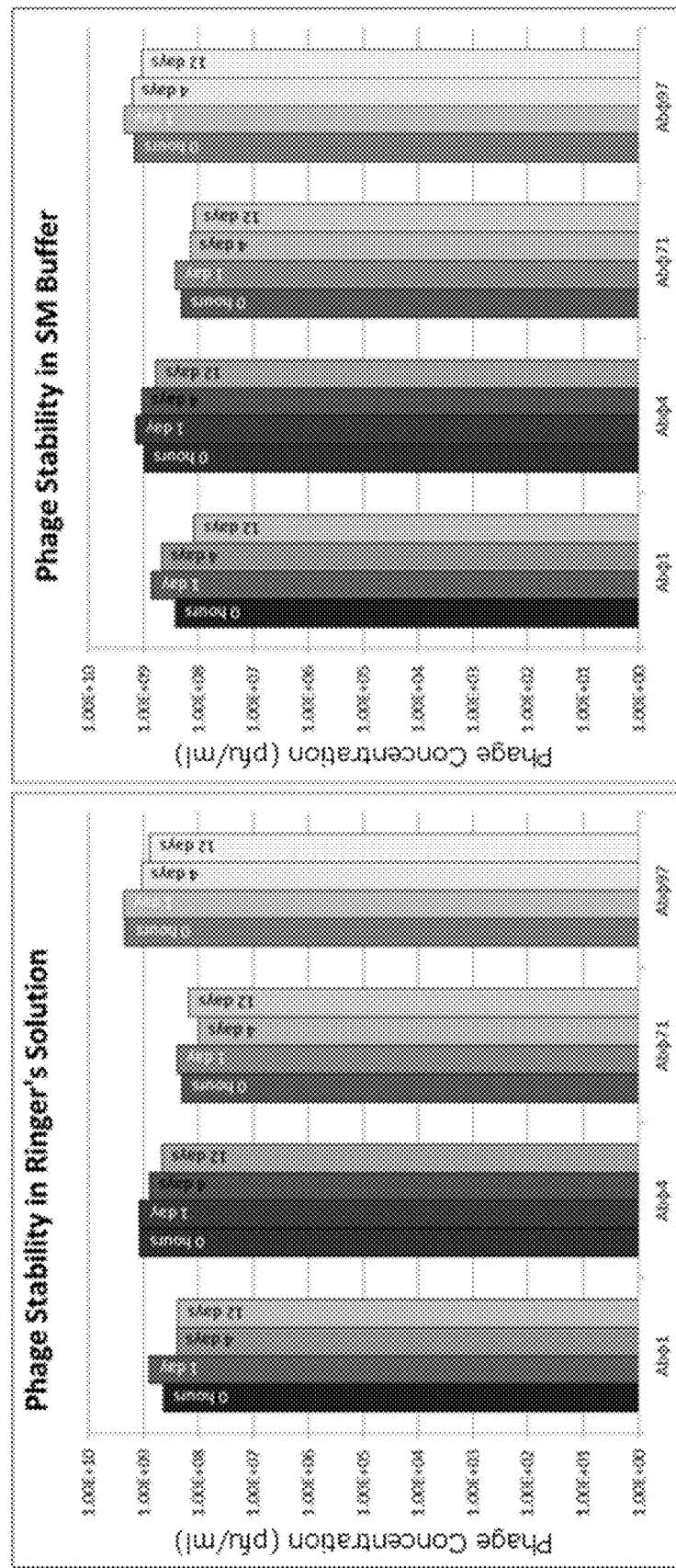
FIG. 19 depicts the stability of various phages in Ringer's Solution and SM buffer relevant to the case study described in Example 5.

FIG. 19 depicts the stability of various phage discussed in this example in Ringer's Solution and SM buffer. Data indicate that the isotonic properties of Ringer's solution make it a suitable buffer for phage cocktails. Specifically, in this case, Ringer's solution was used to dilute phage samples that were sent to USDC, while "SM buffer" is a negative control buffer commonly used in phage dilutions. Phage samples of approximately $10^9$ pfu/ml were added to 90 microliters Ringer's Solution or SM buffer and stored at 4° C. Each sample was titrated at 0 hours, 1 day, 3 days, and 1 week after incubating at 4° C.

Discussion

Data in this example supports further study of the use of phage therapy in treating patients with highly MDR bacterial infections with limited therapeutic options. As with any uncontrolled clinical observation, there are a number of important caveats; mostly we cannot unequivocally exclude the possibility that reversal of his clinical deterioration was unrelated to the phage therapy. Nonetheless, after an inexorably downhill clinical course over the prior three months to the point that discussions about clinical futility had been initiated, a clear turning point was observed within 48 hours of starting intravenous phage therapy. The potential interplay between the phages used in his therapy and minocycline is also complex. His organism rapidly became resistant to colistin and tigecycline earlier in his course but activity of minocycline was maintained for several weeks when it was added to his phage therapy five days after phage therapy was initiated. We were able to demonstrate additive in vitro activity between the phages and sub-inhibitory concentrations of minocycline when used in combination against a phage-resistant *A. baumannii* isolate.

Additive or synergistic activity has been previously demonstrated both in vitro and in animal model systems between phages and traditional antibiotics (Comeau A M et al., PLoS One 2007; 2:e799). Bacterial mutation to phage resistance has also been associated with significant fitness costs for the bacterium. Surface features such as capsule and LPS may be used as phage receptors but can also be pathogenicity factors, and their loss may result in attenuated virulence (Leon et al Front. Microbiol 2015; 6:343). Although *A. baumannii* was not immediately cleared from abscess cavity drainage or bronchial washings, strains with substantially reduced susceptibility to the phages administered subsequently emerged under the selective pressure of phage therapy. This strongly suggests the *A. baumannii* population evolved in response to selection pressure exerted by the phages. The bacterial isolates from this study, as well as the phages used in treatment, are currently being characterized at the genetic level to facilitate our understanding of the mechanisms involved in the apparently simultaneous decrease of antibiotic resistance and rise of phage resistance during the course of this patient's treatment.

A number of concerns have been raised about the potential toxicities and the practicality of phage therapy for serious bacterial infections e.g., regarding the possibility that an accelerated lysis of Gram-negative bacterial pathogens could release clinically significant levels of endotoxin (Wittebole X et al. Virulence 2014; 5:226-35). While our patient's clinical instability at the time therapy was initiated made it difficult to detect all but the most dramatic deleterious clinical effects of phage therapy, no adverse effects of phage administration were evident in association with either the intracavitary or IV phage administrations. Since phages often have narrow host ranges it was necessary to identify within a relatively short period of time several unique phages that were capable of lysing the patient's particular strain of *A. baumannii*. The successful outcome was achieved despite the fact that the patient's MDR isolate was insensitive to the vast majority of the *A. baumannii* phages initially available from diverse sources. Through labor-intensive enterprises, two laboratories were able to identify, propagate and purify four bacteriophages each with lytic activity for the MDR isolate within 10 days of receiving it.

As might be expected, especially given the immense size of the patient's *A. baumannii* population before phage therapy was started, *A. baumannii* isolates characterized after the start of phage therapy had reduced susceptibility to the initial phages over the first week of therapy. In our case, however, emergence of phage-resistant populations of *A. baumannii* was likely delayed by the use of combinations of phages and when the resistant bacteria were detected it was possible to identify a "second generation" phage that was active against the phage-resistant *A. baumannii* strain. Narrow bacterial host range of phages can also be a potential advantage in the treatment of MDR organisms since their specificity would be less likely to perturb the commensal microbiome of the patient. Moreover, as long as phages with alternative receptors can be obtained to counter the rise of phage-resistant strains, it is difficult to imagine anything like the advent of multi-drug resistant pump mechanisms that have arisen in response to conventional broad-spectrum antibiotic therapy. Other reported benefits of phage therapy include their ability to disrupt biofilms (Reindel R and Fiore C R Clin Infect Dis. 2017 Mar. 1. doi: 10.1093/cid/cix188. [Epub ahead of print]) and to exhibit synergistic activity or restore susceptibility to conventional antimicrobial agents (Fu W et al. Antimicrob Agents Chemother 2010; 54:397-404). Finally, the utility of phage lysates as vaccine adjuvants raises the possibility that phage therapy might be associated with a reduction in bioburden and enhanced immune clearance of the pathogen, possibly through the formation of antigenic complexes of phage and bacterial debris caused by lysis (Chan B K et al. Sci Rep. 2016; 6:26717).

We note herein that in this example, not all of the methods of the instant invention were used to arrive as the therapeutic phage combinations Navy phage cocktail 1 and Navy phage cocktail 2. For example, while an *A. baumannii* bacterial diversity set and a modest Tier 1 phage library were employed, a robust Tier 2 phage library was not available against *A. baumannii*. Given the patient's significantly large *A. baumannii* infection, and the inability to iteratively screen a robust Tier 2 phage library against *A. baumannii*, several different phage cocktails were eventually needed to treat the infection here. It is contemplated herein that using the complete method and reagents of the instant invention may be used in future case studies to develop superior phage cocktails. Indeed, it is contemplated herein that performing all the steps of the method of the instant invention would facilitate the discovery and compounding of a phage cocktail(s) better able to deal with the phage resistance that developed in the patient during treatment.

Example 6

In Vitro Susceptibility Testing for Combinational Treatment with Phages ("Checkerboard Assay")

The below "checkerboard assay" describes an in vitro assay that was used in conjunction with the case study described in Example 5. It is contemplated herein that this assay may be used along with the methods of the instant invention to facilitate the comparison of the treatment effect of a combination of phages (or phage cocktails) on clinical bacterial isolates, as well as treatment effects in the presence of antibiotics, antibodies, or other reagents.

As contemplated herein, in a particular embodiment, the assay may be performed using a liquid broth, e.g., tryptic soy broth, and microtiter plates to determine the bactericidal activities of a mixed phage treatment. For example, using a 96 well microtiter plate, a combination of two phages, e.g., "phage 1" and "phage 2", may be assayed by serially diluting samples of phage 1 along the ordinate, and serially diluting samples of phage 2 along the abscissa. Serial 10-fold dilutions of each phage are made on the 96 well plate so that concentrations from one 1000th of the minimum inhibitory concentration (MIC) to 1000 fold excess of MIC is included. As understood herein, the "minimum inhibitory concentration" (MIC) is the lowest concentration of a phage that will inhibit the growth of a bacteria after overnight incubation. The resulting "checkerboard" of serial dilutions will yield every combination of the two phages that contains the highest concentration of each phage at the opposite corner. The plate is then inoculated with an appropriate titer of clinical bacterial isolate (e.g., a total of 10 clinical bacterial isolates may be tested using a 96 well plate) and incubated at 37° C. for a designated amount of time (e.g., 22 hours). The plate is then read using the assay described in Example 1, and the results may be displayed graphically. A schematic diagram of possible outcomes of the test results are depicted in FIG. 20.

Figure 20:
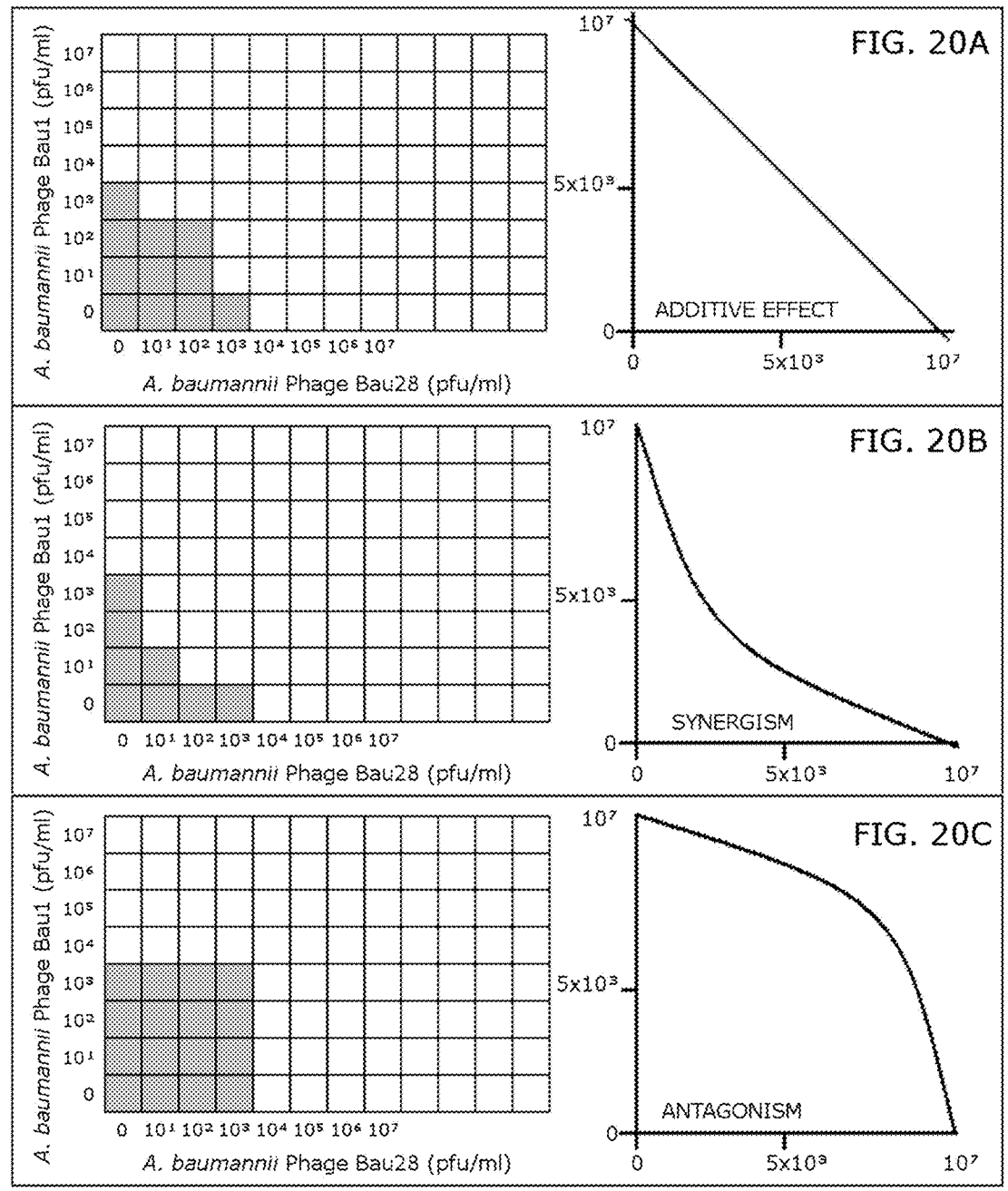
FIG. 20A, FIG. 20B and FIG. 20C depict the experimental design of a "checkerboard assay" titration of phage mixture for bacterial isolates discussed in Example 6. Each square represents a well on the microtiter plate. As depicted, increasing concentration of one phage ("phage 1", here labeled "Bau1") is distributed along the vertical axis and the other phage ("phage 2", here labeled "Bau28") is distributed along the horizontal axis. The hatched squares indicate bacterial growth. Three possible outcomes of this experiment are presented in FIG. 20A, FIG. 20B and FIG. 20C.

Referring to FIG. 20, synergy may be most likely expressed when the ratio of the concentration of each phage to the MIC of that phage is the same for all components of the mixture (e.g., a mixture that contains $10^2$ pfu/ml of phage 2 with an MIC of $10^4$ pfu/ml and $10^4$ pfu/ml of phage 1 with an MIC of $10^6$ pfu/ml). Because the variability of the techniques will be approximately one 10-fold dilution, a combination should differ by at least two 10-fold dilutions from the additive result to be considered synergistic.

In another particular embodiment, the assay may be used in combination with the assay described in Example 1 as an in vitro method for comparing the treatment effect of a phage or phage cocktail of the instant invention on MDR bacterial isolates in presence of various antibiotics, e.g., carbapenems, sulbactam, aminoglycosides, polymixyns, tigecycline, etc. For example, the phage may be diluted 2-fold along the ordinate of a 96 well plate, while one or more antibiotics may be diluted 2-fold along the abscissa. The plate is then inoculated with an appropriate titer of an MDR bacterial clinical isolate and incubated at 37° C., e.g., for approximately 22 hours. The plate is then read using the assay described in Example 1 and results interpreted as described in FIG. 20.

For example, this assay was performed in order to better understand the interaction between the phage cocktail and minocycline administered in combination to the patient discussed in Example 5. Specifically, each well of a 96 well plate contained tryptic soy media with 1% tetrazolium dye (v/v) for bacterial growth media. The antibiotic at a concentration of 2× the Minimal Inhibition Concentration (MIC 32 ug/ml) was added to row A, from column 1 through 8. The wells with antibiotics were then serially diluted 1:1 from row A down to row F. Phage were then added to each well starting at $10^7$ pfu per well in column 1 and then serially diluted 1:10 across from column 1 to 6. All wells were then inoculated with approximately $10^4$ cfu of bacteria per well. This design allows for antibiotic dilutions going down the columns and dilutions of phage going across the rows. Columns 7 and 8 represent antibiotic control wells and rows G and H represent phage control wells. However, wells G7, G8, H7, and H8 represent bacteria only control wells. Results of this study are provided herein as FIG. 15H which shows the additive inhibitory activity of the Navy phage cocktail 1 ($10^5$ pfu) and a sub-lethal concentration of minocycline (0.25 µg/mL) against A. baumannii strain TP3. The $IC_{50}$ of A. baumannii strain TP3 to minocycline by ETEST (bioMerieux USA, Durham, N.C.) was 4 µg/mL.

The assay can be performed with various combinations of individual phages to assay differences in therapeutic activity of different combinations. In addition, this method can be used to characterize the treatment effect of other various combinations of phages, e.g., a phage cocktail in combination with an individual phage, or the effect of combining two different phage cocktails, etc. In addition, it is contemplated herein that one can use this checkerboard assay to evaluate the type of interaction that might occur between a phage cocktail and a bacterial pathogen in the presence of neutralizing antibodies present in a subject's serum. Indeed, phage therapy may trigger the development of phage neutralizing antibodies in a patient's body due to a host immune response against the phages. Thus, in a particular embodiment, during prolonged phage treatment (e.g., more than 12 to 14 days) one can use this assay to evaluate the efficacy of a phage cocktail on the patient's bacterial pathogen in the presence of various dilutions of the patient's serum. Accordingly, this assay can be used to understand whether new phages may be useful to continue treatment as a way to overcome antibody mediated phage neutralization.

Thus, similar to the assay described above, in a particular embodiment, the evaluation may be performed using microtiter plates containing tryptic soy broth which permits the assessment of the bactericidal activities of phage and antibodies. Briefly, serial 10-fold dilutions of a phage cocktail could be used so that concentration from one $1000^{th}$ of MIC to 1000 fold excess of MIC will be included. For example, the phage cocktail may be serially diluted along the ordinate, while a patient's serum may be diluted (10 fold dilutions) along the abscissa. The resulting checkerboard will yield every combination of phage cocktail and serum antibodies, and contain the highest dilutions of phage cocktail and serum antibodies at the opposite corner. See FIG. 24. The plate may then be inoculated with an appropriate titer of the clinical bacterial isolate and incubated at 37° C., e.g., for approximately 20-48 hours. The plate is then read using the assay described in Example 1. The result of this test may be displayed graphically to facilitate the interpretation such as provided in FIG. 20 (modified such that the x axis represents "antibody dilutions"). In this embodiment, "antagonistic" or inappropriate immune results are indicated where the result of the phage and antibody treatment is significantly less than the best individual response; additive results reflect when the phage and antibody treatment is equal to the combined action of each of the components used separately; and synergistic results are depicted when the phage and antibody treatment is significantly better than the additive response. Autonomous or indifferent results are depicted when the results of the phage and antibody treatment is equal to the result with the phage itself (data not shown.)

Example 7

Bacteriophage Therapy Sterilized Refractory *Pseudomonas* Bacteremia in a Two Year Old Given the clinical success described in Example 5, another opportunity arose to treat a human patient with a phage cocktail compounded according to the methods of the instant invention. As described in detail below, a pediatric patient experiencing recalcitrant MDR *Pseudomonas aeruginosa* infection complicated by bacteremia/sepsis with limited antibacterial options due to resistance, allergies, and inability to achieve source control was administered a cocktail of two bacteriophages targeting the infectious organism introduced on two separate occasions. The phage therapy sterilized the bacteremia.

A two-year-old male with a history of DiGeorge syndrome and complex congenital heart disease including an interrupted aortic arch type B, posterior malalignment of a ventricular septal defect (VSD), subaortic stenosis, bicuspid aortic valve and *secundum* atrial septal defect (ASD) underwent multiple surgeries including aortic arch plasty and primary anastomosis, ascending aortic pseudoaneurysm repair, ASD/VSD closures, and pacemaker placement for second degree heart block. He was transferred to Children's National Medical Center in Washington D.C. after experiencing recalcitrant *Pseudomonas aeruginosa* bacteremia after the ASD/VSD closures despite treatment with multiple appropriate antibiotic courses to which the organism was initially susceptible (including meropenem, tobramycin, aztreonam, and colistin). Whole-body imaging revealed no evidence of endocarditis, but presumptive infected fluid collections adjacent to the ascending aorta, and cerebral mycotic aneurysms. Cardiothoracic surgery deemed him not a candidate for source control due to the risks of catastrophic bleeding stemming from extensive collateral circulation. He exhibited Stevens-Johnson syndrome reactions to cephalosporin antibiotics and fluoroquinolones. As the infection persisted, he slowly developed an increasing need for blood pressure support, and increasingly severe arrhythmias. Eventually, the organism exhibited resistance to all aforementioned antibiotics, however, the regimen of meropenem, tobramycin, and colistin was continued exploiting antibacterial synergy.

Given the lack of adjunctive antibiotic options (constrained by multiple allergies to antibiotic classes), and inability to gain source control, the clinical team pursued a heroic intervention exploiting intravenous bacteriophage administration targeting *P. aeruginosa*. The treating physician submitted a plan of investigation and secured FDA emergency IND (eIND) approval for administering bacteriophage (serving as sponsor), and approval from the hospital's local IRB. Written consent was obtained from the parents after multiple multidisciplinary meetings, including ethics, with the family understating the gravity of the situation and lack of treatment options. The clinical plan delineated the frequency of phage administration, the estimated plaque forming units (PFU) administered per dosing, sterility and toxin data, and endotoxin levels.

The U.S. Navy has amassed a library of bacteriophages targeting *P. aeruginosa* (as well as other ESKAPE pathogens including *S. aureus, A. baumannii*, and Vancomycin resistant *enterococcus*). This library was established (and is intended to be expanded) to provide real time personalized phage cocktails to treat serious MDR infections. Accordingly, a bacteriophage cocktail exhibiting lytic activity against the isolate was identified exploiting reagents and methods disclosed in this invention. Specifically, once having received the clinical bacterial sample, a Tier 1 library of *Pseudomonas aeruginosa* specific bacteriophages against the patients isolate was screened, to which 25 were effectively lytic. We chose 2 of the most virulent (intensity of bacterial killing) and "diverse" (non overlapping binding sites) phages in our cocktail preparation. These virulent phages were selected on the basis of quick spot assay analysis on bacterial lawn on soft agar overlay.

We note herein that phage "viremia" may be measured in the blood after administration. Animal models suggest that viremia is quite transient given the host immune response and sequestration in the reticuloendothelial system (liver and spleen). As this was an eIND, we did not pursue specimen collections to assess phage viremia (contributing to characterization of phage pharmacokinetics).

The phage cocktail (consisting of 2-phages exploiting multi-valency to circumvent resistance and expedite sterilization) was purified, confirmed sterile, and had its endotoxin content characterized (Lonza Endpoint Chromogenic Assay, Lonza, Gaithersburg, Md.; data not shown). It was dosed at $3.5 \times 10^5$ PFUs every six hours. Given a lack of evidence-based clinical data to guide dosing, the actual PFU dosage was dictated by limiting the endotoxin units administered per FDA guidelines to 5-EU/kg-hr (introducing a factor of safety), while mirroring the bacteriophage dosing which proved successful in the successful clinical case of MDR *Acinetobacter baumannii* (discussed in Example 5). The antibacterial regimen was continued hoping to secure in vivo synergy.

The patient tolerated the first six doses of bacteriophage, but administration was subsequently held after decompensation concerning for anaphylaxis. This decompensation was subsequently attributed to progressive heart failure though endotoxin release could not be excluded as contributory.

Of note, we had no a priori prescription for dosing duration as such data doesn't currently exist; even though phage are capable of exponential multiplication in target bacterial strains, the initial dose of phage should be sufficient to control the bacteria population before it reaches a lethal threshold.

Figure 21:
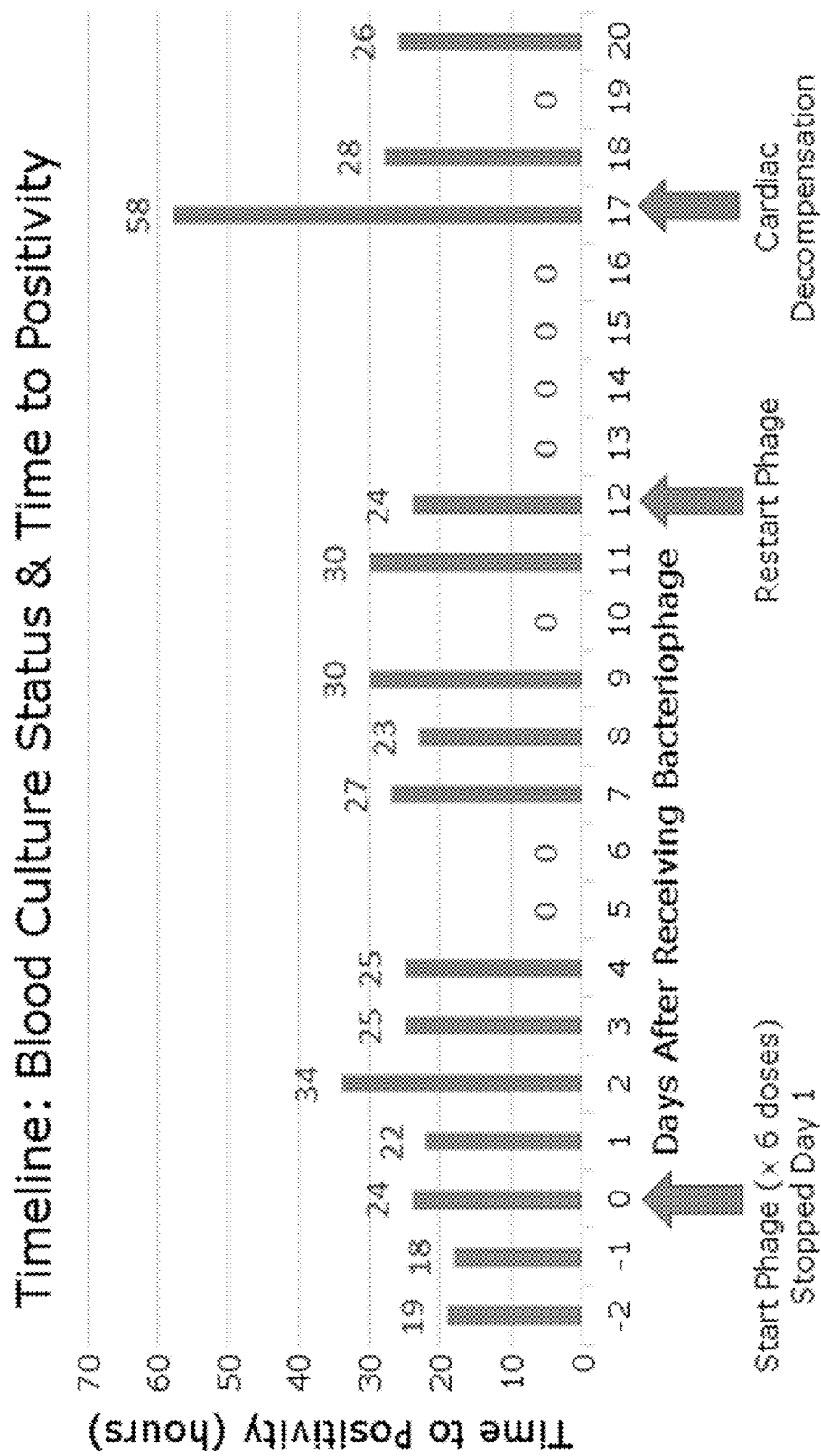
FIG. 21 depicts a timeline for blood culture status and time to positivity discussed in Example 7. Data demonstrate data for blood cultures which had reverted to positive, reverted to sterile again (within one day after reinstituting the original dosing) durably for several days coinciding with clinical improvement.

Additionally, in this specific case, we acknowledged that absent definitive source control, intuitively treatment durations would likely be considerably prolonged. Despite premature cessation of bacteriophage therapy (limited to 36-hours dosing), surveillance blood cultures exhibited increasing time to positivity, and those acquired on the fourth and fifth days post bacteriophage initiation were sterile, a remarkable observation given that all surveillance cultures (16 blood cultures) in the prior (30-days) were positive. The blood cultures reverted to positive in the ensuing days and the patient's prognosis continued to worsen. While off bacteriophage, a respiratory panel PCR from a bronchoalveolar lavage was positive for influenza treated with oseltamivir. After continued discussion with the family, ethicists, and subspecialties regarding lack of alternative treatment options, and continued isolate sensitivity to the original phage cocktail, (determined via a quick phage spot assay titration on the relapses positive bacterial isolate), and without identified host humoral responses targeting the phage, bacteriophage therapy was resumed (11-days post cessation). Remarkably, and reproducibly, shortly after resuming the bacteriophage therapy, the blood cultures which had reverted to positive reverted to sterile again (within one day after reinstituting the original dosing) durably for several days coinciding with clinical improvement (see FIG. 21).

Regrettably, prior to acquiring surveillance imaging, the patient decompensated developing severe arrhythmias, cardiac shock and septic shock (positive culture results with the same isolate) refractory to subsequent interventions. Although speculative, we presume this worsening, turbulent course was attributed to frank progression of the undrained fluid collections, antecedent influenza infection, and end-stage cardiac failure. Given the grave prognosis, the family elected to withdraw care after which the child died.

Discussion

We report herein a pediatric patient experiencing recalcitrant MDR *Pseudomonas aeruginosa* bacteremia/sepsis due to limited antibacterial options (constrained by both resistance and allergies to antibiotic classes) coupled to inadequate source control. Acknowledging the onerous proposition of attempting treatment without source control, as bacteriophages are purported to penetrate into sequestered fluid collections (biofilms), we endeavored to treat with intent to eradicate the infection. Despite the unfortunate outcome, we contend that we observed an important therapeutic signal as bacteriophage therapy sterilized the blood after both introductions (after 4 weeks of continuous bacteremia). The critical status undermined attempts at surveillance imaging therefore it is regrettable that we couldn't assess efficacy in resolving the infected fluid collections and mycotic aneurysms. Ideally, we would have executed IR-guided instillation directly into the fluid collections, but this was contraindicated for the reasons delineated above. Undoubtedly, optimal outcomes employing bacteriophage therapy will require the concerted combination of antimicrobials coupled to source control. We speculate that coupled to the cardiac decompensation, the viral infection likely sequestered and undermined his limited immune response (DiGeorge syndrome) and precipitated the departure from homeostasis.

Although ostensibly we didn't achieve sterilization of all infectious nidi, it's difficult to ignore repeated blood sterilization with both bacteriophage introductions in this patient, hitherto bacteremic eclipsing 4-weeks. We speculate that earlier introduction (prior to the protracted bacteremia and maturation in infected fluid collections), source control followed by direct bacteriophage instillation into the fluid collections, and uninterrupted therapy may have durably sterilized the infectious fluid collections and achieved a superior clinical outcome.

In addition to the foregoing, we note herein that the identification of the phage cocktails described in this example and Example 5 was limited given the lack of robust tiered libraries. Thus, phage discovery and cocktail formulation were done simultaneously using available phages to the particular species of bacterial pathogen and, in the case of Example 5, a small Tier 1 uncharacterized *A. baumannii* library. As such it is contemplated herein that these cocktails were not as sophisticated as could have been generated by performing all the steps of the methods of the instant invention.

Example 8

Assessing Synergistic Combinations of Phage Cocktails and Antibiotics: Bacteriophage-induced Sensitivity to Carbapenem in Carbapenena Resistant Enterobacteriaceae (CRE): Carbapenem-Resistant (CR) *Klebsiella Pneumoniae*

As discussed above, it is contemplated herein that administration of the phage cocktails of the instant invention may resensitize MDR bacteria to previously ineffective antibiotics, and/or co-treatment of synergistic phage cocktails with an ineffective antibiotic may augment the effectiveness of the antibiotic allowing the antibiotic to regain clinical utility. Thus, in addition to bacterial lysis, the phage cocktail-mediated modulation of antibiotic efficacy, and the phage cocktail-mediated modulation of the infecting bacterial populations themselves (e.g., outgrowth of less virulent or nonresistant emergent strains), may prove to be consequential features for phage product development, optimization, and clinical use.

Data regarding the combined effects of personalized phage cocktails and antibiotics will help determine the clinical course of treatment for a patient. Accordingly, it is contemplated herein that phage cocktails compounded according to the methods of the instant invention may be assayed in combination with an antibiotic to determine not only the therapeutic efficacy of a combination of a personalized phage cocktail and antibiotic, but also to detect any phage-mediated modulation of antibiotic efficacy on the target MDR pathogen. The below study of bacteriophage-induced sensitivity to carbapenem in carbapenem-resistant (CR) *Klebsiella pneumoniae* (*K. pneumoniae*) is an example of how such an assay may be performed.

Among MDR pathogens, carbapenem-resistant Enterobacteriaceae (CRE) are an increasing clinical problem nd few treatment options exist for CRE infections. CRE of clinical concern include *K. pneumoniae* and *E. coli*. Current treatment regimens include last-line antibiotics tigecycline, colistin, fosfomycin, and aminoglycosides. Unfortunately, treatment failures against CRE result in increases patient morbidity, particularly in immunocompromised patients, and can lead to toxic side-effects from extended use of ineffective antibiotics, and prolonged healthcare utilization. Accordingly, experiments using CR *K. pneumoniae* were performed to determine whether phage cocktails can modulate the effectiveness of carbapenem when administered simultaneously, and if the low-frequency phage-resistant populations that emerge during phage predation are consistently re-sensitized to carbapenem.

Materials and Methods:

Using the phage efficacy assay described in Example 1, $10^4$ cfu of meropenem$^R$ *K. pneumoniae* was grown at 37° C. for 48 hours in the following conditions: (a) alone; (b) meropenem or phage (MOI 100); and (c) meropenem and varying MOIs of phage (MOI 0.01-100). The concentration of meropenem used for the indicated cultures was 4 µg/ml. Phage Kp4640ϕ1 was used at an MOI of 100+/−meropenem, and serial dilutions to an MOI of 0.01 were also used with meropenem. The readout of this assay is bacterial growth hold-time. That is, the longer the growth hold-time, the more effective the treatment.

For a phage synergy study, *K. pneumoniae* 4640 was added at approximately $10^4$ cfu per well of a microtiter plate. Individual phages were added at an MOI of 100. All wells were incubated at 37° C. for 48 hours according to the assay methods in Example 1.

Figure 22:
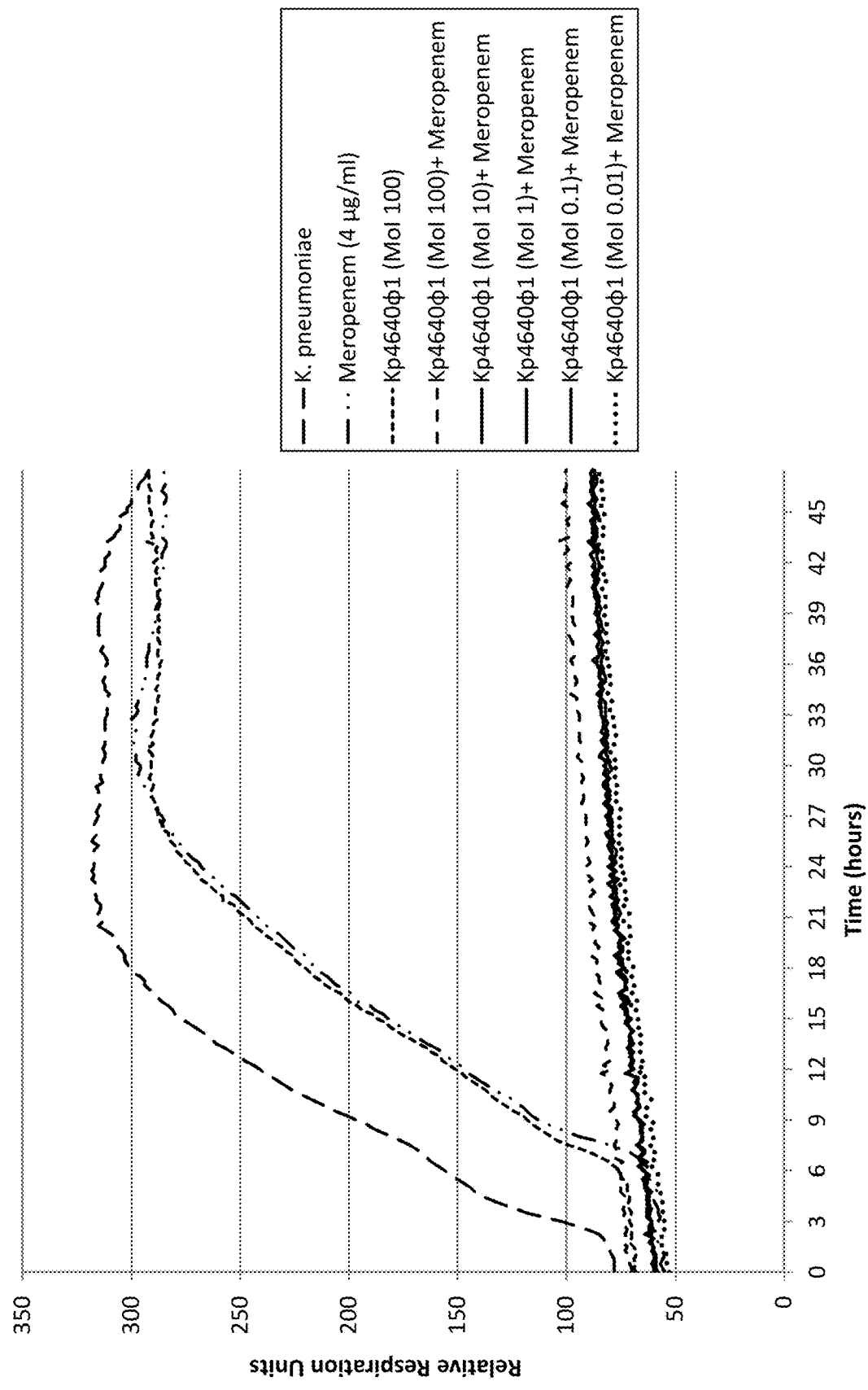
FIG. 22 depicts results from a 96-well photometric assay monitoring bacterial growth of *K. pneumoniae* 4640 in the presence of meropenem and phage discussed in Example 8. $10^4$ cfu of meropenem$^R$ *K. pneumoniae* 4640 was grown at 37° C. for 48 hours in the conditions listed. The concentration of meropenem used for the indicated cultures was 4 µg/ml. Phage Kp4640ϕ1 was used at an MOI of 100+/−meropenem, and serial dilutions to an MOI of 0.01 were also used with meropenem. At all MOIs tested, phage Kp464ϕ1 synergized with meropenem leading to a substantial increase in the hold-time and no detectable bacterial growth for at least 48 hrs at 37° C. The small baseline differences/drift with varying phage concentration are due to altered optical characteristics and do not reflect bacterial growth.

Results:

Data in FIG. 22 indicate that at all MOIs tested, phage Kp464ϕ1 synergized with meropenem leading to a substantial increase in the hold-time and no detectable bacterial growth for at least 48 hrs. Specifically, results indicate that meropenem alone and phage Kp4640ϕ1 (MOI 100) alone both had hold-times of approximately 6 hours. Meropenem and Kp4640ϕ1 together had a substantially increased hold-time. At all MOIs tested (0.01-100), Kp4640ϕ1 synergizes with 4 µg/ml meropenem and allowed for no detectable bacterial growth for at least 48 hrs.

Figure 23:
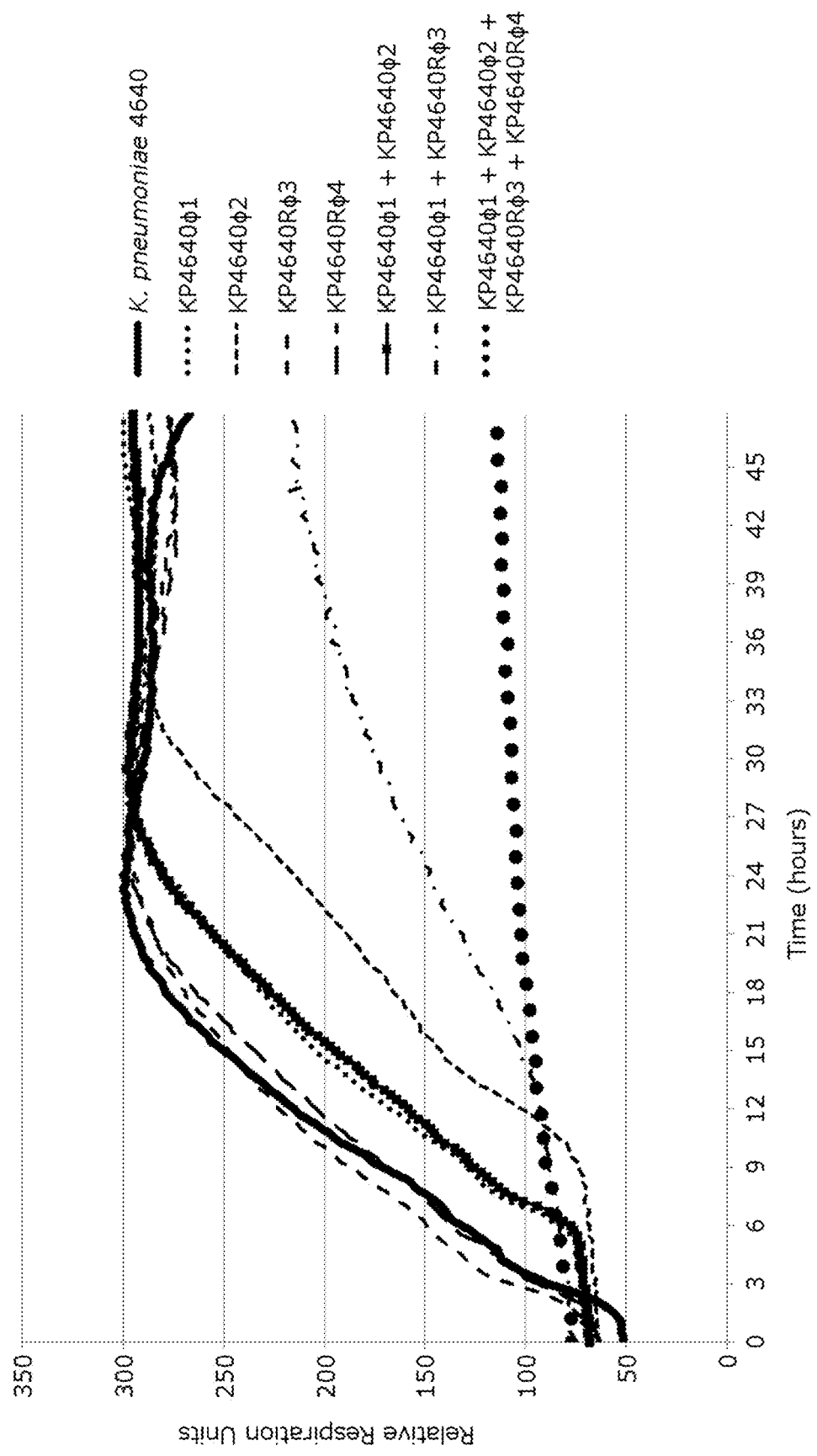
FIG. 23 depicts synergistic effects seen with a combination of phages against *K. pneumoniae* 4640 discussed in Example 8. *K. pneumoniae* 4640 was added at approximately $10^4$ cfu per well. Individual phage was added at an MOI of 100. All wells were incubated at 37° C. for 48 hours according to methods described in Example 1. Phage KP4640Rϕ3 and KP4640Rϕ4 alone showed no effect on the bacterial growth. Phage KP4640ϕ1 and KP4640ϕ2 both prevented growth of *K. pneumoniae* by 6 and 9 hours respectively. Mixing phage KP4640ϕ1 and KP4640ϕ2 showed to be as effective as KP4640ϕ1 alone, by delaying bacterial growth by 6 hours. Mixing phage KP4640ϕ1 and KP4640Rϕ3 proved to delay bacterial growth by up to 12 hours. Most notably, however, mixing all 4 phage used in this study prevented bacterial growth for 48 hours.

Data in FIG. 23 indicate that Phage KP4640Rϕ3 and KP4640Rϕ4 alone showed no effect on the bacterial growth. Phage KP4640ϕ1 and KP4640ϕ2 both prevented growth of *K. pneumoniae* by 6 and 9 hours, respectively. Mixing phage KP4640ϕ1 and KP4640ϕ2 showed to be as effective as KP4640ϕ1 alone, by delaying bacterial growth by 6 hours. Mixing phage KP4640ϕ1 and KP4640Rϕ3 proved to delay bacterial growth by up to 12 hours. Most notably, however, mixing all 4 phages used in this study prevented bacterial growth for 48 hours. Thus, data indicate that the phage combinations may work together with meropenem against resistant *K. pneumoniae*, allowing for regained antibiotic efficacy and therapeutic utility. In addition, the phage/antibiotic synergy observed in this example may generalize to other carbapenems and CREs.

It is important to note that all of the phages used here were uncharacterized wild phages as no Tier 1 or Tier 2 phage libraries against *K. pneumoniae* have yet to be created, thus finding these appropriate phages was a time consuming process requiring considerable work. Accordingly, it is contemplated herein that robust Tier 1 and Tier 2 libraries may be created with regard to this bacterial pathogen, and iterative screening according to the methods of the instant invention in the presence of antibiotics, may be performed to allow for the more rapid development of not only a synergistic cocktail, such as the 4-member cocktail here, but also cocktails that better synergize with antibiotics. Indeed, the time investment that was necessary to generate the disclosed cocktail against just one targeted bacterial strain underscores the power of the method of the instant invention to rapidly and reliably compound synergistic phage cocktails that not only may comprise counterintuitive combinations of phages, but also may even synergize with antibiotics, and thus allow one to regain therapeutic utility from currently ineffective antibiotics.

What is claimed is:

1. A method of compounding a phage cocktail directed against a bacterial pathogen comprising
    a). constructing a bacterial diversity set comprising diverse strains of the same species as said bacterial pathogen, said constructing comprising collecting a plurality of bacterial isolates of the same species as said bacterial pathogen, analyzing said plurality of bacterial isolates to identify bacterial isolates which are clinically, genotypically and/or metabolically diverse strains of said species of bacterial pathogen, and down selecting said plurality of bacterial isolates to include said clinically, genotypically and/or metabolically diverse strains of said species of bacterial pathogen to create said bacterial diversity set;
    b). collecting mixed phages from diverse environmental sources;
    c). constructing a Tier 1 archival phage library, said constructing comprising hosting the phages collected in step (b) on one or more of the diverse strains of said species of bacterial pathogen comprising the bacterial diversity set created in step (a) in order to identify and purify lytic phages against strains of said bacterial species, and selecting said lytic phages for the Tier 1 archival phage library;
    d). constructing a Tier 2 working phage library, said constructing comprising characterizing the Tier 1 archival phage library constructed in step (c) to identify and exclude phages which demonstrate undesirable and/or toxic characteristics, further screening remaining phages in the Tier 1 working phage library against one or more of the diverse strains of said species of bacterial pathogen comprising the bacterial diversity set created in step (a) to characterize host range of each said remaining phages, and selecting phages free of undesirable and/or toxic characteristics and having desirable host ranges for the Tier 2 working phage library;
    e). screening the Tier 2 working phage library constructed in step (d) for individual phages and/or various phage combinations that may be therapeutically effective against the bacterial pathogen, said screening comprising performing phage efficacy assays, wherein said phage efficacy assays comprise growing cultures of said bacterial pathogen with individual phages, and/or various phage combinations from the Tier 2 working phage library, and analyzing bactericidal activity against said bacterial pathogen by said individual phages and/or said various phage combinations in said cultures, wherein a suitable delay in bacterial growth and/or a lack of appearance of phage-resistant bacterial growth in said cultures indicates said individual phages and/or said various phage combinations may be therapeutically effective against the bacterial pathogen; and
    f). compounding one or more of said individual phages, and/or said various phage combinations that may be therapeutically effective identified in step (e) to form said phage cocktail.

2. The method of claim 1 wherein the bacterial pathogen is multidrug resistant.

3. The method of claim 1 wherein the bacterial pathogen is a clinical bacterial isolate causing infection in a subject.

4. The method of claim 3 wherein the clinical bacterial isolate causing infection in a subject is multidrug resistant.

5. The method of claim 1 wherein the plurality of bacterial isolates are clinical bacterial isolates.

6. The method of claim 5 wherein the clinical bacterial isolates are obtained from bona-fide human infections.

7. The method of claim 1 wherein the plurality of bacterial isolates is analyzed in step (a) to identify said genotypically diverse bacterial strains and/or to identify said metabolically diverse bacterial strains.

8. The method of claim 1 wherein the diverse environmental sources of said mixed phages are selected from the group consisting of soil, water treatment plants, raw sewage, sea water, lakes, rivers, streams, standing cesspools, animal and human intestines, and fecal matter.

9. The method of claim 1 wherein the identification and purification of lytic phages in step (c) comprises identifying and purifying phages that produce clear point plaques in classical plaquing assays against one or more of the bacterial strains in the bacterial diversity set created in step (a).

10. The method of claim 1 wherein the phages which demonstrate undesirable and/or toxic characteristics and are excluded from the Tier 2 library are selected from the group consisting of phages which carry toxin genes or other bacterial virulence factors, phages which possess lysogenic properties and/or carry lysogeny genes, phages which transduce bacterial virulence factor genes or antibiotic resistance genes, phages which carry any antibiotic-resistance genes or can confer antibiotic resistance to bacterial strains, and phages which elicit an inappropriate immune response and/or provoke a strong allergenic response in a mammalian system.

11. The method of claim 1 wherein the phages identified and selected for inclusion in the Tier 2 working phage library have different host range.

12. The method of claim 1 wherein the phages identified and selected for inclusion in the Tier 2 working phage library comprise a combination of phages having a broad bacterial host range and phages having a narrow bacterial host range.

13. The method of claim 1 wherein the phage efficacy assay in step (e) is performed using a high throughput assay comprising growing liquid cultures of said bacterial pathogen with said phages from the Tier 2 working phage library to detect phages which can cause a desirable delay in bacterial growth and/or the lack of appearance of phage-resistant bacterial growth, and wherein the delay in bacterial growth and/or the lack of appearance of phage-resistant bacterial growth in the phage efficacy assay in step (e) is monitored comprising the use of a photometric assay selected from the group consisting of fluorescence, absorption, and transmission assays.

14. The method of claim 1 wherein the phage cocktail compounded in step (f) is a synergistic phage cocktail.

15. The method of claim 1 further comprising rescreening the phage cocktails compounded in step (f) against the Tier 2 working phage library according to step (e) to identify possible additional therapeutically effective phage combinations.

16. The method of claim 15 wherein the phages of said additional therapeutically effective phage combinations act synergistically to cause a suitable delay in bacterial growth.

17. The method of claim 1 further comprising rescreening a phage combination and/or a phage cocktail which does not cause a desirable delay and/or a synergistic delay in bacterial growth, and/or does not cause a lack of appearance of phage-resistant bacterial growth to identify possible additional phages which may produce a desirable delay and/or a synergistic delay in bacterial growth and/or a lack of appearance of phage-resistant bacterial growth when added to the phage combination and/or the phage cocktail, wherein said rescreening comprises rescreening with one or more individual phages selected from the group consisting of phages in the Tier 2 working phage library, phages in the Tier 1 archival phage library, and new phages isolated from environmental sources.

18. The method of claim 1 further comprising updating the bacterial diversity set as additional strains of the same species as said bacterial pathogen are identified, and/or updating the Tier 1 archival phage library and/or the Tier 2 working phage library to include additional phages.

19. The method of claim 1 wherein the phage combination identified in step (e) and/or the phage cocktail compounded in step (f) comprise one or more phages that cannot infect said bacterial pathogen, but can infect emergent bacterial strains which arise following infection of said bacterial pathogen by other phages in the phage combination and/or the phage cocktail.

20. The method of claim 19 wherein said one or more phages that cannot infect said bacterial pathogen act synergistically with one or more phages that can infect said bacterial pathogen to produce said suitable delay in bacterial growth and/or said lack of appearance of phage-resistant bacterial growth.

21. The method of claim 19 wherein the emergent bacterial strains are less virulent than said bacterial pathogen, regain sensitivity to one or more drugs, and/or display reduced fitness for growth in the subject.

22. A method of treating a bacterial infection in a subject in need thereof comprising administering to the subject an effective amount of a pharmaceutical composition comprising a phage cocktail compounded according to the method of claim 1.

23. The method of claim 22 wherein the bacterial infection to be treated is selected from the group consisting of wound infections, post-surgical infections, and systemic bacteremias.

* * * * *